(12) United States Patent
Gaucher et al.

(10) Patent No.: US 9,321,788 B2
(45) Date of Patent: Apr. 26, 2016

(54) TRICYCLIC ANTIBIOTICS

(75) Inventors: Berangere Gaucher, Mulhouse (FR); Franck Hubert Danel, Bruebach (FR); Tong Xie, Haimen (CN); Lin Xu, Shanghai (CN)

(73) Assignee: BASILEA PHARMACEUTICA AG, Basel (CH)

( * ) Notice: Subject to any disclaimer, the term of this patent is extended or adjusted under 35 U.S.C. 154(b) by 0 days.

(21) Appl. No.: 14/124,144

(22) PCT Filed: Jun. 11, 2012

(86) PCT No.: PCT/EP2012/060953
§ 371 (c)(1),
(2), (4) Date: Apr. 22, 2014

(87) PCT Pub. No.: WO2012/171860
PCT Pub. Date: Dec. 20, 2012

(65) Prior Publication Data
US 2014/0235855 A1    Aug. 21, 2014

(30) Foreign Application Priority Data
Jun. 17, 2011   (EP) .................... 11170372

(51) Int. Cl.
| C07D 498/04 | (2006.01) |
| C07D 491/14 | (2006.01) |
| C07D 491/147 | (2006.01) |
| C07D 491/052 | (2006.01) |
| C07D 495/04 | (2006.01) |

(52) U.S. Cl.
CPC .......... *C07D 498/04* (2013.01); *C07D 491/052* (2013.01); *C07D 491/14* (2013.01); *C07D 491/147* (2013.01); *C07D 495/04* (2013.01)

(58) Field of Classification Search
CPC ............. C07D 498/04; C07D 491/14; C07D 491/147; C07D 491/052; C07D 495/04
USPC ....................... 544/105; 514/230.5
See application file for complete search history.

(56) References Cited

U.S. PATENT DOCUMENTS 8,927,541 B2 *  1/2015  Gaucher et al. ............. 514/229.5

* cited by examiner

*Primary Examiner* — Kahsay Habte

(57) ABSTRACT

The present invention relates to antibacterial compounds of formula I:

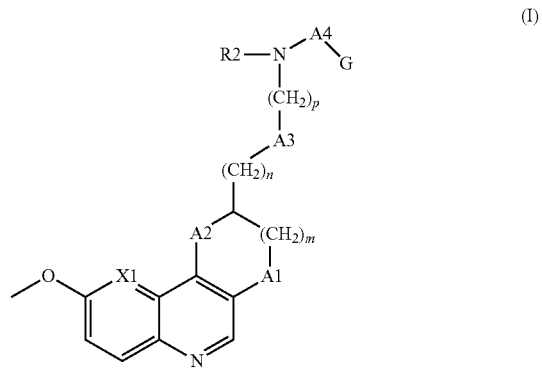

wherein all variable substituents are defined as described herein, which are useful for the treatment of bacterial infections.

28 Claims, No Drawings

TRICYCLIC ANTIBIOTICS

This application is a National Stage Application of PCT/EP2012/060953 filed Jun. 11, 2012, which claims priority from European Patent Application 11170372.4 filed on Jun. 17, 2011. The priority of both said PCT and European Patent Application are claimed.

The present invention relates to antibacterial compounds of a novel tricyclic chemical structure, processes for their manufacture and their use as a medicament for the treatment of bacterial infections.

BACKGROUND OF THE INVENTION

Several categories of tricyclic derivatives have been described showing antimicrobial activity. Such compounds may be useful as antibiotics for the treatment of microbial infections.

WO2009/128019 discloses antibiotic compounds having a tricyclic chemical structure of formula:

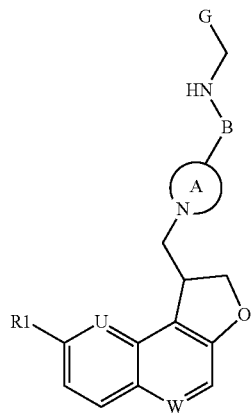

wherein
U and W represent nitrogen or (un)substituted CH;
R1 is alkoxy, halogen or CN;
Ring A represents pyrrolidin-1,3-diyl, piperidin-1,3-diyl or morpholin-2,4-diyl;
B is —CH$_2$—; and
G is a bicyclic heterocyclic ring system.

Other examples of tricyclic antibiotic compounds are described in WO2009/125808 and WO2009/125809, for example:

Example 7

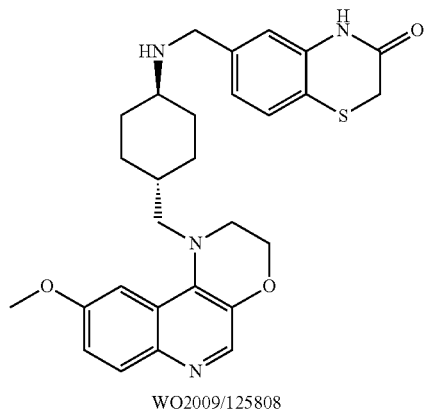

WO2009/125808

Example 19

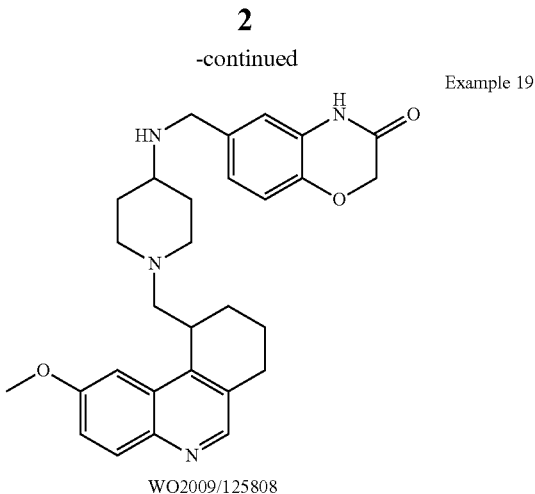

WO2009/125808

Example 37

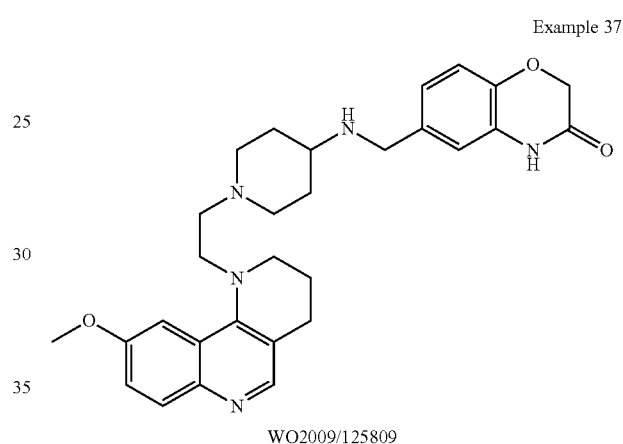

WO2009/125809

WO2010/015985 discloses antibiotic compounds with the general structure:

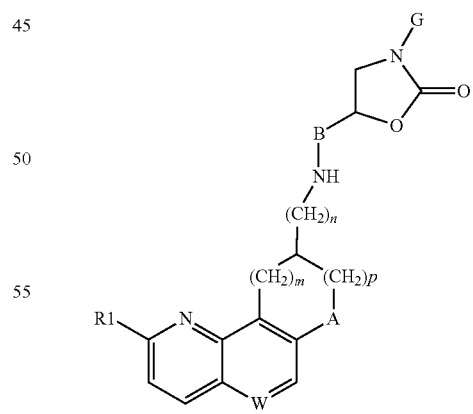

wherein
R1 is alkoxy or halogen,
W is CH or N,
A is —O— or —NH—,
B is —(C=O)— or —(CH$_2$)$_q$—;

G represents specific aryl or heteroaryl groups, namely

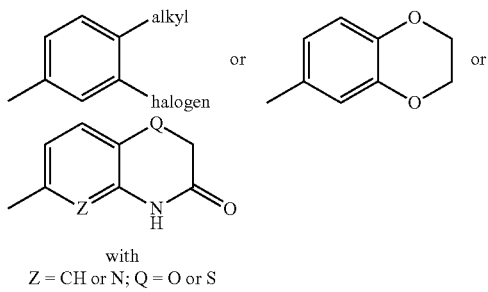

with
Z = CH or N; Q = O or S and
m is 0 or 1, n is 1 or 2, p is 0 or 1 and q is 1 or 2.

As generally known, the antimicrobial resistance against currently available antibacterials is increasing dramatically. Even multidrug resistant strains of Gram-negative bacteria (Pseudomonas, *Klebsiella, Enterobacter, Acinetobacter, Salmonella* species) and Gram-positive organisms (Staphylococcus, *Enterococcus, Streptococcus* species) have emerged and are becoming a serious public health problem. The number of patients with infections for which no effective antibacterial therapy exists increases steadily. This increasing resistance of pathogenic bacteria against known antibacterial agents, including multiple resistances, necessitates a continuous search for novel antibacterial substances, in particular compounds with novel structural characteristics.

SUMMARY OF THE INVENTION

The present invention provides such novel compounds, useful for the treatment of microbial infections, in particular novel tricyclic compounds with following general formula I

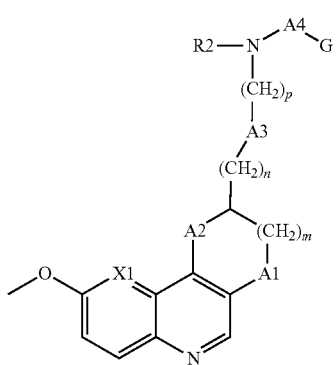

wherein
A1 represents —O—, —S— or —CH$_2$—;
A2 represents —CH$_2$— or —O—;
A3 represents C$_3$-C$_8$cycloalkylene; saturated or unsaturated 4 to 8-membered heterocyclodiyl with 1, 2 or 3 heteroatoms selected from nitrogen or oxygen, which group A3 is unsubstituted or substituted;
A4 represents C$_1$-C$_4$alkylene or —C(=O)—;
G represents aryl or heteroaryl, which is unsubstituted or substituted;
X1 represents a nitrogen atom or CR1;
R1 represents a hydrogen atom or a halogen atom;
R2 represents C$_1$-C$_4$alkyl or, preferably, a hydrogen atom;
m is 0 or 1;
n is 1; the —(CH$_2$)$_n$— group is unsubstituted or substituted;
p is 0 or 1;
or a pharmaceutically acceptable salt thereof.

DETAILED DESCRIPTION OF THE INVENTION

These compounds are useful antimicrobial agents effective against a variety of human and veterinary pathogens including among others Gram-positive and Gram-negative aerobic and anaerobic bacteria and mycobacteria.

The compounds of the invention or the pharmaceutically acceptable salt thereof also include enantiomers and diastereoisomers of said compounds or salts. Furthermore, in the context of the compounds of the invention the term "compound(s) or pharmaceutically acceptable salt(s) thereof" is meant to include also hydrates and solvates of the compounds of formula I and their salts.

The compounds of the invention show potent antibacterial activity against pathogenic bacteria, in particular against at least one of the following Gram-positive and Gram-negative pathogenic bacteria like *staphylococci, streptococci, enterococci, Escherichia coli, Haemophilus influenzae* or *Acinetobacter baumannii.*

The compounds exemplified in this application exhibit a minimum inhibitory concentration (MIC) (mg/L) of less or equal to 8 mg/L against at least one of the following microorganisms: *Acinetobacter baumannii; Enterobacter cloacae; Escherichia coli; Klebsiella pneumoniae; Proteus mirabilis; Pseudomonas aeruginosa; Stenotrophomonas maltophilia; Staphylococcus aureus; Enterococcus faecalis; Staphylococcus epidermidis; Streptococcus pneumoniae; Streptococcus pyogenes; Enterobacter aerogenes; Enterobacter cloacae* and *Enterococcus faecium.*

The expression "C$_1$-C$_4$alkyl" preferably refers to saturated, straight-chain or branched hydrocarbon groups having from 1 to 4 carbon atoms respectively like, for example, methyl, ethyl, propyl, iso-propyl, n-butyl, iso-butyl, tert-butyl. In combined expressions like e.g. C$_1$-C$_4$alk(yl)oxy, mono- or di(C$_1$-C$_4$alkyl)amino, the term "C$_1$-C$_4$alkyl" is understood in the same way. For the purposes of the present invention alkyl groups may also be substituted, e.g. by fluorine, chlorine, bromine or iodine atoms, carboxy, OH, =O, SH, =S, NH$_2$, =NH, cyano or NO$_2$, C$_1$-C$_4$alkoxy, C$_1$-C$_4$alkoxycarbonyl or mono- or di(C$_1$-C$_4$alkyl)amino, phenoxy, C$_5$-C$_6$heterocyclyl or the like.

The term "C$_1$-C$_4$alkylene" refers to divalent saturated straight-chain or branched hydrocarbon groups having from 1 to 4 carbon atoms like, for example, methylene, ethylene, 1,3-propylene, 1,2-propylene, 1,4-butylene and the like.

The expression "C$_3$-C$_8$cycloalkylene" preferably refers to a bivalent saturated or partially unsaturated (for example cyclic groups having one, two or more double bonds, such as a cycloalkenylene group), cyclic group containing from 3 to 8 carbon atoms, especially 3, 4, 5, 6 or 7, preferably 5 or 6 ring carbon atoms. Herein "cycloalkylene" is meant to include aromatic groups. The expression C$_3$-C$_8$cycloalkylene refers furthermore to groups in which one or more hydrogen atoms have been replaced each independently of the others by fluorine, chlorine, bromine or iodine atoms, carboxy, alkyl, alkoxy or mono- or di(C$_1$-C$_4$alkyl)amino or by OH, =O, SH, =S, NH$_2$, =NH, cyano or NO$_2$ groups, thus, for example, to bivalent residues of cyclic ketones such as, for example, cyclohexanone, 2-cyclohexenone or cyclopentanone. Further specific examples of cycloalkylene groups are cyclobutylene, cyclopentylene, cyclohexylene, cyclopentenylene, cyclohexadienylene.

The expression "heterocyclodiyl" as used herein preferably refers to a saturated or unsaturated bivalent 4 to 8-membered cyclic group as defined above in connection with the definition of cycloalkylene (including divalent heteroaromatic groups like e.g pyrazol-diyl), in which one or more (preferably 1, 2 or 3) ring carbon atoms have been replaced each independently of the other by an oxygen or nitrogen atom, preferably by a nitrogen atom. The expression heterocyclodiyl preferably refers furthermore to groups in which one or more hydrogen atoms have been replaced each independently of the others by fluorine, chlorine, bromine or iodine atoms or by carboxy, alkyl, alkoxy or mono- or di($C_1$-$C_4$alkyl)amino or by OH, =O, SH, =S, $NH_2$, =NH, cyano or $NO_2$ groups. Examples are piperidin-diyl, piperazin-diyl, morpholin-diyl, pyrrolidin-diyl, azetidin-diyl, tetrahydropyran-diyl, tetrahydrofuran-diyl, pyrazol-diyl, imidazol-diyl. Preferred are saturated 4 to 6-membered heterocyclodiyl groups in which one or two ring carbon atoms have been replaced by an oxygen or preferably nitrogen atom.

The expression "aryl" as used herein preferably refers to an aromatic group that contains one or more rings and from 6 to 14 ring carbon atoms, preferably from 6 to 10 (especially 6) ring carbon atoms. The expression aryl refers furthermore to such groups in which one or more hydrogen atoms have been replaced each independently of the others by alkyl, fluorine, chlorine, bromine or iodine atoms or by carboxy, alkoxy, mono- or di($C_1$-$C_4$alkyl)amino, OH, $NH_2$, cyano or $NO_2$ groups. Examples are phenyl, 4-methyl-phenyl, 4-tert-butyl-phenyl, 3-fluoro-4-methyl-phenyl, 3-fluoro-4-(trifluoromethyl)-phenyl, naphthyl, biphenyl, 2-fluorophenyl, anilinyl, 3-nitro-phenyl or 4-hydroxyphenyl.

The expression "heteroaryl" as used herein preferably refers to an aromatic group that contains one or more rings and from 5 to 14 ring atoms, preferably from 5 to 10 (especially 5, 6, 8, 9 or 10) ring atoms, and contains one or more (preferably 1, 2, 3 or 4) oxygen or nitrogen or sulphur ring atoms. The expression heteroaryl refers furthermore to groups in which one or more hydrogen atoms have been replaced each independently of the others by fluorine, chlorine, bromine or iodine atoms or by carboxy, alkyl, alkoxy, mono- or di($C_1$-$C_4$alkyl)amino, OH, SH, $NH_2$, cyano, $NO_2$ or unsubstituted heteroaryl groups. Examples are pyridyl, imidazolyl, thiophenyl, thieno[3,2-b]thiophenyl, benzo[b]thiophenyl, furanyl, benzofuranyl, imidazolyl, benzimidazolyl, pyrrolyl, indolyl, oxazolyl, isoxazolyl, indazolyl, indolyl, pyridazinyl, quinolinyl, purinyl, carbazolyl, acridinyl, pyrimidyl, pyrazolyl and isoquinolinyl groups.

Further rings can be fused to the aryl and heteroaryl groups as defined above, in particular further cycloalkane and/or in particular heterocycloalkane groups.

For the purposes of this invention the term "cycloalkane" preferably refers to a saturated or partially unsaturated cyclic group which contains one or more, e.g. one or two rings and from 3 to 14 ring carbon atoms, preferably from 3 to 10, most preferably 5 or 6 ring carbon atoms. The term cycloalkane refers furthermore to such groups in which one or more hydrogen atoms have been replaced each independently of the others by fluorine, chlorine, bromine or iodine atoms or by carboxy, alkyl, alkoxy, mono- or di($C_1$-$C_4$alkyl)amino or by OH, =O, SH, =S, $NH_2$, =NH, cyano or $NO_2$ groups, thus, for example, cyclic ketones such as, for example, cyclohexanone or cyclopentanone. Further specific examples of cycloalkane groups are cyclopropane, cyclobutane, cyclopentane, cyclohexane, cyclopentene, cyclohexadiene.

The expression "heterocycloalkane" as used herein preferably refers to cycloalkane groups as defined above in which one or more, preferably 1, 2 or 3 ring carbon atoms have been replaced each independently of the others by an oxygen or nitrogen or sulphur atom. A heterocycloalkane group has preferably 1 or 2 ring(s) containing from 3 to 10, most preferably 5 or 6 ring atoms. The expression heterocycloalkane refers furthermore to groups in which one or more hydrogen atoms have been replaced each independently of the others by fluorine, chlorine, bromine or iodine atoms or by carboxy, alkyl alkoxy, mono- or di($C_1$-$C_4$alkyl)amino or by OH, =O, SH, =S, $NH_2$, =NH, cyano or $NO_2$ groups. Examples are a piperidine, piperazine, morpholine, pyrrolidine, thiomorpholine, tetrahydrothiophene, [1,4]dioxane, tetrahydropyrane, tetrahydrofurane or pyrazo line and also lactams, lactones, cyclic imides and cyclic anhydrides, like e.g., morpholin-3-one or thiomorpholin-3-one.

The expression halogen refers to fluorine, chlorine bromine and iodine.

Certain compounds of formula I may contain one, two or more centres of chirality. The present invention therefore includes both all pure enantiomers and all pure diastereoisomers and also mixtures thereof in any mixing ratio. The present invention moreover also includes all cis/trans-isomers of the compounds of the general formula I and mixtures thereof. The present invention moreover includes all tautomeric forms of the compounds of formula I.

Preferred are compounds of formula I wherein X1 represents a nitrogen atom or —CH or —CF, more preferably, a nitrogen atom or a CH group.

In formula I A1 preferably represents —S— or, even more preferably —O—.

A2 is preferably —$CH_2$—.

Another preferred group of the compounds according to the present invention are those, wherein A3 represents a group selected from $C_5$-$C_6$cycloalkylene, in particular cyclohexylene, and saturated or unsaturated 4 to 6-membered heterocyclodiyl comprising one or two nitrogen or oxygen atoms as the heteroatoms, in particular one or two nitrogen atoms.

Especially preferred are the compounds of formula I wherein

A3 is selected from:

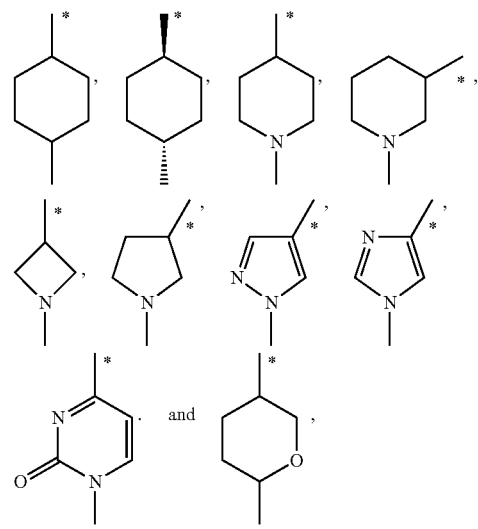

wherein * indicates the bond to the $(CH_2)_p$ group in formula I.

More preferably A3 is selected from

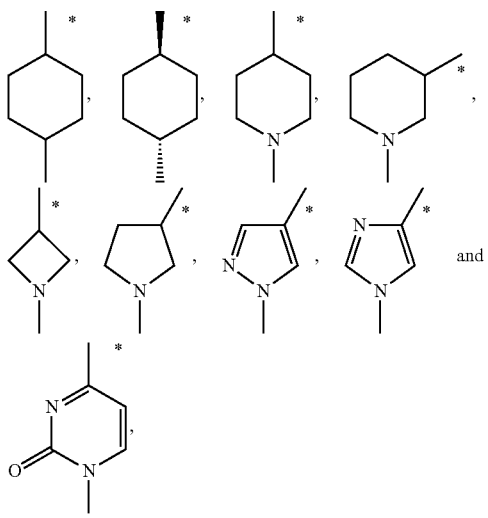

in particular from

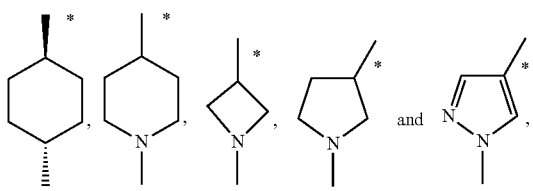

wherein * indicates the bond to the $(CH_2)_p$ group in formula I.

A3 may be unsubstituted or substituted, e.g. by one or more of the substituents mentioned above for $C_3$-$C_8$cycloalkylene or heterocyclodiyl groups. Other specific substituents of A3 include $C_1$-$C_4$alkoxycarbonyl, morpholinocarbonyl and hydroxy$C_1$-$C_4$alkyl like hydroxy methyl. Particularly preferred, A3 is unsubstituted.

The group G in formula I represents preferably a $C_6$-$C_{10}$aryl group which is unsubstituted or further substituted by one or more halogen atoms, in particular chloro or fluoro, and/or straight-chain or branched $C_1$-$C_4$alkyl groups which may optionally be further substituted by fluoro, like e.g. trifluoromethyl; or a phenyl group or a 5- or 6-membered heteroaryl group comprising heteroatoms selected from oxygen, sulphur or nitrogen, which phenyl group or 5- or 6-membered heteroaryl group are unsubstituted or substituted by one or more halogen atoms, in particular chloro or fluoro, and/or straight-chain or branched $C_1$-$C_4$alkyl groups which may optionally be further substituted by fluoro, like e.g. trifluoromethyl, or by an unsubstituted 5- or 6-membered heteroaryl group, to which phenyl group or 5- or 6-membered heteroaryl group further optionally a benzene ring or a 5- or 6-membered heteroarene ring, which is unsubstituted or substituted by one or more halogen atoms, in particular chloro or fluoro, and/or straight-chain or branched $C_1$-$C_4$alkyl groups which may optionally be further substituted by fluoro, like e.g. trifluoromethyl, or a heterocyclalkane ring may be fused which comprises six ring atoms and heteroatoms selected from oxygen, sulphur or nitrogen and optionally a =O group as substituent.

Preferred as group G are e.g. the following groups:

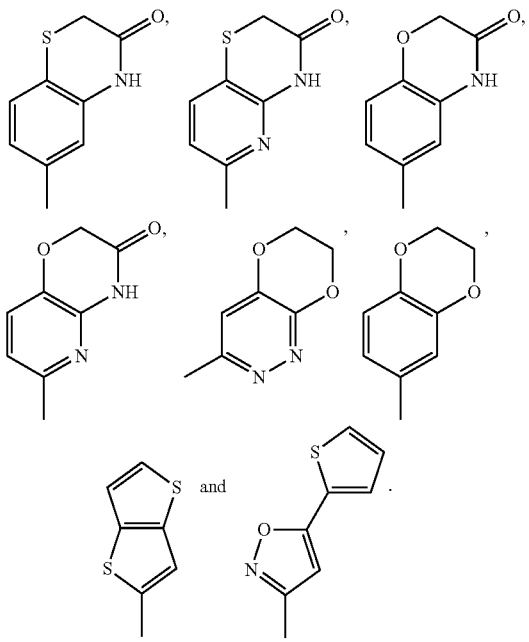

even more preferred are

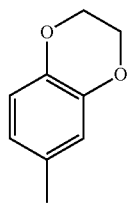

and especially

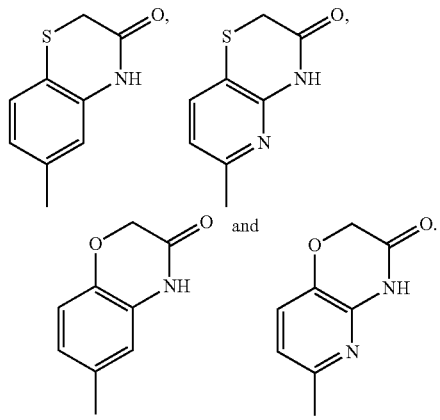

Particularly preferred are the compounds of formula I wherein the group —$(CH_2)_n$— is unsubstituted.

Particularly preferred are also the compounds of formula I wherein A4 is $C_1$-$C_4$alkylene, in particular methylene, or, more preferably, —C(=O)—.

The compounds of formula I wherein p is 0 are yet a further preferred group of the compounds of the present invention.

Particular preferred are e.g. the compounds of formula I having 2 or more, preferably all, of the following features in combination:
(a) X1 is a nitrogen atom or —CH—;
(b) A1 is —O—;
(c) A2 is —CH₂—;
(d) A3 is

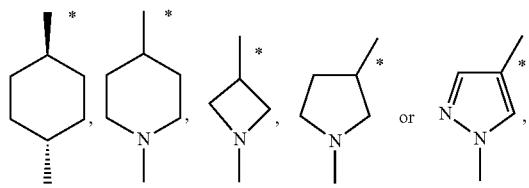

wherein
* indicates the bond to the (CH₂) group in formula I;
(e) A3 is unsubstituted;
(f) G is selected from a group of formula:

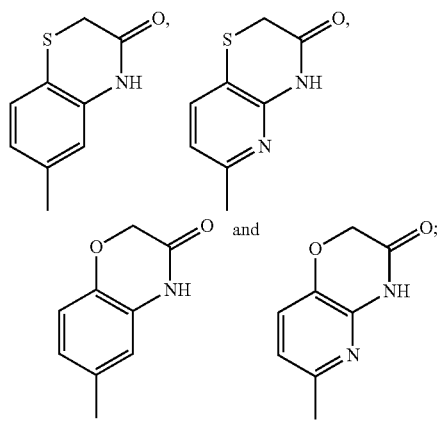

(g) —(CH₂)ₙ— is unsubstituted;
(h) A4 is —(CH₂)— or, preferably —C(=O)— and
(i) R2 is a hydrogen atom.

Particular preferred are combinations of one or more of the aforementioned features, when m is 1 and A4 is —C(=O)—, especially when furthermore p is 0.

A specific preferred example of these combinations of features are those wherein X1 in formula I is furthermore nitrogen. Another preferred example are such combinations wherein X1 is CH.

The aforementioned preferences can of course also be combined in any possible manner and all these binary or multiple combinations are considered to be specific embodiments of the present invention, even if not specifically recited.

Cardiovascular side effects are a frequently encountered problem in drug development and also for marketed drugs. In many cases, these effects are due to a compound induced prolongation of the QT interval in the electrocardiogram (ECG), which is associated with potentially fatal arrhythmia or "torsades des pointes". Several anti-infective agents like macrolides, ketolides and fluoroquinolones have been associated with QT prolongation.

The QT interval is a measure of the duration of ventricular depolarization and repolarization involving several membrane ion channels and transporters. In many cases, the inhibition of the delayed rectifier K⁺ current (IKr), which involves the human Ether-a-go-go Related Gene (hERG) potassium channel, has been linked to drug induced QT prolongation Inhibition of the hERG channel is therefore used to predict the risk of compound induced QT prolongation. Compounds of formula I have favorable hERG channel inhibition properties.

Examples of pharmacologically acceptable salts of the compounds of formula I are salts of physiologically acceptable mineral acids, such as hydrochloric acid, sulphuric acid and phosphoric acid, or salts of organic acids, such as methane-sulphonic acid, p-toluenesulphonic acid, lactic acid, acetic acid, trifluoroacetic acid, citric acid, succinic acid, fumaric acid, maleic acid and salicylic acid. Further examples of pharmacologically acceptable salts of the compounds of formula I are alkali metal and alkaline earth metal salts such as, for example, sodium, potassium, lithium, calcium or magnesium salts, ammonium salts or salts of organic bases such as, for example, methylamine, dimethylamine, triethylamine, piperidine, ethylenediamine, lysine, choline hydroxide, meglumine, morpholine or arginine salts.

The compounds of formula I may also be solvated, especially hydrated. Solvation and hydration may take place, for example, during the preparation process. The compounds according to the invention are therefore considered to include hydrates and solvates.

The compounds according to the present invention, pharmaceutically acceptable salts, solvates, hydrates thereof can be prepared e.g. by one of the processes (a), (b), (c), (d) or (e) described below; followed, if necessary, by:
removing any protecting groups;
forming a pharmaceutically acceptable salt; or
forming a pharmaceutically acceptable solvate or hydrate.
Process (a):
In this process variant a compound of formula I is prepared by reacting a compound of formula II

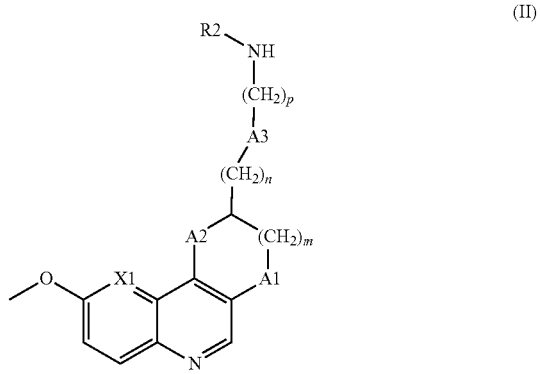

(II)

with a compound of formula III

G-A4b-L0    (III)

in which formulae
X1, R2, A1, A2, A3, G, m, n and p are as defined above for formula I,
L0 is selected from —CH₂Y, —CHO, —COOH and —COCl,
Y is a leaving group like mesylate, tosylate, triflate or halogen,
A4b is absent or represents C₁-C₃alkylene.

In certain cases L0 may require appropriate activation to allow a reaction of compounds of formulae II and III as described in more detail below.

Process (b):

This process variant can be used for the manufacture of compounds of formula I as defined above, wherein —(CH$_2$)$_n$— is unsubstituted.

In this process a compound of formula IV

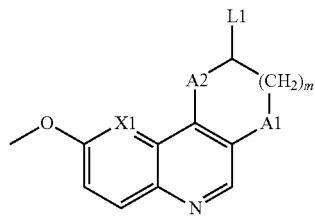
(IV)

is reacted with a compound of formula V

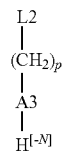
(V)

to generate a compound of formula VI

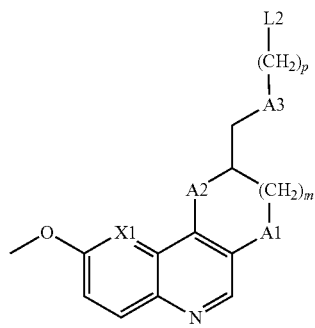
(VI)

in which formulae
X1, A1, A2, m and p are as in formula I,
L1 is selected from —CH$_2$Y or —CHO,
Y is a leaving group like mesylate, tosylate, triflate or halogen,
A3 is an unsubstituted or substituted, saturated or unsaturated 4 to 8-membered heterocyclodiyl group with 1, 2 or 3 heteroatoms selected from nitrogen or oxygen, at least one of which heteroatoms is a nitrogen atom which group A3 is linked to the moiety

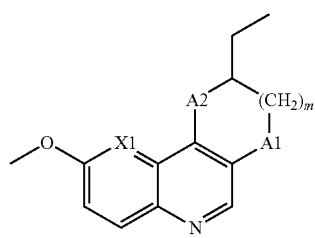

via a nitrogen ring atom of A3,
H$^{[-N]}$ in formula V represents a hydrogen atom bound to said nitrogen ring atom of A3, and
L2 is nitro or N(R2)E.

When L2 is nitro, said nitro group is reduced to an amino group and the amino derivative obtained is reacted with a compound of formula III G-A4b-L0     (III)

wherein G, A4b and L0 are as defined above for Process (a).
When L2 is N(R2)E,
then R2 is as in formula I, and
E is -A4-G (A4 and G being as defined in formula I) or an amino protecting group PG1, such as allyloxycarbonyl, benzyloxycarbonyl, 9-fluorenylmethylcarbonyl, tert-butoxycarbonyl or benzyl.

When E is an amino protecting group, said protecting group is removed and the deprotected intermediate is reacted with a compound of formula III G-A4b-L0     (III)

wherein G, A4b and L0 are as defined above.
Again L0 may, in certain cases, require appropriate activation to allow connection of the deprotected intermediate and the compound of formula III.

Process (c):

This process variant can be used for the manufacture of compounds of formula I as defined above, wherein A1 is —O—, A2 is —CH$_2$—, m is 0 and —(CH$_2$)$_n$— is unsubstituted.

In this process a compound of formula VII

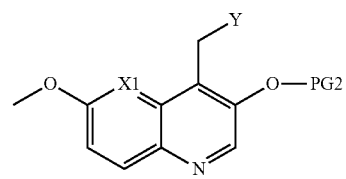
(VII)

is reacted with a compound of formula VIII

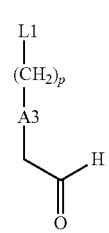
(VIII)

to generate a compound of formula IX

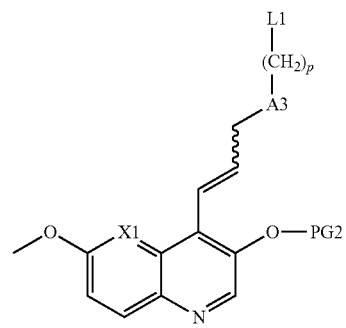
(IX)

in which formulae
X1, A3 and p are as in formula I,
L1 is nitro or N(R2)E,
R2 is as in formula I, and
E is an amino protecting group PG1 or a group of formula -A4-G, wherein
A4 and G have the same meaning as in formula I.
Y is a phosphonium salt or a phosphonate,
PG2 is a phenol protecting group (such as benzyl, allyl, tetrahydropyranyl, tert-butyl dimethylsilyl).

The compound of formula IX is further converted into a compound of formula XI

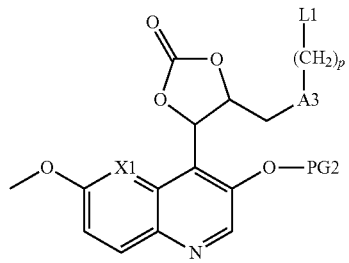
(XI)

wherein X1, PG2, A3, L1 and p are as defined above.

Said compound of formula XI is then transformed and cyclized to generate a compound of formula XIII

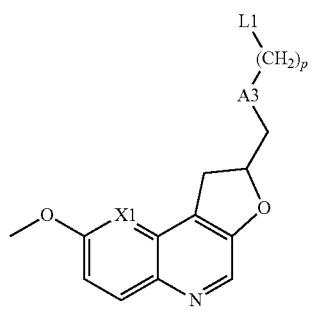
(XIII)

wherein X1, A3, L1 and p are as defined above.

Compound of formula XIII is finally transformed and reacted with a compound of formula III G-A4b-L0     (III)

wherein G, A4b and L0 are as defined above to generate compound of formula I following the procedures described in process (b).

Process (d):

This process variant can be used for the manufacture of compounds of formula I as defined above, wherein A1 is —O—, A2 is —CH$_2$—, m is 1 and —(CH$_2$)$_n$— is unsubstituted.

In this process a compound of formula XV

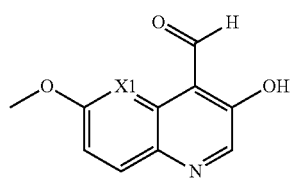
(XV)

is reacted with a compound of formula XVI

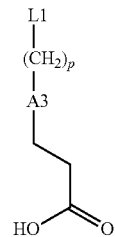
(XVI)

to generate a compound of formula XVII

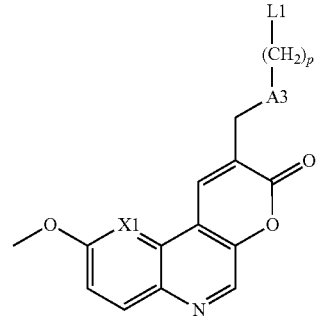
(XVII)

in which formulae
X1, A3 and p are as in formula I,
L1 is nitro or N(R2)E,
R2 is as in formula I, and
E is an amino protecting group PG1 or a group of formula -A4-G, wherein
A4 and G have the same meaning as in formula I.

The compound of formula XVII is further reduced and cyclized to generate a compound of formula XIX

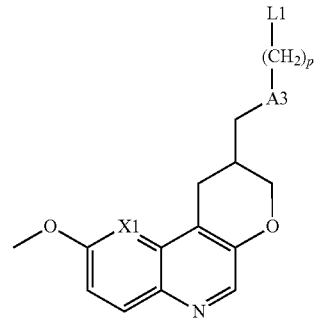
(XIX)

wherein X1, A3, L1 and p are as defined above.

Compound of formula XIX is finally transformed and reacted with a compound of formula III G-A4b-L0     (III)

wherein G, A4b and L0 are as defined above to generate compound of formula I following the procedures described in process (b).

Process (e):

This process variant can be used for the manufacture of compounds of formula I as defined above, wherein A1 is —O—, A2 is —CH$_2$—, m is 0 and —(CH$_2$)$_n$— is substituted.

In this process a compound of formula XXI

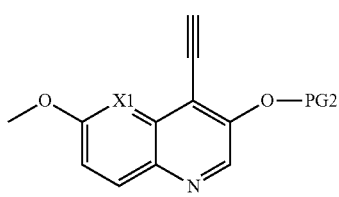
(XXI)

is reacted with a compound of formula VIII

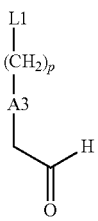
(VIII)

to generate a compound of formula XXII

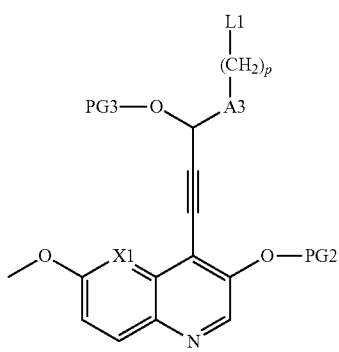
(XXII)

wherein X1, A3 and p are as in formula I,
L1 is nitro or N(R2)E,
R2 is as in formula I,
E is an amino protecting group PG1 or a group of formula -A4-G, wherein
A4 and G have the same meaning as in formula I,
PG2 is a phenol protecting group (such as benzyl, allyl, tetrahydropyranyl, tert-butyl dimethylsilyl),
PG3 is a hydroxyl protecting group (such as benzyl, acetyl, tetrahydropyranyl, trimethylsilyl, tert-butyl dimethylsilyl).

Said alkyne of formula XXII is reduced into the corresponding cis-alkene of formula XXIII

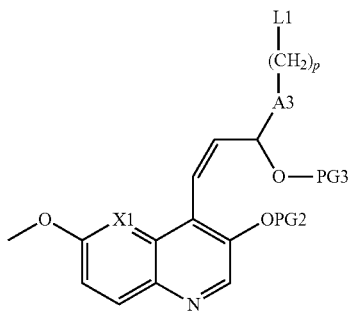
(XXIII)

wherein X1, A3, L1, PG2, PG3 and p are as defined above.

The compound of formula XXIII is further hydroxylated and protected to generate a compound of formula XXV

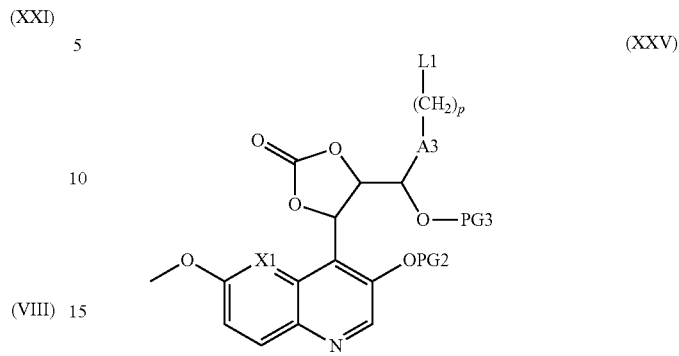
(XXV)

wherein X1, A3, L1, PG2, PG3 and p are as defined above.

The compound of formula XXV is further transformed and cyclized to generate a compound of formula XXVII

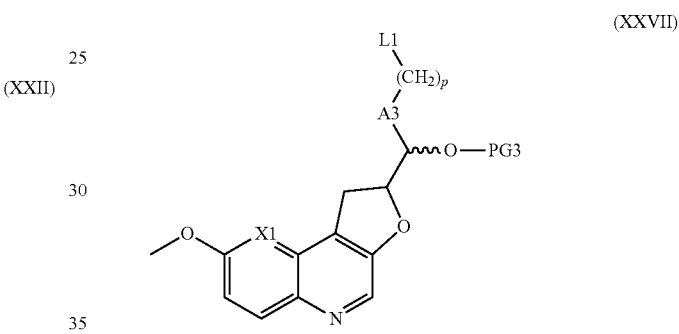
(XXVII)

wherein X1, A3, L1, PG3 and p are as defined above.

Said compound of formula XXVII is further transformed and reacted with a compound of formula III G-A4b-L0  (III)

wherein G, A4b and L0 are as defined above and following the procedures described in process (b) to generate compound of formula XXIX

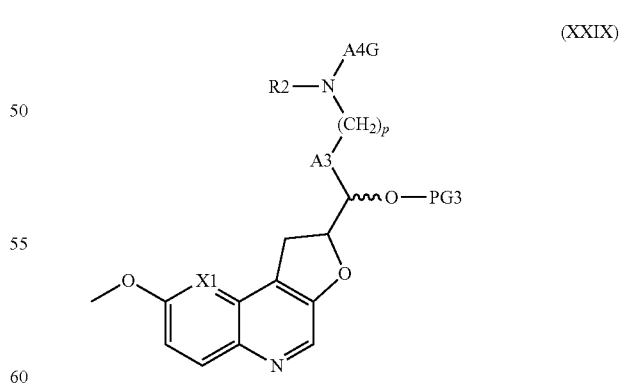
(XXIX)

wherein X1, A3, PG3 and p are as defined above and R2, A4 and G are as in formula I.

Final removal of the hydroxyl protecting group PG3 leads to the generation of compound of formula I.

The necessary starting materials for the synthetic methods as described herein, if not commercially available, may be made by procedures which are described in the scientific literature, or could be made from commercially available compounds using adaptations of processes reported in the scientific literature. The reader is further referred to *Advanced Organic Chemistry*, 5$^{th}$ Edition, by J. March and M. Smith, published by John Wiley & Sons, 2001, for general guidance on reaction conditions and reagents.

Furthermore in some of the reactions mentioned herein it may be necessary or desirable to protect any sensitive groups in compounds. Conventional protecting groups may be used in accordance with standard practice (for illustration see *Protective Groups in Organic Synthesis*, 3$^{rd}$ Edition, by T. W. Greene and P. G. M. Wuts, published by John Wiley & Sons, 1999).

The protecting groups may be removed at any convenient stage in the synthesis using conventional techniques well known in the art, or they may be removed during a later reaction step or work-up.

The compounds of formula I wherein —(CH$_2$)$_n$— is unsubstituted can be obtained as summarized in Schemes 1 to 4.

In Scheme 1, PG1 is an amino protecting group (such as allyloxycarbonyl (Alloc), benzyloxycarbonyl (Z), 9-fluorenylmethylcarbonyl (Fmoc), tert-butoxycarbonyl (Boc) or benzyl (Bn)) and the other symbols have the same meanings as previously described.

Compounds of formula V-1 are usually obtained by reacting the corresponding free amine with allyl, benzyl or fluorenylmethyl chloroformate or with di-tert-butyl dicarbonate in presence of a base such as sodium hydroxide, sodium hydrogencarbonate, triethylamine, 4-dimethylaminopyridine or imidazole. They can also be protected as N-benzyl derivatives by reaction with benzyl bromide or chloride in presence of a base such as sodium carbonate or triethylamine. Alternatively, N-benzyl derivatives can be obtained through reductive amination in presence of benzaldehyde. Further strategies to introduce other amino protecting groups have been described in *Protective Groups in Organic Synthesis*, 3$^{rd}$ Edition, by T. W. Greene and P. G. M. Wuts, published by John Wiley & Sons, 1999.

When L1 is —CH$_2$Y wherein Y is a leaving group like mesylate, tosylate, triflate or halogen, the reaction between

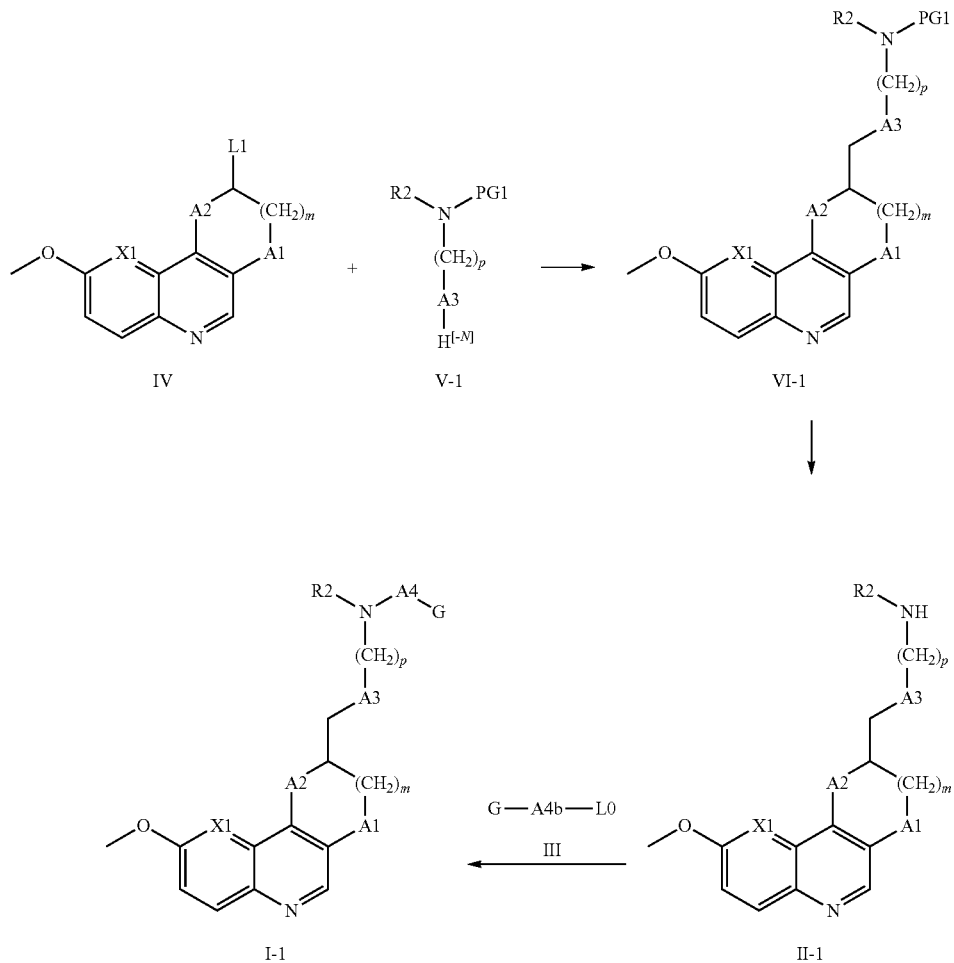

Scheme 1 compounds of formula IV and amines of formula V-1 to generate compounds of formula VI-1 is conducted at a temperature between −20° C. and 100° C. in a dry aprotic solvent like dichloromethane, acetonitrile, N,N-dimethylformamide, dimethyl sulfoxide or tetrahydrofuran without or with an inorganic base such as potassium carbonate or cesium carbonate, or an organic base such as triethylamine or N,N-diisopropylethylamine. Formation of the mesylate, tosylate or triflate compound can be achieved by reacting the corresponding alcohol with methanesulfonyl chloride or methanesulfonic anhydride, p-toluenesulfonyl chloride, trifluoromethanesulfonyl chloride or trifluoromethanesulfonic anhydride, respectively, in presence of a base such as triethylamine or the like in a dry aprotic solvent such as pyridine, acetonitrile, tetrahydrofuran or dichloromethane between −30° C. and 80° C.

When L1 is —CHO, the reductive amination between aldehydes of formula IV and amines of formula V-1 to generate compounds of formula VI-1 is conducted in a solvent system allowing the removal of the formed water through physical or chemical means (e.g. distillation of the solvent-water azeotrope or presence of drying agents such as molecular sieves, magnesium sulfate or sodium sulfate). Such solvent is typically toluene, n-hexane, tetrahydrofuran, dichloromethane, N,N-dimethylformamide, N,N-dimethylacetamide, acetonitrile, 1,2-dichloroethane or mixture of solvents such as methanol-1,2-dichloroethane. The reaction can be catalyzed by traces of acid (usually acetic acid). The intermediate imine is reduced subsequently or simultaneously with a suitable reducing agent (e.g. sodium borohydride, sodium cyanoborohydride, sodiumtriacetoxyborohydride; R. O. and M. K. Hutchins, *Comprehensive Organic Synthesis*, B. M. Trost, I. Fleming, Eds; Pergamon Press: New York (1991), vol. 8, p. 25-78) or through hydrogenation over a noble metal catalyst such as palladium on activated carbon. The reaction is usually carried out between −10° C. and 110° C., preferably between 0° C. and 60° C. The reaction can also be carried out in one pot. It can also be performed in protic solvents such as methanol or water in presence of a picoline-borane complex (Tetrahedron, 2004, 60, 7899).

Removal of the protecting group PG1 in compounds of formula VI-1 is carried out under standard conditions to generate compounds of formula II-1. For example the benzyl and the benzyloxycarbonyl groups are removed by hydrogenolysis over a noble metal catalyst (e.g. palladium or palladium hydroxide on activated carbon). The Boc group is removed under acidic conditions such as hydrochloric acid in an organic solvent such as methanol, dioxane or ethyl acetate, or trifluoroacetic acid neat or diluted in a solvent such as dichloromethane. The Alloc group is removed in presence of a palladium salt such as palladium acetate or tetrakis(triphenylphosphine)palladium(0) and an allyl cation scavenger such as morpholine, pyrrolidine, dimedone or tributylstannane between 0° C. and 70° C. in a solvent such as tetrahydrofuran. The Fmoc group is removed under mild basic conditions such as diluted morpholine or piperidine in N,N-dimethylformamide or acetonitrile. Further general methods to remove amine protecting groups have been described in *Protective Groups in Organic Synthesis*, 3$^{rd}$ Edition, by T. W. Greene and P. G. M. Wuts, published by John Wiley & Sons, 1999.

Compounds of formula I-1 wherein A4 is $CH_2$ can be obtained via reductive amination between intermediate II-1 and compound of formula III wherein L0 is —CHO, following procedures previously described for the preparation of compounds of formula VI-1.

Alternatively, compounds of formula I-1 wherein A4 is —$CH_2$— can be obtained from intermediate amine II-1 by reaction with a compound of formula III wherein L0 is —$CH_2Y$ and Y is a leaving group like mesylate, tosylate, triflate or halogen following procedures previously described for the preparation of compounds of formula VI-1.

Compounds of formula I-1 wherein A4 is —C(=O)— can be obtained from intermediate amine II-1 through reaction with a carboxylic acid derivative III (L0=COOH) in the presence of an activating agent such as N,N'-dicyclohexylcarbodiimide or N-(3-dimethylaminopropyl)-N'-ethylcarbodiimide hydrochloride, with the optional addition of 1-hydroxybenzotriazole. Other suitable coupling agents may be used such as O-(7-azabenzotriazol-1-yl)-N,N,N',N'-tetramethyluronium hexafluorophosphate, 2-ethoxy-1-ethoxycarbonyl-1,2-dihydroquinoline, carbonyldiimidazole or diethylphosphorylcyanide. Optionally, a base like triethylamine, N,N-diisopropylethylamine or pyridine can be added to perform the coupling. The peptidic coupling is conducted at a temperature between −20° C. and 100° C., in an inert solvent, preferably a dry aprotic solvent like dichloromethane, acetonitrile, N,N-dimethylformamide and chloroform. Alternatively, the carboxylic acid can be activated by conversion into its corresponding acid chloride (by reaction with oxalyl chloride or thionyl chloride) or its corresponding activated ester, such as the N-hydroxysuccinimidyl ester (Org. Process Res. & Dev., 2002, 863) or the benzothiazolyl thioester (J. Antibiotics, 2000, 1071). The generated activated entity can react at a temperature between −20° C. and 100° C. with compound of formula II-1 in an aprotic solvent like dichloromethane, chloroform, acetonitrile, N,N-dimethylformamide and tetrahydrofuran to generate compound of formula I-1. Optionally, a base like triethylamine, N,N-diisopropylethylamine, pyridine, sodium hydroxide, sodium carbonate or potassium carbonate can be added to perform the coupling.

In Scheme 1, coupling of compounds of general formulae IV and V-1, followed by a deprotection step and finally introduction of the A4-G substituent allows the generation of compounds of formula I-1. Alternatively, the protecting group PG1 of compounds of formula V-1 can be removed according to the methods described above and the product of this reaction can then be reacted with one of the compounds of formula III as defined above. Subsequently, these intermediates are converted into compounds of formula I-1 following the methods described above for the synthesis of compounds of formula VI-1.

In Scheme 2, all the symbols have the same meaning as in formula I or in Scheme 1.

Reduction of nitro compounds of formula VI-2 to generate amino compounds of formula II-2 is performed using standard methods. Typical reducing agents which can be used for such reaction are an alkali metal hydride such as lithium aluminium hydride or sodium borohydride in presence of cobalt(II) chloride or nickel(II) chloride, or a metal such as iron or zinc in acidic medium such as hydrochloric acid or acetic acid. Alternatively, the nitro group can be reduced to the amine by hydrogenation over a noble metal catalyst such as palladium on activated carbon, Raney nickel or platinum oxide. The catalytic hydrogenation reaction can be carried out in a solvent such as ethanol, methanol or ethyl acetate at ambient temperature. In addition further reagents such as aluminium amalgam or ferrous sulphate may also be used for the nitro group reduction.

Scheme 2

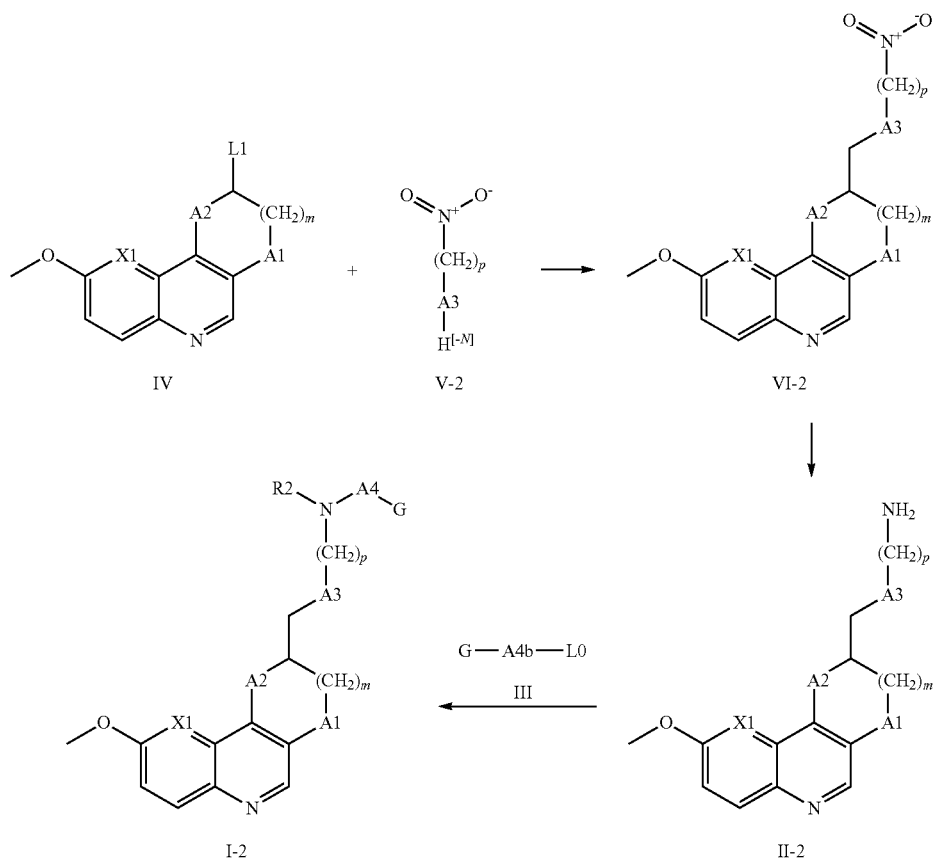

In Scheme 2, for all the other steps the methods described above with Scheme 1 can be followed for the preparation of compounds of formula I-2.

Alternatively and as in the case of Scheme 1, the nitro group of compounds of formula V-2 can be reduced according to the methods described above and the product of this reaction can then be reacted with one of the compounds of formula III as defined above. Subsequently, these intermediates are converted into compounds of formula I-2 following the methods described above for the synthesis of compounds of formula VI-2.

The compounds of formula I wherein A1 represents —O—, A2 is —CH$_2$— and m is 0 can be obtained as summarized in Scheme 3 hereafter.

Scheme 3

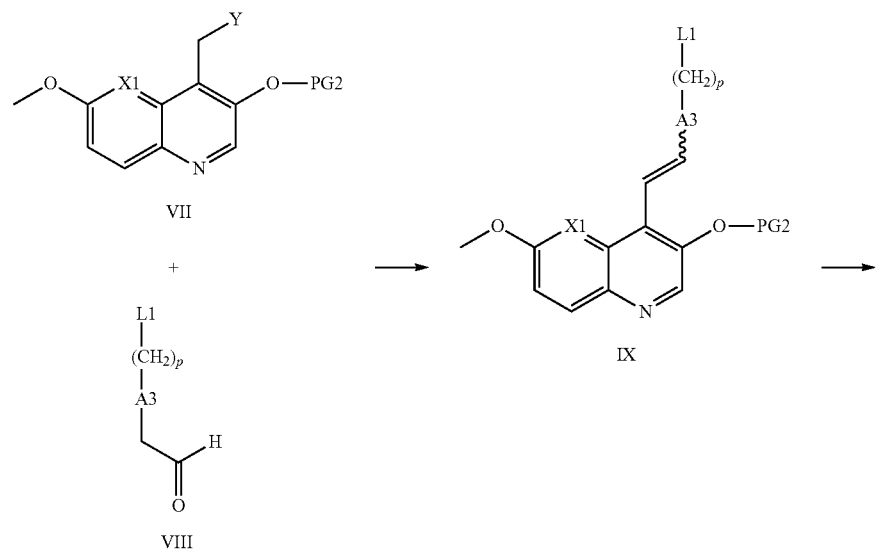

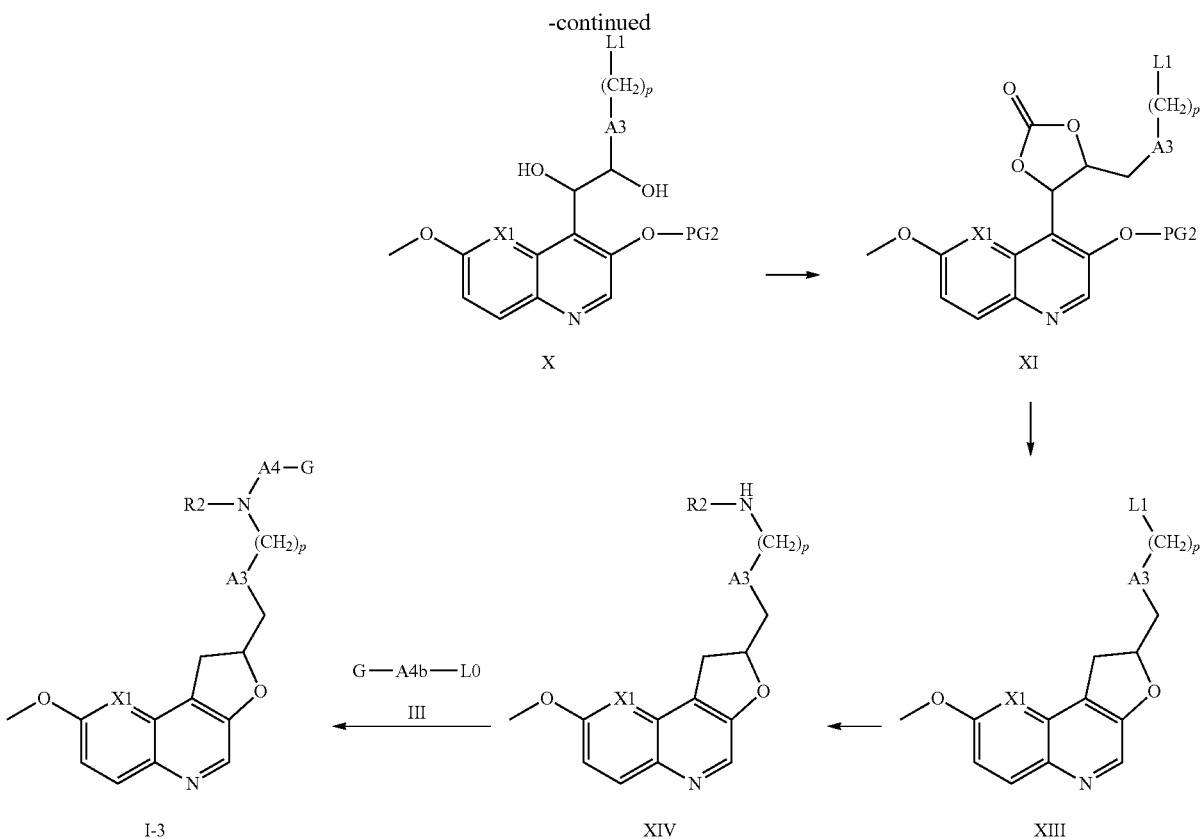

In Scheme 3, Y is a phosphonium salt or a phosphonate, PG2 is a phenol protecting group (such as benzyl, allyl, tetrahydropyranyl, tert-butyl dimethylsilyl) and all the other symbols are as defined above.

Protection of the phenol group is carried out under standard conditions to generate compounds of formula VII. For example the benzyl or the allyl groups are introduced with an alkaline solution of benzyl or allyl halide, respectively; the tetrahydropyranyl group is introduced with dihydropyran under acidic conditions; the hydroxyl groups are protected as silyl ethers by reacting with the required silyl chloride reagent in presence of a base such as imidazole or pyridine. Further general methods to introduce hydroxyl protecting groups have been described in *Protective Groups in Organic Synthesis*, 3$^{rd}$ Edition, by T. W. Greene and P. G. M. Wuts, published by John Wiley & Sons, 1999.

Compounds of formula IX are usually obtained from compounds of formula VII and aldehydes of formula VIII via a Wittig or Wittig-Horner reaction. For the Wittig reaction, the required phosphonium salt of formula VII is treated in a solvent such as water with an inorganic base such as sodium hydroxide. The corresponding phosphorane is collected by filtration and dried in vacuo. It is reacted with the required aldehyde of formula VIII in an aprotic solvent such as tetrahydrofuran, dichloromethane or toluene between 0° C. and 90° C. Alternatively the Wittig-Horner variant of the reaction can be used wherein the phosphonate of formula VII (generated from the corresponding bromide and triethylphosphite) is reacted with the aldehyde of formula VIII in presence of a base such as sodium hydride or sodium methylate in a solvent such as diethyl ether or tetrahydrofuran between 0° C. and 50° C.

Diols of formula X are obtained by dihydroxylation of the corresponding alkenyl derivatives of formula IX using a catalytic amount of osmium tetroxide or potassium osmate in the presence of a co-oxidant such as N-methylmorpholine-N-oxide in aqueous solvent such as an acetone-water or dichloromethane-water mixture between 0° C. and 30° C. (Chemical Reviews, 1995, 95, 1761).

Diols of formula X are further converted into compounds of formula XI by reaction with phosgene, diphosgene or triphosgene. This reaction is preferably carried out in a dry aprotic solvent such as tetrahydrofuran, dichloromethane or toluene in presence of an organic base such as triethylamine, pyridine, N,N-diisopropylethylamine or 4-dimethylaminopyridine and at a temperature between −78° C. and 40° C. Alternatively diols of formula X can also react with N,N'-carbonyldiimidazole or N,N'-disuccinimidyl carbonate in a dry aprotic solvent such as tetrahydrofuran, dichloromethane or toluene in absence or presence of an organic base such as triethylamine, pyridine, N,N-diisopropylethylamine or 4-dimethylaminopyridine and at a temperature between −30° C. and 80° C.

Conversion of compounds of formula XI into compounds of formula XII is performed by hydrogenolysis over a noble metal catalyst (e.g. palladium or palladium hydroxide on activated carbon; Chem. Eur. J., 1999, 5, 1055). In case the phenol protecting group PG2 is a benzyl group, this one is also removed in these conditions to directly get compounds of formula XII. In other cases, the phenol protecting groups PG2 are further removed following standard conditions to generate compounds of formula XII. For example the allyl group is removed in presence of a palladium salt such as palladium acetate or tetrakis(triphenylphosphine)palladium(0) and an allyl cation scavenger such as morpholine, pyrrolidine, dimedone or tributylstannane between 0° C. and 70° C. in a solvent such as tetrahydrofuran; the tetrahydropyranyl group is removed in presence of aqueous oxalic acid between 50° C. and 90° C. in a solvent such as methanol; the tert-butyl dimethylsilyl group is removed either using fluoride anion sources such as tetra-n-butylammonium fluoride in a solvent such as tetrahydrofuran or N,N-dimethylformamide or in hydrofluoric acid in acetonitrile between 0° C. and 40° C. Further general methods to remove phenol protecting groups have been described in *Protective Groups in Organic Synthesis*, 3$^{rd}$ Edition, by T. W. Greene and P. G. M. Wuts, published by John Wiley & Sons, 1999.

Compounds of formula XIII can be obtained from compounds of formula XII via a Mitsunobu coupling (as reviewed by O. Mitsunobu, Synthesis, 1981, 1). The reaction is for example performed in the presence of diethyl or diisopropyl azodicarboxylate and triphenylphosphine, in a wide range of solvents such as N,N-dimethylformamide, tetrahydrofuran, 1,2-dimethoxyethane or dichloromethane and within a wide range of temperatures (between −20° C. and 60° C.). The reaction might also be performed using polymer-supported triphenylphosphine.

In Scheme 3, for all the other steps the methods described above for Schemes 1 and 2 can be followed for the preparation of compounds of formula I-3.

Alternatively and as in the case of Schemes 1 and 2, the protecting group PG1 or the nitro group of compounds of formula IX can be removed or reduced, respectively, according to the methods described above and the products of this reaction can then be reacted with one of the compounds of formula III as defined above. Subsequently, these intermediates are converted into compounds of formula I-3 following the methods described above for the synthesis of compounds of formulae X, XI, XII and XIII.

The compounds of formula I wherein A1 represents —O—, A2 is —CH$_2$— and m is 1 can be obtained as summarized in Scheme 4 hereafter.

Scheme 4

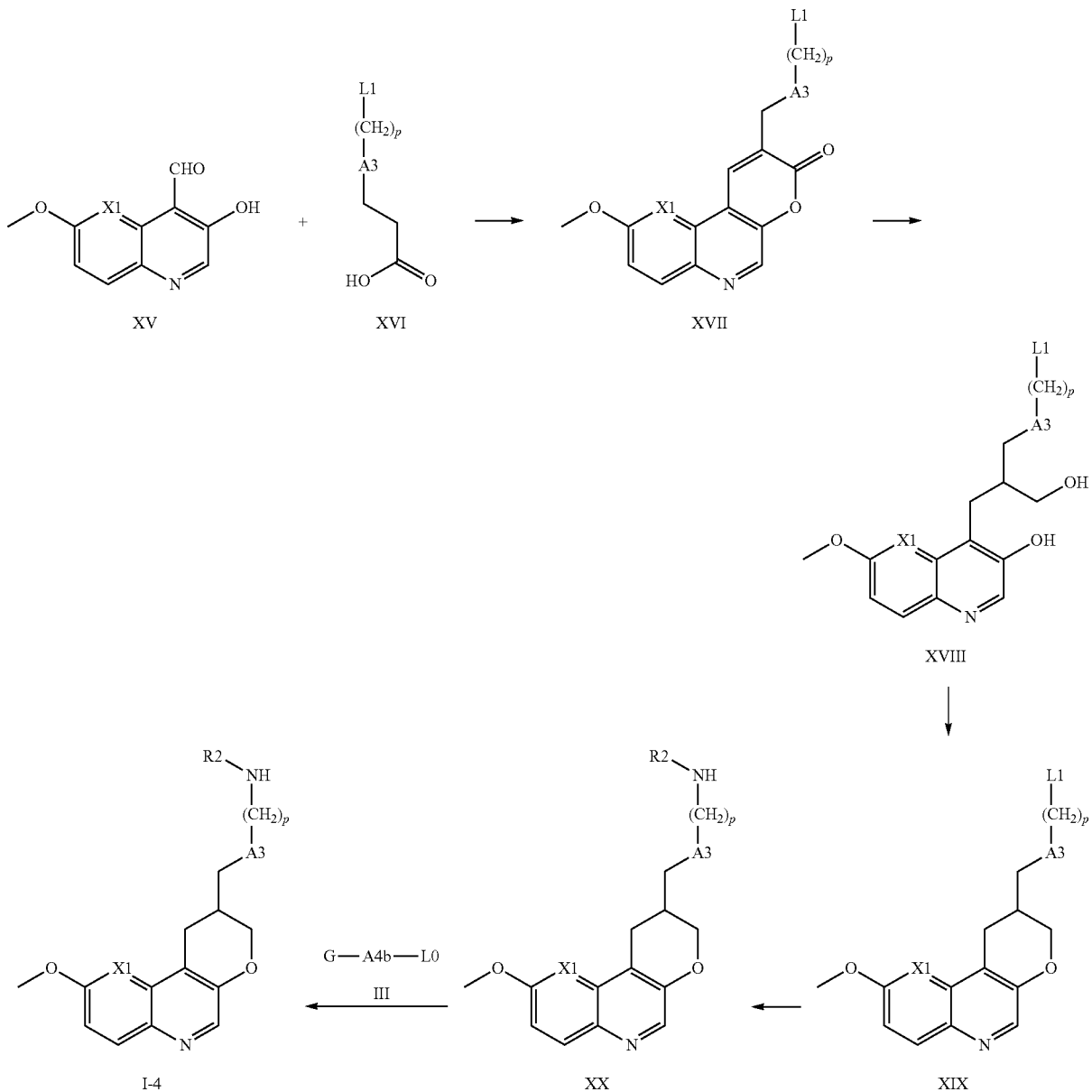

In Scheme 4, all the symbols are as defined above.

Coupling of compounds of general formulae XV and XVI allows the generation of compounds of formula XVII. The reaction takes place in presence of a coupling agent such as O-(7-azabenzotriazol-1-yl)-N,N,N',N'-tetramethyluronium hexafluorophosphate and a base like triethylamine, N,N-diisopropylethylamine or 1,8-diazabicyclo[5,4,0]undec-7-ene. The coupling is conducted at a temperature between −20° C. and 100° C., in an inert solvent, preferably a dry aprotic solvent like dichloromethane, acetonitrile or N,N-dimethylformamide.

Esters of formula XVII are further reduced to generate compounds of formula XVIII. Reduction is performed with a reducing agent like boron or aluminium hydride reducing agent such as lithium aluminium hydride, lithium borohydride, sodium borohydride in a solvent such as tetrahydrofuran between −20° C. and 80° C. Alternatively, the ester function is hydrolyzed into its corresponding acid using an alkali hydroxide such as sodium hydroxide, potassium hydroxide or lithium hydroxide in water or in a mixture of water with polar protic or aprotic organic solvents such as dioxane, tetrahydrofuran or methanol between −10° C. and 80° C. The resulting carboxylic acid is further reduced into the corresponding alcohol using a borane derivative such as borane-tetrahydrofuran complex in a solvent such as tetrahydrofuran between −10° C. and 80° C.

Compounds of formula XIX can be obtained from compounds of formula XVIII via a Mitsunobu coupling following methods previously described for the preparation of compounds of formula XIII.

In Scheme 4, for all the other steps the methods described above for Schemes 1 and 2 can be followed for the preparation of compounds of formula I-4.

Alternatively and as in the case of Schemes 1 and 2, the protecting group PG1 or the nitro group of compounds of formula XVII can be removed or reduced, respectively, according to the methods described above and the products of this reaction can then be reacted with one of the compounds of formula III as defined above. Subsequently, these intermediates are converted into compounds of formula I-4 following the methods described above for the synthesis of compounds of formulae XVIII and XIX.

The compounds of formula I wherein A1 is —O—, A2 is —CH$_2$—, m is 0 and —(CH$_2$)$_n$— is substituted can be obtained as summarized in Scheme 5.

In Scheme 5, PG2 is a phenol protecting group (such as benzyl, allyl, tetrahydropyranyl, tert-butyl dimethylsilyl), PG3 is a hydroxyl protecting group (such as benzyl, acetyl, tetrahydropyranyl, trimethylsilyl, tert-butyl dimethylsilyl) and all the other symbols are as defined above.

Coupling of alkynes of formula XXI and aldehydes of formula VIII is carried out in presence of trimethylsilyl trifluoromethanesulfonate with a base such as N,N-diisopropylethylamine and a catalytic amount of zinc acetylide in a solvent such as diethyl ether (J. Org. Chem., 2009, 74, 2904). Alternatively, coupling can be performed in presence of a strong base such as n-butyllithium or lithium diisopropylamide in a solvent such as diethyl ether or tetrahydrofuran between −78° C. and 30° C.

Scheme 5
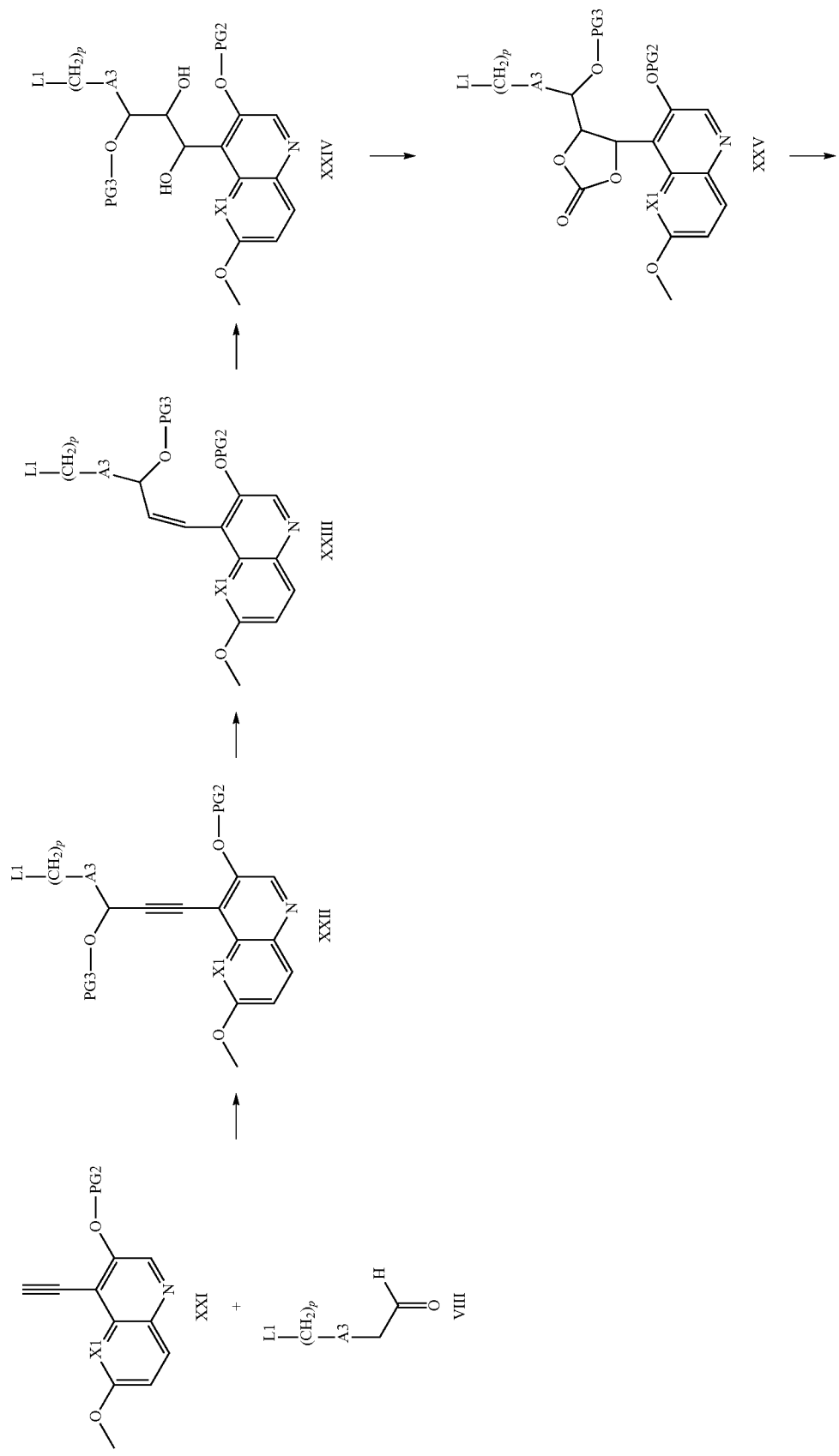

-continued
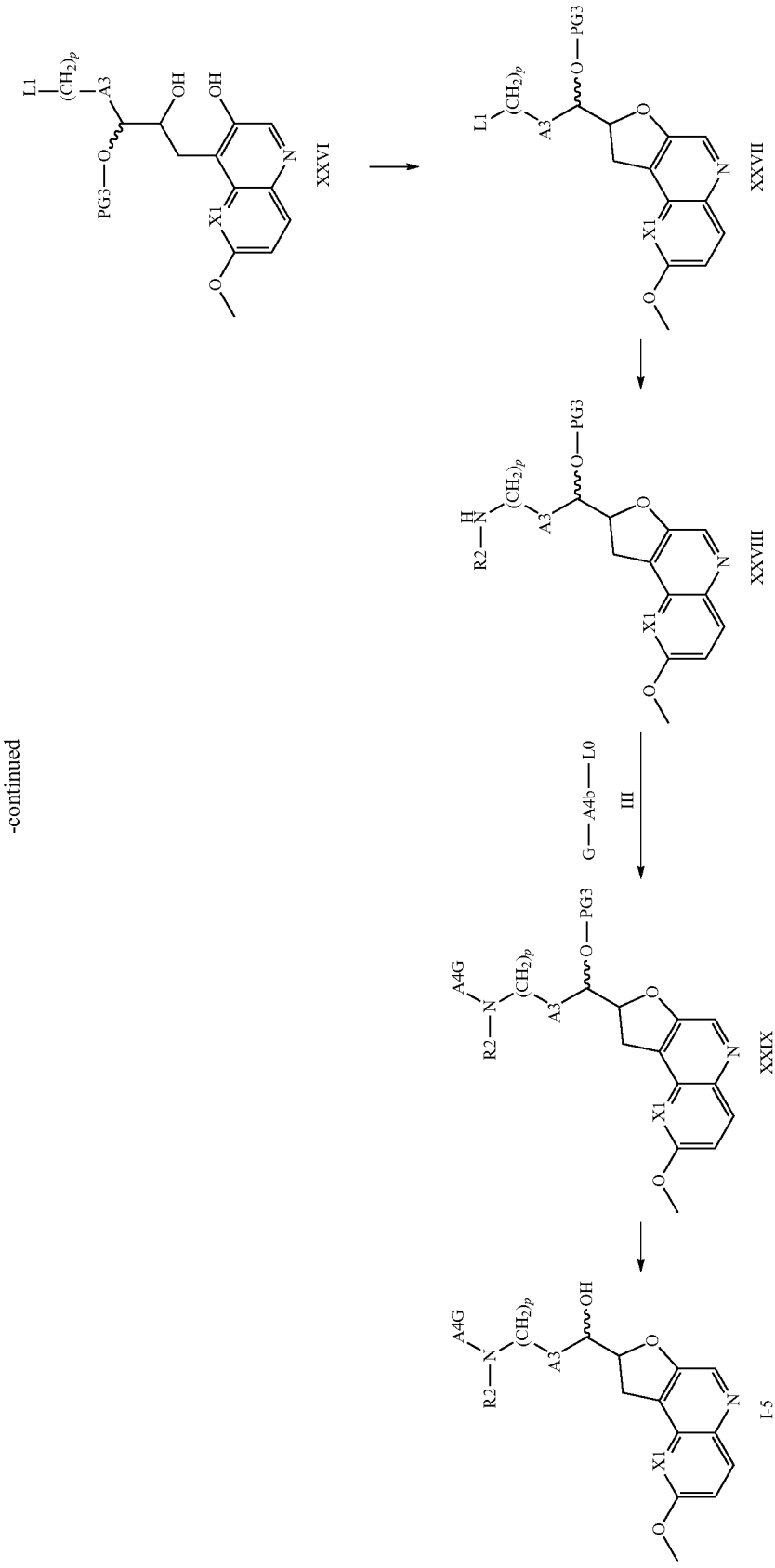

Protection of the generated hydroxyl group is carried out under standard conditions to generate compounds of formula XXII. For example the benzyl group is introduced with benzyl bromide in presence of a base such as sodium hydride, in absence or presence of silver(I) oxide or tetra-n-butylammonium iodide in a solvent such as dichloromethane, tetrahydrofuran or N,N-dimethylformamide; the acetyl group is introduced with acetic anhydride in pyridine; the tetrahydropyranyl group is introduced with dihydropyran in presence of para-toluenesulfonic acid or pyridinium para-toluenesulfonate in a solvent such as dichloromethane; the hydroxyl groups are protected as silyl ethers by reacting with the required silyl chloride reagent in presence of a base such as imidazole or triethylamine in a solvent such as dichloromethane, tetrahydrofuran or N,N-dimethylformamide between 10 and 40° C. Further general methods to introduce hydroxyl protecting groups have been described in *Protective Groups in Organic Synthesis*, 3$^{rd}$ Edition, by T. W. Greene and P. G. M. Wuts, published by John Wiley & Sons, 1999.

Hydrogenation of compounds of formula XXII in presence of Lindlar catalyst allows the generation of cis-alkenes of formula XXIII.

At that stage, compounds of formula XXVII are generated following methods previously described in Scheme 3 for the preparation of compounds of formula XIII.

Further conversion of compounds of formula XXVII into compounds of formula XXIX is performed following methods described above in Schemes 1 and 2 for the preparation of compounds of formulae I-1 and I-2.

Final removal of the hydroxyl protecting group PG3 of compounds of formula XXIX is carried out under standard conditions to generate compounds of formula I-5. For example the benzyl group is removed by hydrogenolysis over a noble metal catalyst (e.g. palladium or palladium hydroxide on activated carbon); the acetyl group is removed in presence of a base such as potassium carbonate in a solvent such as methanol-water; the tetrahydropyranyl group is removed in presence of para-toluenesulfonic acid with a pH of 3, between 40° C. and 70° C. in a solvent such as methanol; the silyl ether groups are removed either using fluoride anion sources such as tetra-n-butylammonium fluoride in a solvent such as tetrahydrofuran or N,N-dimethylformamide between 0° C. and 40° C. or in hydrofluoric acid in acetonitrile between 0° C. and 40° C. or using acidic conditions such as acetic acid in tetrahydrofuran-methanol or hydrochloric acid in methanol. Further general methods to remove hydroxyl protecting groups have been described in *Protective Groups in Organic Synthesis*, 3$^{rd}$ Edition, by T. W. Greene and P. G. M. Wuts, published by John Wiley & Sons, 1999.

Alternatively and as in the case of Schemes 1 and 2, the protecting group PG1 or the nitro group of compounds of formula XXIII can be removed or reduced, respectively, according to the methods described above and the products of this reaction can then be reacted with one of the compounds of formula III as defined above. Subsequently, these intermediates are converted into compounds of formula I-5 following the methods described above for the synthesis of compounds of formulae XXIV, XXV, XXVI, XXVII and I-5.

Unless otherwise stated the required starting compounds of formula IV, VII, XV and XXI are prepared following or adapting procedures described in the scientific literature, such as J. Org. Chem., 1953, 18(5), p. 552; J. Med. Chem., 1988, 31(3), p. 688; Synthesis, 2004, 1, p. 121; Organic Synthesis Coll., 1960, vol. 40, p. 54; PCT Pub. No. WO93/20055, WO2005/004808.

Unless otherwise stated the required starting derivatives of formula V, VIII and XVI are commercially available or are prepared following or adapting synthetic procedures described in the scientific literature, such as J. Med. Chem., 2007, 50(15), p. 3561; PCT Pub. No. WO2009/012647, WO2008/003690, WO2005/077932, US2005/0101644, Unless otherwise stated compounds of formula III-1, III-2 and III-3 are commercially available or may be obtained by procedures described in the patent literature, such as PCT Pub. No. WO2007/093507, WO2007/052843, WO2006/105289, WO2006/038734, WO2006/021448, WO2004/058144, WO2004/002992, WO2002/034754.

When an optically active form of a compound of the invention is required, it may be obtained by carrying out one of the above procedures using a pure enantiomer or diastereomer as a starting material, or by resolution of a mixture of the enantiomers or diastereomers of the final product or intermediate using a standard procedure. The resolution of enantiomers may be achieved by chromatography on a chiral stationary phase, such as REGIS PIRKLE COVALENT (R-R) WHELK-02, 10 μm, 100 Å, 250×21.1 mm column. Alternatively, resolution of stereoisomers may be obtained by preparation and selective crystallization of a diastereomeric salt of a chiral intermediate or chiral product with a chiral acid, such as camphorsulfonic acid. Alternatively a method of stereoselective synthesis may be employed, for example by using a chiral variant of a protecting group, a chiral catalyst or a chiral reagent where appropriate in the reaction sequence.

Enzymatic techniques may also be used for the preparation of optically active compounds and/or intermediates.

Further aspects of the invention include
pharmaceutical compositions comprising a compound of formula I or a pharmaceutically acceptable salt, a hydrate or solvate thereof and a pharmaceutically acceptable carrier;
the compounds of formula I or a pharmaceutically acceptable salt, a hydrate or solvate thereof for use as a medicament, in particular a medicament for the treatment of bacterial infections; and
the use of a compound of formula I or a pharmaceutically acceptable salt, a hydrate or solvate thereof for the preparation of medicaments for the treatment of infectious diseases caused by bacteria.

All listed compounds shown in Table 1 below are particularly advantageous for the treatment of infections by *Staphylococcus aureus* and/or *Staphylococcus epidermidis* and exhibit a MIC≤8 mg/L for at least one of the strains.

The compounds of number 1-7, 10, 12, 14-16, 19, 23, 24, 27-34, 36-45, 47, 49-56, 58-61, 64, 66, 68-71, 73-75 shown in Table 1 below are particularly advantageous for the treatment of infections by *Staphylococcus aureus* and/or *Staphylococcus epidermidis* and/or *Streptococcus pneumoniae* and exhibit a MIC for said strains of generally ≤8 mg/L.

The compounds of number 1-4, 6, 12, 24; 29, 30, 32, 38, 66 shown in Table 1 below are particularly advantageous for the treatment of infections by *Staphylococcus aureus* and/or *Staphylococcus epidermidis* and/or *Streptococcus pneumoniae* and/or *Escherichia coli* and exhibit a MIC for said strains of generally ≤8 mg/L.

In general, compounds of formula I are administered either individually, or optionally also in combination with another desired therapeutic agent, using the known and acceptable methods. Such therapeutically useful agents may be administered, for example, by one of the following routes: orally, for example in the form of dragees, coated tablets, pills, semi-solid substances, soft or hard capsules, solutions, emulsions or suspensions; parenterally, for example in the form of an injectable solution; rectally in the form of suppositories; by inhalation, for example in the form of a powder formulation or a spray; transdermally or intranasally.

For the preparation of such tablets, pills, semi-solid substances, coated tablets, dragees and hard gelatine capsules, the therapeutically usable product may be mixed with pharmacologically inert, inorganic or organic pharmaceutical carrier substances, for example with lactose, sucrose, glucose, gelatine, malt, silica gel, starch or derivatives thereof, talcum, stearic acid or salts thereof, skimmed milk powder, and the like. For the preparation of soft capsules, pharmaceutical carrier substances such as, for example, vegetable oils, petroleum, animal or synthetic oils, wax, fat and polyols may be used.

For the preparation of liquid solutions and syrups, pharmaceutical carrier substances such as, for example, water, alcohols, aqueous saline solution, aqueous dextrose solution, polyols, glycerol, vegetable oils, petroleum and animal or synthetic oils may be used.

For suppositories, pharmaceutical carrier substances such as, for example, vegetable oils, petroleum, animal or synthetic oils, wax, fat and polyols may be used.

For aerosol formulations, compressed gases that are suitable for this purpose, such as, for example, oxygen, nitrogen and carbon dioxide may be used. The pharmaceutically acceptable agents may also comprise additives for preserving and stabilising, emulsifiers, sweeteners, flavourings, salts for altering the osmotic pressure, buffers, encapsulation additives and antioxidants.

Combinations with other therapeutic agents which are also encompassed by the present invention may comprise one, two or more other antimicrobial and anti-fungal active ingredients.

For the prevention and/or treatment of bacterial infections, the dose of the biologically active compound according to the invention may vary within wide limits and may be adjusted to individual requirements. Generally, a dose of 10 mg to 4000 mg per day is suitable, a preferred dose being from 50 to 3 000 mg per day. In suitable cases, the dose may also be below or above the stated values. The daily dose may be administered as a single dose or in multiple doses. A typical individual dose contains approximately 50 mg, 100 mg, 250 mg, 500 mg, 1 g or 2 g of the active ingredient.

EXAMPLES

Particular embodiments of the invention are described in the following Examples, which serve to illustrate the invention in more detail:

All reagents and solvents are generally used as received from the commercial supplier; reactions are routinely performed with anhydrous solvents in well-dried glassware under an argon or nitrogen atmosphere;

evaporations are carried out by rotary evaporation under reduced pressure and work-up procedures are carried out after removal of residual solids by filtration;

all temperatures are given in ° C.; unless otherwise noted, operations are carried out at room temperature, that is typically in the range 18-25° C.;

column chromatography (by the flash procedure) is used to purify compounds and is performed using Merck silica gel 60 (70-230 mesh ASTM) unless otherwise stated;

in general, the course of reactions is followed by TLC, HPLC, or LC/MS and reaction times are given for illustration only; yields are given for illustration only and are not necessarily the maximum attainable;

the structure of the final products of the invention is generally confirmed by NMR and mass spectral techniques. Proton NMR spectra are recorded on a Brucker 400 MHz spectrometer. Chemical shifts (δ) are reported in ppm relative to $Me_4Si$ as internal standard, and J values are in Hertz (Hz). Each peak is denoted as a broad singlet (br), singlet (s), doublet (d), doublet of doublets (dd), triplet of doublets (td) or multiplet (m). Mass spectra are generated using a q-T of Ultima (Waters AG) mass spectrometer in the positive ESI mode. The system is equipped with the standard Lockspray interface;

each intermediate is purified to the standard required for the subsequent stage and is characterized in sufficient detail to confirm that the assigned structure is correct;

analytical and preparative HPLC on non-chiral phases are performed using RP-C18 based columns;

the following abbreviations may be used:
Acetone-$d_6$: Deuterated acetone
$CDCl_3$: Deuterated chloroform
DMSO-$d_6$: Deuterated dimethyl sulphoxide
ELSD: Evaporative light scattering detection
HPLC: High performance liquid chromatography
J: Coupling constant
LC/MS: Liquid chromatography coupled to mass spectoscopy
$CD_3OD$: Deuterated methanol
$Me_4Si$: Tetramethylsilane
MS: Mass spectroscopy
NMR: Nuclear magnetic resonance
TLC: Thin layer chromatography The following Examples refer to the compounds of formula I as indicated in Table 1:

TABLE 1

Exemplified compounds

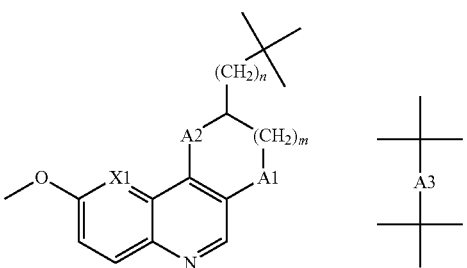

| N° | | | | | p | R2 | A4 | G |
|---|---|---|---|---|---|---|---|---|
| 1 | 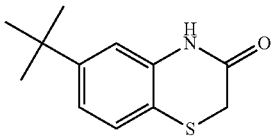 | | 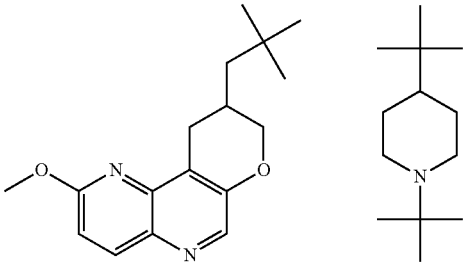 | | 0 | H | C=O | 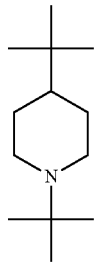 |

TABLE 1-continued

Exemplified compounds

| N° | structure | A3 | p | R2 | A4 | G |
|---|---|---|---|---|---|---|
| 2 | | piperidine | 0 | H | C=O | 6-tert-butyl-pyrido[3,2-b][1,4]oxazin-3(4H)-one |
| 3 | | piperidine | 0 | H | C=O | 6-tert-butyl-benzo[1,4]oxazin-3(4H)-one |
| 4 | | piperidine | 0 | H | C=O | 6-tert-butyl-pyrido[3,2-b][1,4]thiazin-3(4H)-one |
| 5 | | pyrrolidine | 0 | H | C=O | 6-tert-butyl-pyrido[3,2-b][1,4]oxazin-3(4H)-one |

TABLE 1-continued

Exemplified compounds

| N° | [structure with X1, A1, A2, (CH2)n, (CH2)m, OMe] | A3 | p | R2 | A4 | G |
|---|---|---|---|---|---|---|
| 6 | [methoxy-naphthyridine-pyran tBu structure] | [3-tBu-pyrrolidin-1-yl] | 0 | H | C=O | [6-tBu-4H-benzo[1,4]thiazin-3-one] |
| 7 | [methoxy-naphthyridine-pyran tBu structure] | [3-tBu-piperidin-1-yl] | 0 | H | C=O | [6-tBu-4H-benzo[1,4]thiazin-3-one] |
| 8 | [methoxy-naphthyridine-pyran tBu structure] | [4-tBu-piperidin-1-yl] | 0 | H | C=O | [6-tBu-2,3-dihydro-benzo[1,4]dioxine] |
| 9 | [methoxy-naphthyridine-pyran tBu structure] | [4-tBu-piperidin-1-yl] | 0 | H | C=O | [3-tBu-5-(thiophen-2-yl)isoxazole] |

TABLE 1-continued

Exemplified compounds

| N° | [structure with X1, A1, A2, (CH2)n, (CH2)m, OMe] | A3 | p | R2 | A4 | G |
|---|---|---|---|---|---|---|
| 10 | | 4-tert-butylpiperidinyl | 1 | H | C=O | 6-tert-butyl-2H-benzo[b][1,4]thiazin-3(4H)-one |
| 11 | | 3-tert-butylpiperidinyl | 1 | H | C=O | 6-tert-butyl-2H-benzo[b][1,4]thiazin-3(4H)-one |
| 12 | | 3-tert-butylazetidinyl | 0 | H | C=O | 6-tert-butyl-2H-benzo[b][1,4]thiazin-3(4H)-one |
| 13 | | trans-4-tert-butylcyclohexyl | 0 | H | C=O | 6-tert-butyl-2H-benzo[b][1,4]thiazin-3(4H)-one |

TABLE 1-continued

Exemplified compounds

TABLE 1-continued
Exemplified compounds
| N° | 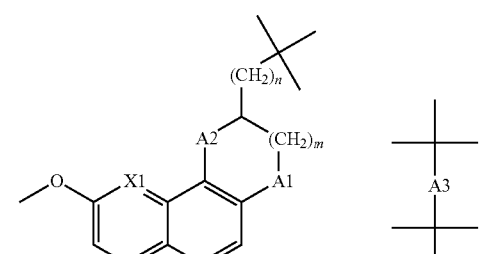 | A3 | p | R2 | A4 | G |
|---|---|---|---|---|---|---|
| 18 | 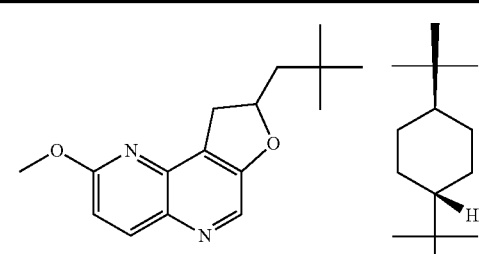 | 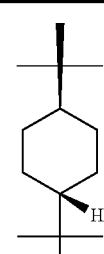 | 0 | H | —CH₂— | 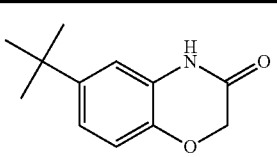 |
| 19 | 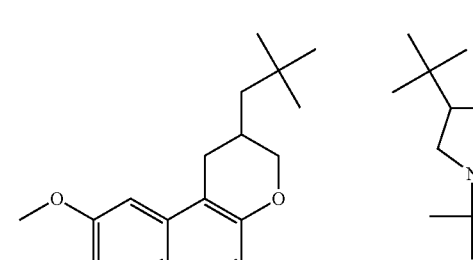 | 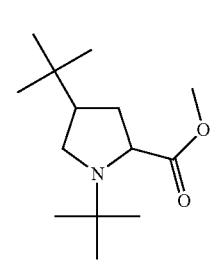 | 0 | H | C=O | 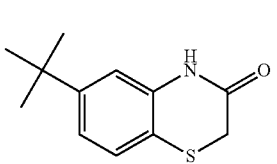 |
| 20 | 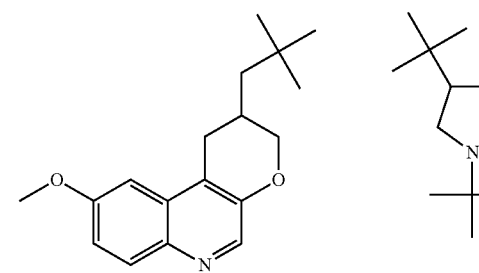 | 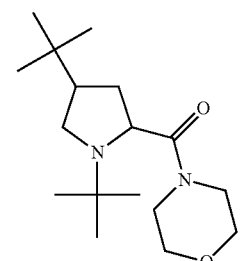 | 0 | H | C=O | 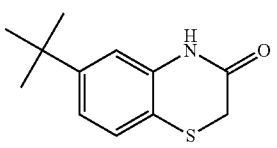 |
| 21 | 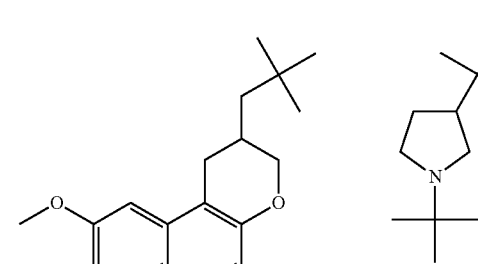 | 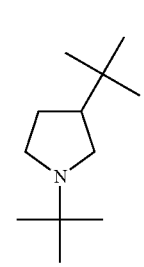 | 1 | H | C=O | 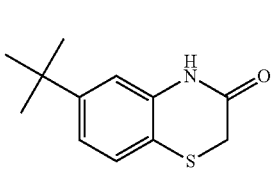 |

TABLE 1-continued
Exemplified compounds
| N° | [structure with X1, A1, A2, (CH2)n, (CH2)m, OMe] | A3 | p | R2 | A4 | G |
|---|---|---|---|---|---|---|
| 22 | 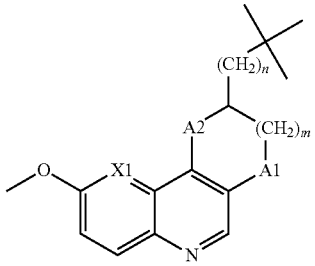 | 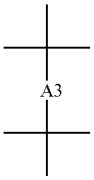 | 1 | H | C=O | 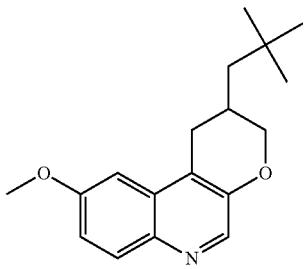 |
| 23 | 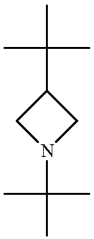 | 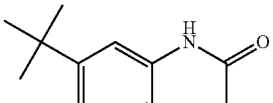 | 0 | H | C=O | 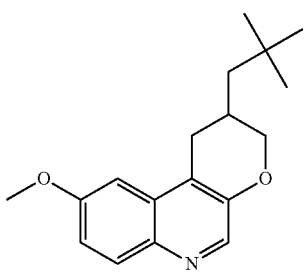 |
| 24 | 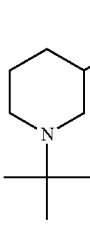 | 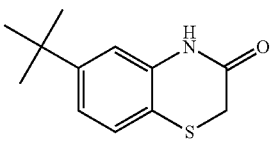 | 0 | H | C=O | 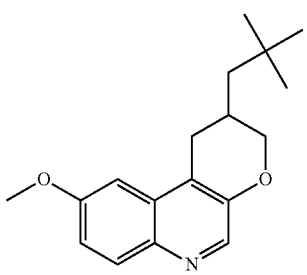 |
| 25 | 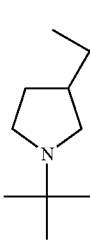 | 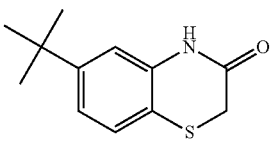 | 0 | H | C=O | 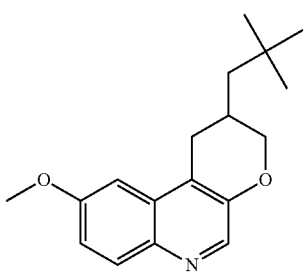 |

TABLE 1-continued

Exemplified compounds

| N° | [structure with X1, A1, A2, A3, (CH2)n, (CH2)m, OMe] | A3 | p | R2 | A4 | G |
|---|---|---|---|---|---|---|
| 26 | | | 1 | H | C=O | |
| 27 | | | 0 | H | C=O | |
| 28 | | | 0 | H | C=O | |
| 29 | | | 0 | H | C=O | |

TABLE 1-continued
Exemplified compounds
| N° | 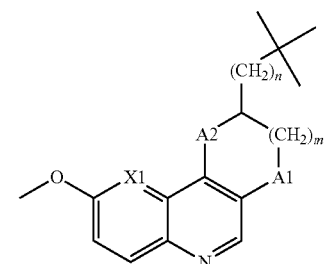 | A3 | p | R2 | A4 | G |
|---|---|---|---|---|---|---|
| 30 | 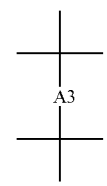 |  | 0 | H | C=O | 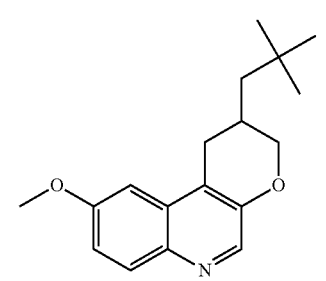 |
| 31 | 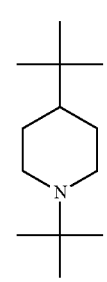 | 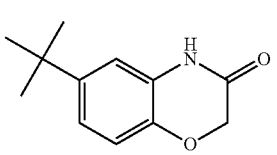 | 0 | H | C=O | 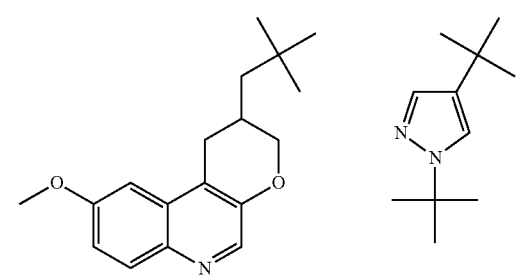 |
| 32 | 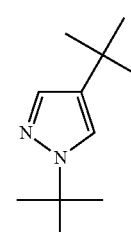 | 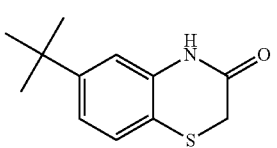 | 0 | H | —CH$_2$— | 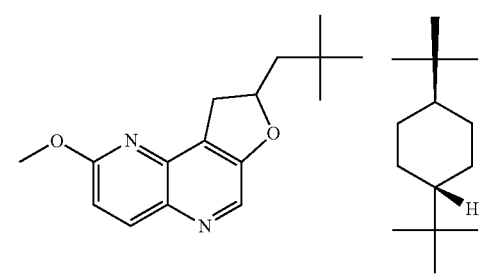 |
| 33 | 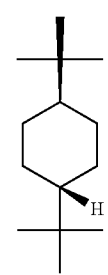 | 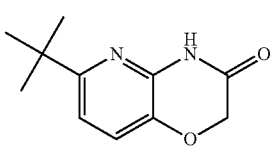 | 0 | H | —CH$_2$— | 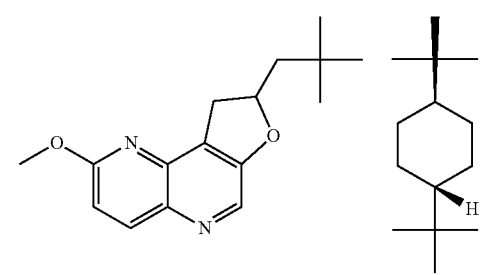 |

TABLE 1-continued

Exemplified compounds

| N° | [core structure with X1, A1, A2, (CH2)n, (CH2)m, OMe] | A3 | p | R2 | A4 | G |
|----|---|---|---|----|-----|---|
| 34 | 9-methoxy pyrano-quinoline | piperidine | 0 | H | —CH2— | 6-substituted benzo[1,4]thiazin-3(4H)-one |
| 35 | 9-methoxy pyrano-quinoline | piperidine | 0 | H | —CH2— | 6-substituted benzo[1,4]oxazin-3(4H)-one |
| 36 | 9-methoxy pyrano-quinoline | cyclohexane | 0 | H | C=O | 6-substituted benzo[1,4]oxazin-3(4H)-one |
| 37 | 9-methoxy pyrano-quinoline | piperidine | 0 | H | C=O | thieno[3,2-b]thiophene |

TABLE 1-continued
Exemplified compounds
| N° | (structure with X1, A1, A2, A3, (CH2)n, (CH2)m, OMe) | A3 | p | R2 | A4 | G |
|---|---|---|---|---|---|---|
| 38 |  | 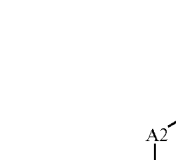 | 0 | H | C=O | 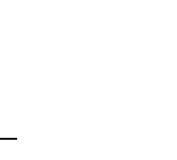 |
| 39 |  | 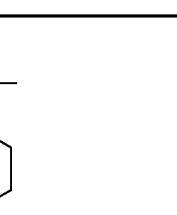 | 0 | H | C=O | 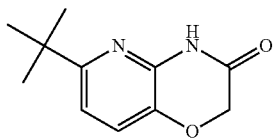 |
| 40 |  | 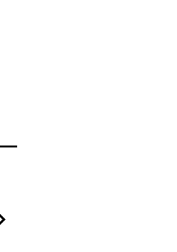 | 0 | H | C=O | 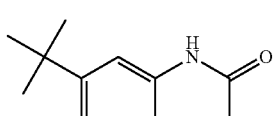 |
| 41 |  |  | 0 | H | C=O | 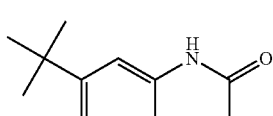 |

TABLE 1-continued

Exemplified compounds

| N° | [structure with (CH₂)ₙ, A2, (CH₂)ₘ, A1, X1, OMe] | [A3] | p | R2 | A4 | G |
|---|---|---|---|---|---|---|
| 42 | | | 0 | H | C=O | |
| 43 | | | 0 | H | C=O | |
| 44 | | | 0 | H | C=O | |
| 45 | | | 0 | H | C=O | |
| 46 | | | 0 | H | C=O | |

TABLE 1-continued

Exemplified compounds

| N° | [structure with X1, A1, A2, A3, (CH₂)n, (CH₂)m, methoxy] | A3 | p | R2 | A4 | G |
|---|---|---|---|---|---|---|
| 47 | [10-fluoro-9-methoxy pyrano-quinoline with neopentyl] | [azetidine with tBu] | 0 | H | C=O | [6-tert-butyl-benzothiazin-3-one] |
| 48 | [methoxy-naphthyridine pyran with neopentyl] | [1-tBu-4-tBu-pyrazole] | 0 | H | C=O | [6-tert-butyl-benzothiazin-3-one] |
| 49 | [methoxy-thiopyrano-quinoline with neopentyl] | [azetidine with tBu] | 0 | H | C=O | [6-tert-butyl-benzothiazin-3-one] |
| 50 | [methoxy-thiopyrano-quinoline with neopentyl] | [1-tBu-3-tBu-pyrrolidine] | 0 | H | C=O | [6-tert-butyl-benzothiazin-3-one] |

TABLE 1-continued

Exemplified compounds

| N° | (structure with X1, A1, A2, A3, (CH2)n, (CH2)m, OMe) | | p | R2 | A4 | G |
|---|---|---|---|---|---|---|
| 51 | 9-methoxy thiopyrano-quinoline with neopentyl | 4-tert-butyl-pyrrolidin-2-yl-methanol (N-tBu) | 0 | H | C=O | 6-tert-butyl-2H-1,4-benzothiazin-3(4H)-one |
| 52 | 9-methoxy thiopyrano-quinoline with neopentyl | 4-tert-butyl-1-tert-butyl-piperidine | 0 | H | C=O | 6-tert-butyl-2H-1,4-benzothiazin-3(4H)-one |
| 53 | 9-methoxy thiopyrano-quinoline with neopentyl | 3-tert-butyl-1-tert-butyl-pyrrolidine | 1 | H | C=O | 6-tert-butyl-2H-1,4-benzothiazin-3(4H)-one |
| 54 | methoxy furano-naphthyridine with neopentyl | 4-tert-butyl-1-tert-butyl-piperidine | 0 | H | C=O | 6-tert-butyl-2H-1,4-benzothiazin-3(4H)-one |

TABLE 1-continued

Exemplified compounds

TABLE 1-continued

Exemplified compounds

| N° | [structure] | | p | R2 | A4 | G |
|---|---|---|---|---|---|---|
| 60 | | | 0 | H | C=O | |
| 61 | | | 0 | H | C=O | |
| 62 | | | 0 | H | —CH₂— | |
| 63 | | | 0 | H | C=O | |
| 64 | | | 0 | H | C=O | |

TABLE 1-continued

Exemplified compounds

| N° | [structure with (CH2)n, A2, X1, A1, (CH2)m, OMe, A3] | | p | R2 | A4 | G | |
|---|---|---|---|---|---|---|---|
| 65 | [fluoro-methoxy pyrano-quinoline with neopentyl] | [azetidine with t-Bu] | 0 | H | C=O | [6-tert-butyl-benzoxazin-3-one] |
| 66 | [methoxy furo-naphthyridine with neopentyl] | [piperidine with t-Bu] | 0 | H | C=O | [6-tert-butyl-benzoxazin-3-one] |
| 67 | [fluoro-methoxy pyrano-quinoline with neopentyl] | [imidazole with t-Bu] | 0 | H | C=O | [6-tert-butyl-benzothiazin-3-one] |
| 68 | [methoxy pyrano-quinoline with neopentyl] | [pyrazole with t-Bu and CH2OH] | 0 | H | C=O | [6-tert-butyl-benzothiazin-3-one] |

TABLE 1-continued

Exemplified compounds

| N° | | | p | R2 | A4 | G |
|---|---|---|---|---|---|---|
| 69 | | | 0 | H | C=O | |
| 70 | | | 0 | H | C=O | |
| 71 | | | 0 | H | C=O | |
| 72 | | | 0 | H | —CH₂— | |

TABLE 1-continued

Exemplified compounds

| N° | [structure with X1, A2, A1, (CH2)n, (CH2)m, OMe] | A3 | p | R2 | A4 | G |
|---|---|---|---|---|---|---|
| 73 | 9-methoxy pyrano[3,4-c]quinoline with neopentyl substituent | 1-tert-butyl-5-methyl-4-tert-butyl-pyrazole | 0 | H | —CH₂— | 6-tert-butyl-2H-1,4-benzothiazin-3(4H)-one |
| 74 | methoxy-naphthyridine pyrano fused with neopentyl | 1-tert-butyl-3-methyl-4-tert-butyl-pyrazole | 0 | H | C=O | 6-tert-butyl-2H-1,4-benzothiazin-3(4H)-one |
| 75 | methoxy-naphthyridine pyrano fused with neopentyl | 1-tert-butyl-4-tert-butyl-5-methyl-pyrazole | 0 | H | C=O | 6-tert-butyl-2H-1,4-benzothiazin-3(4H)-one |
| 76 | methoxy furo[3,4-c]quinoline with (S)-hydroxy-tert-butyl stereochemistry | trans-1,4-di-tert-butylcyclohexane | 0 | H | C=O | 6-tert-butyl-pyrido[3,2-b][1,4]oxazin-3(4H)-one |

TABLE 1-continued

Exemplified compounds

| N° | [structure with (CH₂)ₙ, A2, X1, OMe, A1, (CH₂)ₘ, N] | A3 | p | R2 | A4 | G |
|---|---|---|---|---|---|---|
| 77 | [fluoro-methoxy furoquinoline structure] | [tetrahydropyran with H] | 0 | H | C=O | [tert-butyl benzothiazinone structure] |
| 78 | [fluoro-methoxy furoquinoline structure] | [tetrahydropyran with H] | 0 | H | —CH₂— | [tert-butyl benzothiazinone structure] |

The numbers of the compounds of formula I used in the leftmost column of Table 1 are used in the whole application text for identifying the respective compounds.

Example 1

3-oxo-3,4-dihydro-2H-benzo[1,4]thiazine-6-carboxylic acid [1-(6-methoxy-3,4-dihydro-2H-1-oxa-5, 9-diaza-phenanthren-3-ylmethyl)-piperidin-4-yl]-amide

Preparation of 3-chloro-6-methoxy-[1,5]naphthyridine-4-carbonitrile

CoppeeI cyanide (39.3 g, 0.44 mol, 1.2 eq) is added at room temperature to a stirred solution of 8-bromo-7-chloro-2-methoxy-[1,5]naphthyridine (100 g, 0.37 mol, 1.0 eq) in N,N-dimethylformamide (1.5 L). After 8 hours stirring at 130° C., the reaction mixture is cooled down to room temperature and treated with a saturated ammonium chloride aqueous solution (1.5 L). The aqueous layer is separated and extracted with ethyl acetate (2×1.5 L). The combined organic layers are dried over sodium sulfate, filtered and concentrated to give a residue that is washed with ethanol (20 mL) to afford 3-chloro-6-methoxy-[1,5]naphthyridine-4-carbonitrile as an off-white solid (49.5 g, 62% yield).

$^1$H-NMR (400 MHz, DMSO-d6) δ ppm: 8.98 (s, 1H), 8.33 (d, J=9.2 Hz, 1H), 7.37 (d, J=9.2 Hz, 1H), 4.05 (s, 3H).

MS m/z (+ESI): 220.1 [M+H]⁺.

Preparation of 3-benzyloxy-6-methoxy-[1,5]naphthyridine-4-carbonitrile

Sodium hydride (70 mg, 1.73 mmol, 2.0 eq) is added at −30° C. to a stirred solution of 3-chloro-6-methoxy-[1,5]naphthyridine-4-carbonitrile (190 mg, 0.87 mmol, 1.0 eq) and benzyl alcohol (187 mg, 1.73 mmol, 2.0 eq) in tetrahydrofuran (12 mL). After 2 hours stirring at −30° C., the reaction mixture is concentrated and extracted with ethyl acetate (3×20 mL) and water (20 mL). The combined organic layers are dried over sodium sulfate, filtered and concentrated to give a residue that is purified by column chromatography (silica gel, eluent: petroleum ether:ethyl acetate, 5:1, v/v) to afford 3-benzyloxy-6-methoxy-[1,5]naphthyridine-4-carbonitrile as a light yellow solid (160 mg, 64% yield).

$^1$H-NMR (400 MHz, DMSO-d6) δ ppm: 9.06 (s, 1H), 8.31 (d, J=8.8 Hz, 1H), 7.45 (m, 5H), 7.22 (d, J=8.8 Hz, 1H), 5.61 (s, 2H), 4.05 (s, 3H).

MS m/z (+ESI): 292.0 [M+H]⁺.

Preparation of 3-benzyloxy-6-methoxy-[1,5]naphthyridine-4-carboxylic acid amide 30% Hydrogen peroxide (17.2 mmol, 5.0 eq) is added dropwise at room temperature to a stirred suspension of 3-benzyloxy-6-methoxy-[1,5]naphthyridine-4-carbonitrile (1.0 g, 3.43 mmol, 1.0 eq) and sodium hydroxide (69 mg, 0.17 mmol, 0.05 eq) in methanol (100 mL). After 1 hour stirring at 70° C., a catalytic amount of manganese dioxide is added to the reaction mixture that is concentrated to give a crude that is purified by column chromatography (silica gel, eluent: petroleum ether:ethyl acetate, 1:1, v/v) to afford 3-benzyloxy-6-methoxy-[1,5]naphthyridine-4-carboxylic acid amide as a white solid (800 mg, 75% yield).

$^1$H-NMR (400 MHz, CDCl$_3$) δ ppm: 8.67 (s, 1H), 8.12 (d, J=8.8 Hz, 1H), 7.40 (m, 5H), 6.48 (d, J=8.8 Hz, 1H), 6.48 (br, 1H), 6.02 (br, 1H), 5.40 (s, 2H), 4.06 (s, 3H).

MS m/z (+ESI): 310.0 [M+H]$^+$.

Preparation of (3-benzyloxy-6-methoxy-[1,5]naphthyridin-4-yl)-methanol

A solution of 3-benzyloxy-6-methoxy-[1,5]naphthyridine-4-carboxylic acid amide (640 mg, 2.07 mmol, 1.0 eq) in tetrahydrofuran (50 mL) is added at room temperature to a flask charged with Schwartz's reagent (800 mg, 3.1 mmol, 1.5 eq) and the resulting mixture is stirred at room temperature for 10 minutes. Solvent is removed to give a crude that is purified by column chromatography (silica gel, eluent: petroleum ether:ethyl acetate, 1:1, v/v) to afford a mixture of aldehyde and alcohol. This mixture is dissolved in methanol (20 mL) and sodium borohydride (39 mg, 1.03 mmol, 0.5 eq) is added at room temperature. After 5 minutes stirring at room temperature, solvent is removed to give a crude that is purified by column chromatography (silica gel, eluent: petroleum ether:ethyl acetate, 4:1, v/v) to afford (3-benzyloxy-6-methoxy-[1,5]naphthyridin-4-yl)-methanol as a white solid (390 mg, 64% yield).

$^1$H-NMR (400 MHz, CDCl$_3$) δ ppm: 8.65 (s, 1H), 8.18 (d, J=9.2 Hz, 1H), 7.42 (m, 5H), 7.02 (d, J=9.2 Hz, 1H), 5.33 (s, 2H), 5.28 (s, 2H), 4.07 (s, 3H).

MS m/z (+ESI): 297.1 [M+H]$^+$.

Preparation of 4-hydroxymethyl-6-methoxy-[1,5]naphthyridin-3-ol

10% Palladium on activated carbon (140 mg, 0.13 mmol, 0.1 eq) is added at room temperature to a stirred solution of (3-benzyloxy-6-methoxy-[1,5]naphthyridin-4-yl)-methanol (390 mg, 1.32 mmol, 1.0 eq) in methanol (30 mL). The resulting mixture is stirred under hydrogen flow (4 bars) at room temperature for 1 hour. The catalyst is then removed by filtration and the solution is concentrated to afford 4-hydroxymethyl-6-methoxy-[1,5]naphthyridin-3-ol as a white solid (220 mg, 81% yield).

$^1$H-NMR (400 MHz, CD$_3$OD) δ ppm: 8.38 (s, 1H), 8.07 (d, J=9.2 Hz, 1H), 6.99 (d, J=9.2 Hz, 1H), 5.30 (s, 2H), 4.06 (s, 3H).

MS m/z (+ESI): 207.1 [M+H]$^+$.

Preparation of 3-hydroxy-6-methoxy-[1,5]naphthyridine-4-carbaldehyde

Manganese dioxide (530 mg, 6.05 mmol, 5.0 eq) is added at room temperature to a stirred solution of 4-hydroxymethyl-6-methoxy-[1,5]naphthyridin-3-ol (250 mg, 1.21 mmol, 1.0 eq) in acetonitrile (10 mL) and the resulting mixture is stirred at 35° C. for 1 hour. The solid is filtered off, washed with acetone (3×10 mL) and the filtrate is concentrated to give a residue that is purified by column chromatography (silica gel, eluent: petroleum ether:ethyl acetate, 1:4, v/v) to afford 3-hydroxy-6-methoxy-[1,5]naphthyridine-4-carbaldehyde as a light yellow solid (180 mg, 73% yield).

$^1$H-NMR (400 MHz, CDCl$_3$) δ ppm: 11.89 (s, 1H), 11.19 (s, 1H), 8.66 (s, 1H), 8.17 (d, J=8.8 Hz, 1H), 7.01 (d, J=8.8 Hz, 1H), 4.09 (s, 3H).

MS m/z (+ESI): 205.1 [M+H]$^+$.

Preparation of 6-methoxy-2H-1-oxa-5,9-diaza-phenanthrene-3-carboxylic acid methyl ester 1,4-Diazabicyclo[2.2.2]octane (522 mg, 4.65 mmol, 1.0 eq) is added at room temperature to a stirred suspension of 3-hydroxy-6-methoxy-[1,5]naphthyridine-4-carbaldehyde (950 mg, 4.65 mmol, 1.0 eq) in acrylic acid methyl ester (20 mL) and the resulting mixture is heated under reflux for 3 hours. The reaction mixture is then cooled down to room temperature, solvent is removed and the residue is dissolved in 1,2-dichloroethane (20 mL). Triethylamine (19.5 mL, 139.6 mmol, 30.0 eq) is then added at 0° C., followed by methanesulfonyl chloride (3.85 mL, 69.8 mml, 15.0 eq) and the resulting mixture is heated under reflux for 4 hours. Solvent is removed and the residue is extracted with dichloromethane (3×40 mL) and water (40 mL). The combined organic layers are dried over sodium sulfate, filtered and concentrated to give a residue that is purified by column chromatography (silica gel, eluent: petroleum ether:ethyl acetate, 10:1 to 5:1, v/v) to afford 6-methoxy-2H-1-oxa-5,9-diaza-phenanthrene-3-carboxylic acid methyl ester as a light yellow oil (670 mg, 53% yield).

$^1$H-NMR (400 MHz, DMSO-d6) δ ppm: 8.50 (s, 1H), 8.16 (d, J=8.8 Hz, 1H), 8.12 (s, 1H), 7.11 (d, J=8.8 Hz, 1H), 5.16 (s, 2H), 4.03 (s, 3H), 3.79 (s, 3H).

MS m/z (+ESI): 273.0 [M+H]$^+$.

Preparation of (6-methoxy-3,4-dihydro-2H-1-oxa-5,9-diaza-phenanthren-3-yl)-methanol Sodium borohydride (417 mg, 11.03 mmol, 5.0 eq) is added at 0° C. to a stirred suspension of 6-methoxy-2H-1-oxa-5,9-diaza-phenanthrene-3-carboxylic acid methyl ester (600 mg, 2.20 mmol, 1.0 eq) in methanol (60 mL), followed by lithium chloride (467 mg, 11.03 mmol, 5.0 eq). After 3 hours stirring at room temperature, solvent is removed and the residue is dissolved in methanol (60 mL) and treated with 10% palladium on activated carbon (100 mg, 0.09 mmol, 0.05 eq). The resulting mixture is stirred under hydrogen flow (3 bars) at room temperature for 3 hours. The catalyst is then removed by filtration and the solution is concentrated to give a residue that is purified by column chromatography (silica gel, eluent: petroleum ether:ethyl acetate, 4:1 to 3:1, v/v) to afford (6-methoxy-3,4-dihydro-2H-1-oxa-5,9-diaza-phenanthren-3-yl)-methanol as a white solid (400 mg, 74% yield).

$^1$H-NMR (400 MHz, DMSO-d6) δ ppm: 8.36 (s, 1H), 8.11 (d, J=8.8 Hz, 1H), 7.01 (d, J=8.8 Hz, 1H), 4.84 (t, J=5.2 Hz, 1H), 4.02-4.39 (m, 2H), 3.98 (s, 3H), 3.41-3.57 (m, 2H), 2.72-3.22 (m, 2H), 2.19-2.48 (m, 1H).

MS m/z (+ESI): 247.1 [M+H]$^+$.

Preparation of 3-bromomethyl-6-methoxy-3,4-dihydro-2H-1-oxa-5,9-diaza-phenanthrene A solution of (6-methoxy-3,4-dihydro-2H-1-oxa-5,9-diaza-phenanthren-3-yl)-methanol (1.5 g, 5.40 mmol, 1.0 eq) in dichloromethane (20 mL) is added at room temperature to a stirred suspension of 2,3-dichloro-5,6-dicyano-1,4-benzoquinone (2.08 g, 9.17 mmol, 1.7 eq), triphenylphosphine (2.4 g, 9.17 mmol, 1.7 eq) and tetrabutylammonium bromide (2.95 g, 9.17 mmol, 1.7 eq) in dichloromethane (30 mL). After 1 hour stirring at room temperature, solvent is removed and the residue is purified by column chromatography (silica gel, eluent: petroleum ether:ethyl acetate, 5:1, v/v) to afford 3-bromomethyl-6-methoxy-3,4-dihydro-2H-1-oxa-5,9-diaza-phenanthrene as a white solid (1.4 g, 84% yield).
$^1$H-NMR (400 MHz, CDCl$_3$) δ ppm: 8.43 (s, 1H), 8.12 (d, J=8.8 Hz, 1H), 6.95 (d, J=8.8 Hz, 1H), 4.13-4.46 (m, 2H), 4.06 (s, 3H), 3.41-3.59 (m, 2H), 3.02 (m, 2H), 2.55 (m, 1H).
MS m/z (+ESI): 309.2, 311.1 [M+H]$^+$.

Preparation of 4-[(3-oxo-3,4-dihydro-2H-benzo[1,4]thiazine-6-carbonyl)-amino]-piperidine-1-carboxylic acid tert-butyl ester 3-Oxo-3,4-dihydro-2H-benzo[1,4]thiazine-6-carboxylic acid (556 mg, 2.45 mmol, 1.0 eq) is added at room temperature to a stirred solution of 4-amino-piperidine-1-carboxylic acid tert-butyl ester (500 mg, 2.45 mmol, 1.0 eq) in N,N-dimethylformamide (20 mL), followed by 1-hydroxybenzotriazole (421 mg, 2.69 mmol, 1.1 eq), N-(3-dimethylaminopropyl)-N'-ethylcarbodiimide hydrochloride (550 mg, 2.81 mmol, 1.15 eq) and N,N-diisopropylethylamine (962 µL, 5.50 mmol, 2.25 eq). After 15 hours stirring at room temperature, solvent is evaporated and the residue is extracted with dichloromethane (3×30 mL) and water (30 mL). The combined organic layers are dried over sodium sulfate, filtered and concentrated to give a crude product that is purified by column chromatography (silica gel, eluent: cyclohexane:ethyl acetate:methanol, 1:3:0 to 0/9/1, v/v/v) to afford 4-[(3-oxo-3,4-dihydro-2H-benzo[1,4]thiazine-6-carbonyl)-amino]-piperidine-1-carboxylic acid tert-butyl ester as a light yellow solid (621 mg, 62% yield).
$^1$H-NMR (400 MHz, DMSO-d6) δ ppm: 10.66 (s, 1H), 8.27 (d, J=7.8 Hz, 1H), 7.42 (m, 3H), 3.96 (m, 3H), 3.51 (s, 2H), 2.90 (m, 2H), 1.76 (m, 2H), 1.40 (m, 11H).
MS m/z (+ESI): 392.3 [M+H]$^+$, 414.3 [M+Na]$^+$.

Preparation of 3-oxo-3,4-dihydro-2H-benzo[1,4]thiazine-6-carboxylic acid piperidin-4-ylamide Trifluoroacetic acid (1.73 mL, 22.20 mmol, 15.0 eq) is added at 0° C. to a stirred solution of 4-[(3-oxo-3,4-dihydro-2H-benzo[1,4]thiazine-6-carbonyl)-amino]-piperidine-1-carboxylic acid tert-butyl ester (610 mg, 1.48 mmol, 1.0 eq) in dichloromethane (20 mL). After 2 hours stirring at room temperature, the reaction mixture is extracted with dichloromethane (3×20 mL) and water (20 mL) and the pH is adjusted to 12 by the addition of a 1N sodium hydroxide aqueous solution. The combined organic layers are dried over sodium sulfate, filtered and concentrated to afford 3-oxo-3,4-dihydro-2H-benzo[1,4]thiazine-6-carboxylic acid piperidin-4-ylamide as a light brown solid (244 mg, 51% yield).
MS m/z (+ESI): 292.3 [M+H]$^+$.

Preparation of 3-oxo-3,4-dihydro-2H-benzo[1,4]thiazine-6-carboxylic acid [1-(6-methoxy-3,4-dihydro-2H-1-oxa-5,9-diaza-phenanthren-3-ylmethyl)-piperidin-4-yl]-amide 3-Oxo-3,4-dihydro-2H-benzo[1,4]thiazine-6-carboxylic acid piperidin-4-ylamide (56 mg, 0.16 mmol, 1.0 eq) is added at room temperature to a stirred solution of 3-bromomethyl-6-methoxy-3,4-dihydro-2H-1-oxa-5,9-diaza-phenanthrene (50 mg, 0.16 mmol, 1.0 eq) in N,N-dimethylformamide (2 mL), followed by N,N-diisopropylethylamine (30 µL, 0.17 mmol, 1.1 eq). After 24 hours stirring at 80° C., solvent is removed and the residue is extracted with dichloromethane (3×10 mL) and water (10 mL). The combined organic layers are dried over sodium sulfate, filtered and concentrated to give a residue that is purified by preparative HPLC to afford 3-oxo-3,4-dihydro-2H-benzo[1,4]thiazine-6-carboxylic acid [1-(6-methoxy-3,4-dihydro-2H-1-oxa-5,9-diaza-phenanthren-3-ylmethyl)-piperidin-4-yl]-amide as an off-white lyophilized powder (39 mg, 47% yield).
$^1$H-NMR (400 MHz, DMSO-d6) δ ppm: 10.66 (s, 1H), 8.41 (s, 1H), 8.26 (d, J=7.7 Hz, 1H), 8.17 (d, J=8.9 Hz, 1H), 7.44 (m, 3H), 7.07 (d, J=9.0 Hz, 1H), 4.40 (d, J=10.7 Hz, 1H), 4.01 (m, 4H), 3.77 (m, 1H), 3.51 (s, 2H), 3.26 (m, 1H), 2.87-3.02 (m, 2H), 2.73 (m, 1H), 2.37 (m, 3H), 1.97-2.13 (m, 2H), 1.79 (m, 2H), 1.62 (m, 2H).
MS m/z (+ESI): 520.6 [M+H]$^+$.

Example 13

3-oxo-3,4-dihydro-2H-benzo[1,4]thiazine-6-carboxylic acid [trans-4-(8-methoxy-1,2-dihydro-3-oxa-5,9-diaza-cyclopenta[a]naphthalen-2-ylmethyl)-cyclohexyl]-amide Preparation of 7-benzyloxy-8-bromomethyl-2-methoxy-[1,5]naphthyridine Phosphorus tribromide (32 µL, 0.34 mmol, 2.0 eq) is added at room temperature to a stirred solution of (3-benzyloxy-6-methoxy-[1,5]naphthyridine-4-yl)-methanol (50 mg, 0.17 mmol, 1.0 eq) in dichloromethane (5 mL). After 1 hour stirring at room temperature, pH of the reaction mixture is adjusted to 7 by the addition of a sodium carbonate aqueous solution. The resulting solution is extracted with dichloromethane (3×10 mL) and water (10 mL). The combined organic layers are dried over sodium sulfate, filtered and concentrated to afford 7-benzyloxy-8-bromomethyl-2-methoxy-[1,5]naphthyridine as a white solid (62 mg, 99% yield).
$^1$H-NMR (400 MHz, CDCl$_3$) δ ppm: 8.64 (s, 1H), 8.12 (d, J=8.8 Hz, 1H), 7.36-7.54 (m, 5H), 7.01 (d, J=8.8 Hz, 1H), 5.42 (s, 2H), 5.13 (s, 2H), 4.13 (s, 3H).
MS m/z (+ESI): 359.2, 361.3 [M+H]$^+$.

Preparation of (3-benzyloxy-6-methoxy-[1,5]naphthyridin-4-ylmethyl)-phosphonic acid diethyl ester Triethyl phosphate (960 µL, 5.60 mmol, 10.0 eq) is added at room temperature to a stirred solution of 7-benzyloxy-8-bromomethyl-2-methoxy-[1,5]naphthyridine (200 mg, 0.56 mmol, 1.0 eq) in toluene (1 mL) and the resulting mixture is heated under reflux for 6 hours. Solvent is then removed and the residue is purified by column chromatography (silica gel, eluent: petroleum ether:ethyl acetate, 1:1, v/v) to afford (3-benzyloxy-6-methoxy-[1,5]naphthyridin-4-ylmethyl)-phosphonic acid diethyl ester as a yellow oil (180 mg, 79% yield).
$^1$H-NMR (400 MHz, DMSO-d6) δ ppm: 8.80 (s, 1H), 8.18 (d, J=9.2 Hz, 1H), 7.31-7.65 (m, 5H), 7.09 (d, J=9.2 Hz, 1H), 5.44 (s, 2H), 4.03 (s, 3H), 3.87 (q, J=6.8 Hz, 4H), 3.77 (d, J=22.4 Hz, 2H), 1.03 (t, J=6.8 Hz, 6H).
MS m/z (+ESI): 417.0 [M+H]$^+$.

Preparation of {trans-4-[3-(3-benzyloxy-6-methoxy-[1,5]naphthyridin-4-yl)-allyl]-cyclohexyl}-carbamic acid tert-butyl ester Sodium hydride (86 mg, 1.91 mmol, 2.3 eq) is added at 0° C. to a stirred solution of (3-benzyloxy-6-methoxy-[1,5]naphthyridin-4-ylmethyl)-phosphonic acid diethyl ester (350 mg, 0.83 mmol, 1.0 eq) in tetrahydrofuran (30 mL) and the resulting mixture is stirred at 0° C. for 1 hour before the addition of a solution of [trans-4-(2-oxo-ethyl)-cyclohexyl]- carbamic acid tert-butyl ester (200 mg, 0.83 mmol, 1.0 eq) in tetrahydrofuran (5 mL). After 15 hours stirring at room temperature, the reaction mixture is quenched with ammonium chloride aqueous solution (20 mL), tetrahydrofuran is removed and the resulting residue is extracted with ethyl acetate (3×50 mL) and brine (50 mL). The combined organic layers are dried over sodium sulfate, filtered and concentrated to give a residue that is purified by column chromatography (silica gel, eluent: petroleum ether:ethyl acetate, 10:1 to 6:1, v/v) to afford {trans-4-[3-(3-benzyloxy-6-methoxy-[1,5]naphthyridin-4-yl)-allyl]-cyclohexyl}-carbamic acid tert-butyl ester as a white solid (548 mg, 55% yield).

$^1$H-NMR (400 MHz, CDCl$_3$) δ ppm: 8.62 (s, 1H), 8.17 (m, 1H), 7.00-7.47 (m, 8H), 5.32 (s, 2H), 4.37 (s, 1H), 4.08 (s, 3H), 3.37 (m, 1H), 1.81-2.25 (m, 6H), 1.25-1.44 (m, 10H), 1.03 (m, 4H).

MS m/z (+ESI): 504.2 [M+H]$^+$.

Preparation of {trans-4-[3-(3-benzyloxy-6-methoxy-[1,5]naphthyridin-4-yl)-2,3-dihydroxy-propyl]-cyclohexyl}-carbamic acid tert-butyl ester Potassium osmate(VI) dihydrate (188 mg, 0.51 mmol, 0.25 eq) is added at room temperature to a stirred solution of {trans-4-[3-(3-benzyloxy-6-methoxy-[1,5]naphthyridin-4-yl)-allyl]-cyclohexyl}-carbamic acid tert-butyl ester (1.03 g, 2.05 mmol, 1.0 eq) in acetone (350 mL) and water (15 mL), followed by 4-methyl-morpholin-4-oxide (720 mg, 6.14 mmol, 3.0 eq). After 15 hours stirring at room temperature, acetone is removed and the resulting residue is extracted with ethyl acetate (3×30 mL) and brine (30 mL). The combined organic layers are dried over sodium sulfate, filtered and concentrated to afford {trans-4-[3-(3-benzyloxy-6-methoxy-[1,5]naphthyridin-4-yl)-2,3-dihydroxy-propyl]-cyclohexyl}-carbamic acid tert-butyl ester (1.0 g, 91% yield) which is directly engaged in the next step.

$^1$H-NMR (400 MHz, CDCl$_3$) δ ppm: 8.67 (s, 1H), 8.30 (m, 1H), 7.29-7.43 (m, 5H), 7.06 (m, 1H), 5.28-5.43 (m, 3H), 4.31 (s, 1H), 4.01 (s, 3H), 3.28 (m, 2H), 1.55-1.90 (m, 6H), 0.70-1.44 (m, 14H).

MS m/z (+ESI): 538.2 [M+H]$^+$.

Preparation of {trans-4-[5-(3-benzyloxy-6-methoxy-[1,5]naphthyridin-4-yl)-2-oxo-[1,3]dioxolan-4-ylmethyl]-cyclohexyl}-carbamic acid tert-butyl ester N,N'-Carbonyldiimidazole (2.56 g, 15.83 mmol, 5.0 eq) is added at room temperature to a stirred solution of {trans-4-[3-(3-benzyloxy-6-methoxy-[1,5]naphthyridin-4-yl)-2,3-dihydroxy-propyl]-cyclohexyl}-carbamic acid tert-butyl ester (1.70 g, 3.16 mmol, 1.0 eq) in toluene (150 mL). After 2 hours stirring at 70° C., solvent is removed and the crude is purified by column chromatography (silica gel, eluent: petroleum ether:ethyl acetate, 5:1, v/v) to afford {trans-4-[5-(3-benzyloxy-6-methoxy-[1,5]naphthyridin-4-yl)-2-oxo-[1,3]dioxolan-4-ylmethyl]-cyclohexyl}-carbamic acid tert-butyl ester as a white solid (1.70 g, 96% yield).

$^1$H-NMR (400 MHz, CDCl$_3$) δ ppm: 8.70 (s, 1H), 8.17 (d, J=8.8 Hz, 1H), 7.36-7.45 (m, 5H), 7.04 (d, J=8.8 Hz, 1H), 6.23 (m, 1H), 5.40 (s, 2H), 5.01 (m, 1H), 4.31 (s, 1H), 4.06 (s, 3H), 3.32 (m, 1H), 1.39-1.90 (m, 16H), 0.94-1.04 (m, 4H).

MS m/z (+ESI): 564.2 [M+H]$^+$.

Preparation of {trans-4-[2-hydroxy-3-(3-hydroxy-6-methoxy-[1,5]naphthyridin-4-yl)-propyl]-cyclohexyl}-carbamic acid tert-butyl ester 10% Palladium on activated carbon (976 mg, 0.91 mmol, 0.3 eq) is added at room temperature to a stirred solution of {trans-4-[5-(3-benzyloxy-6-methoxy-[1,5]naphthyridin-4-yl)-2-oxo-[1,3]dioxolan-4-ylmethyl]-cyclohexyl}-carbamic acid tert-butyl ester (1.70 g, 3.02 mmol, 1.0 eq) in methanol (200 mL), followed by several drops of triethylamine. The resulting mixture is stirred under hydrogen flow (1 bar) at room temperature for 1 hour. The catalyst is then removed by filtration and the solution is concentrated to afford {trans-4-[2-hydroxy-3-(3-hydroxy-6-methoxy-[1,5]naphthyridin-4-yl)-propyl]-cyclohexyl}-carbamic acid tert-butyl ester as a white solid (890 mg, 68% yield).

$^1$H-NMR (400 MHz, DMSO-d6) δ ppm: 8.42 (s, 1H), 8.08 (d, J=8.8 Hz, 1H), 6.97 (d, J=8.8 Hz, 1H), 6.60 (m, 1H), 4.07 (s, 1H), 3.97 (s, 3H), 3.07-3.23 (m, 3H), 1.33-1.64 (m, 15H), 0.66-1.08 (m, 5H).

MS m/z (+ESI): 432.1 [M+H]$^+$.

Preparation of [trans-4-(8-methoxy-1,2-dihydro-3-oxa-5,9-diaza-cyclopenta[a]naphthalen-2-ylmethyl)-cyclohexyl]-carbamic acid tert-butyl ester Diethyl azodicarboxylate (650 µL, 4.13 mmol, 2.0 eq) is added at 0° C. to a stirred solution of {trans-4-[2-hydroxy-3-(3-hydroxy-6-methoxy-[1,5]naphthyridin-4-yl)-propyl]-cyclohexyl}-carbamic acid tert-butyl ester (890 mg, 2.06 mmol, 1.0 eq) in tetrahydrofuran (100 mL), followed by triphenylphosphine (1.08 g, 4.13 mmol, 2.0 eq). After 1 hour stirring at room temperature, solvent is removed and the crude is purified by column chromatography (silica gel, eluent: petroleum ether:ethyl acetate, 5:1, v/v) to afford [trans-4-(8-methoxy-1,2-dihydro-3-oxa-5,9-diaza-cyclopenta[a]naphthalen-2-ylmethyl)-cyclohexyl]-carbamic acid tert-butyl ester as a white solid (420 mg, 49% yield).

$^1$H-NMR (400 MHz, DMSO-d6) δ ppm: 8.45 (s, 1H), 8.15 (d, J=8.8 Hz, 1H), 7.02 (d, J=8.8 Hz, 1H), 6.68 (m, 1H), 5.15 (m, 1H), 3.97 (s, 3H), 3.06-3.67 (m, 3H), 0.99-1.87 (m, 20H).

MS m/z (+ESI): 414.3 [M+H]$^+$.

Preparation of trans-4-(8-methoxy-1,2-dihydro-3-oxa-5,9-diaza-cyclopenta[a]naphthalen-2-ylmethyl)-cyclohexylamine Trifluoroacetic acid (821 µL, 10.56 mmol, 15.0 eq) is added at 0° C. to a stirred solution of [trans-4-(8-methoxy-1,2-dihydro-3-oxa-5,9-diaza-cyclopenta[a]naphthalen-2-ylmethyl)-cyclohexyl]-carbamic acid tert-butyl ester (300 mg, 0.70 mmol, 1.0 eq) in dichloromethane (12 mL). After 2 hours stirring at room temperature, the reaction mixture is extracted with dichloromethane (3×10 mL) and water (10 mL) and the pH is adjusted to 12 by the addition of a 1N sodium hydroxide aqueous solution. The combined organic layers are dried over sodium sulfate, filtered and concentrated to afford trans-4-(8-methoxy-1,2-dihydro-3-oxa-5,9-diaza-cyclopenta[a]naphthalen-2-ylmethyl)-cyclohexylamine as an orange viscous oil (190 mg, 82% yield).

MS m/z (+ESI): 314.4 [M+H]$^+$.

Preparation of 3-oxo-3,4-dihydro-2H-benzo[1,4]thiazine-6-carboxylic acid [trans-4-(8-methoxy-1,2-dihydro-3-oxa-5,9-diaza-cyclopenta[a]naphthalen-2-ylmethyl)-cyclohexyl]-amide 3-Oxo-3,4-dihydro-2H-benzo[1,4]thiazine-6-carboxylic acid (31 mg, 0.14 mmol, 1.0 eq) is added at room temperature to a stirred solution of trans-4-(8-methoxy-1,2-dihydro-3-oxa-5,9-diaza-cyclopenta[a]naphthalen-2-ylmethyl)-cyclohexylamine (47 mg, 0.14 mmol, 1.0 eq) in N,N-dimethylformamide (4 mL), followed by 1-hydroxybenzotriazole (24 mg, 0.16 mmol, 1.1 eq), N-(3-dimethylaminopropyl)-N'-ethylcarbodiimide hydrochloride (32 mg, 0.16 mmol, 1.15 eq) and N,N-diisopropylethylamine (56 μL, 0.32 mmol, 2.25 eq). After 15 hours stirring at room temperature, solvent is evaporated and the residue is extracted with dichloromethane (3×10 mL) and water (10 mL). The combined organic layers are dried over sodium sulfate, filtered and concentrated to give a crude product that is purified by preparative HPLC to afford 3-oxo-3,4-dihydro-2H-benzo[1,4]thiazine-6-carboxylic acid [trans-4-(8-methoxy-1,2-dihydro-3-oxa-5,9-diaza-cyclopenta[a]naphthalen-2-ylmethyl)-cyclohexyl]-amide as a white lyophilized powder (16 mg, 21% yield).

$^1$H-NMR (400 MHz, DMSO-d6) δ ppm: 10.67 (s, 1H), 8.49 (s, 1H), 8.23 (d, J=7.9 Hz, 1H), 8.19 (d, J=9.0 Hz, 1H), 7.44 (m, 3H), 7.06 (d, J=9.1 Hz, 1H), 5.21 (m, 1H), 4.01 (s, 3H), 3.74 (m, 2H), 3.51 (s, 2H), 3.14 (dd, J=7.9, 16.8 Hz, 1H), 1.80-2.00 (m, 5H), 1.66 (m, 1H), 1.57 (m, 1H), 1.39 (m, 2H), 1.13 (m, 2H).

MS m/z (+ESI): 505.5 [M+H]$^+$.

Example 17

3-oxo-3,4-dihydro-2H-benzo[1,4]thiazine-6-carboxylic acid [1-(6-methoxy-3,4-dihydro-2H-1-oxa-9-aza-phenanthren-3-ylmethyl)-piperidin-4-ylmethyl]-amide Preparation of 3-chloro-2-oxo-propionic acid A solution of 2-oxo-propionic acid (50.0 g, 568 mmol, 1.0 eq) in thionyl chloride (79.0 g, 585 mmol, 1.03 eq) is stirred at room temperature for 60 hours. The reaction mixture is dried under vacuum to afford crude 3-chloro-2-oxo-propionic acid as a light yellow viscous oil (60.0 g, 86% yield).

Preparation of 3-hydroxy-6-methoxyquinoline-4-carboxylic acid

3-Chloro-2-oxo-propionic acid (11.46 g, 91.10 mmol, 1.61 eq) is added portionwise at room temperature to a stirred solution of 5-methoxy-1H-indole-2,3-dione (10.0 g, 56.45 mmol, 1.0 eq) and potassium hydroxide (30.5 g, 543.6 mmol, 9.6 eq) in water (60 mL). After 6 days stirring at room temperature, a solution of sodium hydrogen sulfite (2.3 g, 22.10 mmol, 0.4 eq) in water (4 mL) is added and the reaction mixture is acidified by the addition of concentrated hydrochloric acid (12N, 30 mL). The resulting yellow precipitate is collected by filtration, washed successively with a saturated sulfur dioxide aqueous solution and water, then purified by column chromatography (silica gel, eluent: ethyl acetate:acetonitrile:methanol, 70:5:5, v/v/v) to afford 3-hydroxy-6-methoxyquinoline-4-carboxylic acid as a light brown solid (2.66 g, 21% yield).

$^1$H-NMR (400 MHz, DMSO-d6) δ ppm: 8.55 (s, 1H), 7.84 (d, J=8.8 Hz, 1H), 7.66 (s, 1H), 7.20 (d, J=8.8 Hz, 1H), 3.84 (s, 3H).

MS m/z (-ESI): 217.9 [M-H]$^-$.

Preparation of 3-hydroxy-6-methoxyquinoline-4-carboxylic acid methyl ester

Concentrated sulfuric acid (36N, 50 mL) is added dropwise at room temperature to a stirred suspension of 3-hydroxy-6-methoxyquinoline-4-carboxylic acid (14.5 g, 66.15 mmol, 1.0 eq) in methanol (250 mL) and the resulting mixture is heated at 65° C. for 36 hours. Solvent is then evaporated and the residue is quenched with the dropwise addition at 0° C. of saturated sodium hydrogen carbonate aqueous solution. The resulting precipitate is collected by filtration and dried under vacuum to afford 3-hydroxy-6-methoxyquinoline-4-carboxylic acid methyl ester as an off-white powder (15.0 g, 97% yield).

$^1$H-NMR (400 MHz, Acetone-d6) δ ppm: 8.56 (s, 1H), 8.00 (d, J=2.4 Hz, 1H), 7.91 (d, J=9.2 Hz, 1H), 7.23 (dd, J=2.4, 9.2 Hz, 1H), 4.16 (s, 3H), 3.95 (s, 3H).

MS m/z (+ESI): 234.0 [M+H]$^+$.

Preparation of 4-hydroxymethyl-6-methoxy-quinolin-3-ol

A solution of 3-hydroxy-6-methoxyquinoline-4-carboxylic acid methyl ester (5 g, 21.44 mmol, 1.0 eq) in tetrahydrofuran (40 mL) is added at 0° C. to a stirred solution of lithium aluminium hydride (1.63 g, 42.88 mmol, 2.0 eq) in tetrahydrofuran (200 mL). After 1 hour stirring at 0° C., the reaction mixture is cautiously quenched with ice-water (5 mL). After 30 minutes stirring at room temperature, the pH is adjusted to 6 by the addition of a 1N hydrochloric acid aqueous solution, the resulting mixture is filtered and the filtrate is concentrated to afford 4-hydroxymethyl-6-methoxy-quinolin-3-ol as a yellow solid (4 g, 90% yield).

$^1$H-NMR (400 MHz, Acetone-d6) δ ppm: 8.40 (s, 1H), 7.81 (d, J=9.2 Hz, 1H), 7.27 (d, J=2.4 Hz, 1H), 7.13 (dd, J=2.4, 9.2 Hz, 1H), 5.27 (s, 2H), 3.92 (s, 3H).

MS m/z (+ESI): 206.2 [M+H]$^+$.

Preparation of 3-oxo-3,4-dihydro-2H-benzo[1,4]thiazine-6-carboxylic acid [1-(6-methoxy-3,4-dihydro-2H-1-oxa-9-aza-phenanthren-3-ylmethyl)-piperidin-4-ylmethyl]-amide The titled compound is prepared as an off-white lyophilized powder following Scheme 1 and in analogy to Example 1 using 3-bromomethyl-6-methoxy-3,4-dihydro-2H-1-oxa-9-aza-phenanthrene, 4-aminomethyl-piperidine-1-carboxylic acid tert-butyl ester and 3-oxo-3,4-dihydro-2H-benzo[1,4]thiazine-6-carboxylic acid as starting material.

$^1$H-NMR (400 MHz, DMSO-d6) δ ppm: 10.67 (2s, 1H), 8.43 (m, 1H), 8.33 (s, 1H), 7.83 (dd, J=0.9, 9.1 Hz, 1H), 7.37-7.47 (m, 3H), 7.21 (m, 1H), 7.13 (d, J=2.7 Hz, 1H), 4.35 (d, J=9.1 Hz, 1H), 3.94 (m, 4H), 3.51 (2s, 2H), 3.20 (m, 2H), 3.10 (m, 1H), 2.60-2.82 (m, 3H), 2.36 (m, 3H), 1.83-2.08 (m, 3H), 1.68 (m, 2H), 1.45 (m, 1H), 1.02 (m, 1H).

MS m/z (+ESI): 533.2 [M+H]$^+$.

Example 18

6-{[trans-4-(8-methoxy-1,2-dihydro-3-oxa-5,9-diaza-cyclopenta[a]naphthalen-2-ylmethyl)-cyclohexylamino]-methyl}-4H-benzo[1,4]oxazin-3-one 3-Oxo-3,4-dihydro-2H-benzo[1,4]oxazine-6-carbaldehyde (27 mg, 0.14 mmol, 1.0 eq) is added at room temperature to a stirred solution of trans-4-(8-methoxy-1,2-dihydro-3-oxa-5,9-diaza-cyclopenta[a]naphthalen-2-ylmethyl)-cyclohexylamine (47 mg, 0.14 mmol, 1.0 eq) in 1,2-dichloroethane (4 mL) and methanol (1 mL), followed by acetic acid (11 μL, 0.19 mmol, 1.3 eq) and sodium cyanoborohydride (11 mg, 0.16 mmol, 1.15 eq). After 5 hours stirring at room temperature, the reaction mixture is extracted with dichloromethane (3×10 mL) and a saturated sodium hydrogen carbonate aqueous solution (10 mL). The combined organic layers are dried over sodium sulfate, filtered and concentrated to give a residue that is purified by preparative HPLC to afford 6-{[trans-4-(8-methoxy-1,2-dihydro-3-oxa-5,9-diaza-cyclopenta[a]naphthalen-2-ylmethyl)-cyclohexylamino]-methyl}-4H-benzo[1,4]oxazin-3-one as a white lyophilized powder (13 mg, 18% yield).
MS m/z (+ESI): 475.2 [M+H]$^+$.

Example 20

3-oxo-3,4-dihydro-2H-benzo[1,4]thiazine-6-carboxylic acid [1-(6-methoxy-3,4-dihydro-2H-1-oxa-9-aza-phenanthren-3-ylmethyl)-5-(morpholine-4-carbonyl)-pyrrolidin-3-yl]-amide Preparation of 1-(6-methoxy-3,4-dihydro-2H-1-oxa-9-aza-phenanthren-3-ylmethyl)-4-[(3-oxo-3,4-dihydro-2H-benzo[1,4]thiazine-6-carbonyl)-amino]-pyrrolidine-2-carboxylic acid Lithium hydroxide monohydrate (5.5 mg, 0.13 mmol, 1.5 eq) is added at room temperature to a stirred solution of 1-(6-methoxy-3,4-dihydro-2H-1-oxa-9-aza-phenanthren-3-ylmethyl)-4-[(3-oxo-3,4-dihydro-2H-benzo[1,4]thiazine-6-carbonyl)-amino]-pyrrolidine-2-carboxylic acid methyl ester (70 mg, 0.09 mmol, 1.0 eq) in tetrahydrofuran (2 mL) and water (1 mL). After 1 hour stirring at room temperature, the reaction mixture is concentrated and purified by preparative HPLC to afford 1-(6-methoxy-3,4-dihydro-2H-1-oxa-9-aza-phenanthren-3-ylmethyl)-4-[(3-oxo-3,4-dihydro-2H-benzo[1,4]thiazine-6-carbonyl)-amino]-pyrrolidine-2-carboxylic acid as a white lyophilized powder (14 mg, 28% yield).
MS m/z (+ESI): 549.2 [M+H]$^+$.

Preparation of 3-oxo-3,4-dihydro-2H-benzo[1,4]thiazine-6-carboxylic acid [1-(6-methoxy-3,4-dihydro-2H-1-oxa-9-aza-phenanthren-3-ylmethyl)-5-(morpholine-4-carbonyl)-pyrrolidin-3-yl]-amide Morpholine (2 µL, 0.024 mmol, 1.0 eq) is added at room temperature to a stirred solution of 1-(6-methoxy-3,4-dihydro-2H-1-oxa-9-aza-phenanthren-3-ylmethyl)-4-[(3-oxo-3,4-dihydro-2H-benzo[1,4]thiazine-6-carbonyl)-amino]-pyrrolidine-2-carboxylic acid (14 mg, 0.024 mmol, 1.0 eq) in N,N-dimethylformamide (2 mL), followed by 1-hydroxybenzotriazole (4 mg, 0.027 mmol, 1.1 eq), N-(3-dimethylaminopropyl)-N'-ethylcarbodiimide hydrochloride (5 mg, 0.028 mmol, 1.15 eq) and N,N-diisopropylethylamine (13 µL, 0.073 mmol, 3.0 eq). After 15 hours stirring at room temperature, solvent is evaporated and the residue is extracted with dichloromethane (3×5 mL) and water (5 mL). The combined organic layers are dried over sodium sulfate, filtered and concentrated to give a crude product that is purified by preparative HPLC to afford 3-oxo-3,4-dihydro-2H-benzo[1,4]thiazine-6-carboxylic acid [1-(6-methoxy-3,4-dihydro-2H-1-oxa-9-aza-phenanthren-3-ylmethyl)-5-(morpholine-4-carbonyl)-pyrrolidin-3-yl]-amide as a white lyophilized powder (12 mg, 76% yield).
MS m/z (+ESI): 618.2 [M+H]$^+$.

Example 31

3-oxo-3,4-dihydro-2H-benzo[1,4]thiazine-6-carboxylic acid [1-(6-methoxy-3,4-dihydro-2H-1-oxa-9-aza-phenanthren-3-ylmethyl)-1H-pyrazol-4-yl]-amide Preparation of 6-methoxy-3-(4-nitro-pyrazol-1-ylmethyl)-3,4-dihydro-2H-1-oxa-9-aza-phenanthrene 4-Nitro-1H-pyrazole (118 mg, 1.02 mmol, 1.0 eq) is added at room temperature to a stirred solution of 3-bromomethyl-6-methoxy-3,4-dihydro-2H-1-oxa-9-aza-phenanthrene (350 mg, 1.02 mmol, 1.0 eq) in N,N-dimethylformamide (12 mL), followed by N,N-diisopropylethylamine (196 µL, 1.12 mmol, 1.1 eq). After 24 hours stirring at 80° C., solvent is removed and the residue is extracted with dichloromethane (3×20 mL) and water (20 mL). The combined organic layers are dried over sodium sulfate, filtered and concentrated to give a residue that is purified by column chromatography (silica gel, eluent: cyclohexane:ethyl acetate, 1:1 to 0:1, v/v) to afford 6-methoxy-3-(4-nitro-pyrazol-1-ylmethyl)-3,4-dihydro-2H-1-oxa-9-aza-phenanthrene as a light yellow viscous oil (222 mg, 61% yield).
MS m/z (+ESI): 341.3 [M+H]$^+$.

Preparation of 1-(6-methoxy-3,4-dihydro-2H-1-oxa-9-aza-phenanthren-3-ylmethyl)-/H-pyrazol-4-ylamine 10% Palladium on activated carbon (13 mg, 0.12 mmol, 0.2 eq) is added at room temperature to a stirred solution of 6-methoxy-3-(4-nitro-pyrazol-1-ylmethyl)-3,4-dihydro-2H-1-oxa-9-aza-phenanthrene (220 mg, 0.61 mmol, 1.0 eq) in ethyl acetate (4 mL). The resulting mixture is stirred under hydrogen flow (4 bars) at room temperature for 1 hour. The catalyst is then removed by filtration and the solution is concentrated to afford 1-(6-methoxy-3,4-dihydro-2H-1-oxa-9-aza-phenanthren-3-ylmethyl)-/H-pyrazol-4-ylamine as a brown viscous oil (210 mg, 99% yield).
MS m/z (+ESI): 311.3 [M+H]$^+$.

Preparation of 3-oxo-3,4-dihydro-2H-benzo[1,4]thiazine-6-carboxylic acid [1-(6-methoxy-3,4-dihydro-2H-1-oxa-9-aza-phenanthren-3-ylmethyl)-/H-pyrazol-4-yl]-amide The titled compound is prepared as an off-white lyophilized powder following Scheme 2 and in analogy to Example 1 using 1-(6-methoxy-3,4-dihydro-2H-1-oxa-9-aza-phenanthren-3-ylmethyl)-/H-pyrazol-4-ylamine and 3-oxo-3,4-dihydro-2H-benzo[1,4]thiazine-6-carboxylic acid as starting material.
$^1$H-NMR (400 MHz, DMSO-d6) δ ppm: 10.77 (s, 1H), 10.48 (s, 1H), 8.37 (s, 1H), 8.15 (s, 1H), 7.86 (d, J=9.1 Hz, 1H), 7.67 (d, J=0.5 Hz, 1H), 7.55 (m, 3H), 7.24 (dd, J=2.7, 9.1 Hz, 1H), 7.11 (d, J=2.7 Hz, 1H), 4.27 (m, 3H), 3.97 (m, 1H), 3.92 (s, 3H), 3.55 (s, 2H), 3.17 (m, 1H), 2.81 (m, 2H).
MS m/z (+ESI): 502.2 [M+H]$^+$.

Example 34

6-{[1-(6-methoxy-3,4-dihydro-2H-1-oxa-9-aza-phenanthren-3-ylmethyl)-piperidin-4-ylamino]-methyl}-4H-benzo[1,4]thiazine Preparation of [1-(6-methoxy-3,4-dihydro-2H-1-oxa-9-aza-phenanthren-3-ylmethyl)-piperidin-4-yl-carbamic acid tert-butyl ester Piperidin-4-yl-carbamic acid tert-butyl ester (301 mg, 1.46 mmol, 1.0 eq) is added at room temperature to a stirred solution of 3-bromomethyl-6-methoxy-3,4-dihydro-2H-1-oxa-5,9-diaza-phenanthrene (500 mg, 1.46 mmol, 1.0 eq) in N,N-dimethylformamide (15 mL), followed by N,N-diisopropylethylamine (281 µL, 1.61 mmol, 1.1 eq). After 24 hours stirring at 80° C., solvent is removed and the residue is extracted with dichloromethane (3×30 mL) and water (30 mL). The combined organic layers are dried over sodium sulfate, filtered and concentrated to give a residue that is purified by column chromatography (silica gel, eluent: cyclohexane:ethyl acetate:methanol, 1:3:0 to 0:1:0 to 0:9:1, v/v/v) to afford [1-(6-methoxy-3,4-dihydro-2H-1-oxa-9-azaphenanthren-3-ylmethyl)-piperidin-4-yl-carbamic acid tert-butyl ester as a brown viscous oil (544 mg, 74% yield).

$^1$H-NMR (400 MHz, DMSO-d6) δ ppm: 8.33 (s, 1H), 7.83 (d, J=9.1 Hz, 1H), 7.22 (dd, J=2.7, 9.1 Hz, 1H), 7.13 (d, J=2.7 Hz, 1H), 6.78 (d, J=7.6 Hz, 1H), 4.33 (m, 1H), 3.95 (m, 1H), 3.92 (s, 3H), 3.26 (m, 1H), 3.11 (m, 1H), 2.75-2.90 (m, 2H), 2.67 (m, 1H), 2.37 (m, 3H), 1.85-2.10 (m, 2H), 1.71 (m, 2H), 1.45 (m, 2H), 1.39 (s, 9H).

MS m/z (+ESI): 428.4 [M+H]$^+$.

Preparation of 1-(6-methoxy-3,4-dihydro-2H-1-oxa-9-aza-phenanthren-3-ylmethyl)-piperidin-4-ylamine Trifluoroacetic acid (1.25 mL, 16.10 mmol, 15.0 eq) is added at 0° C. to a stirred solution of [1-(6-methoxy-3,4-dihydro-2H-1-oxa-9-aza-phenanthren-3-ylmethyl)-piperidin-4-yl-carbamic acid tert-butyl ester (540 mg, 1.07 mmol, 1.0 eq) in dichloromethane (15 mL). After 2 hours stirring at room temperature, the reaction mixture is extracted with dichloromethane (3×20 mL) and water (20 mL) and the pH is adjusted to 12 by the addition of a 1N sodium hydroxide aqueous solution. The combined organic layers are dried over sodium sulfate, filtered and concentrated to afford 1-(6-methoxy-3,4-dihydro-2H-1-oxa-9-aza-phenanthren-3-ylmethyl)-piperidin-4-ylamine as an orange viscous oil (400 mg, 97% yield).

MS m/z (+ESI): 328.3 [M+H]$^+$.

Preparation of 6-{[1-(6-methoxy-3,4-dihydro-2H-1-oxa-9-aza-phenanthren-3-ylmethyl)-piperidin-4-ylamino]-methyl}-4H-benzo[1,4]thiazin-3-one The titled compound is prepared as an off-white lyophilized powder following Scheme 1 and in analogy to Example 18 using 1-(6-methoxy-3,4-dihydro-2H-1-oxa-9-aza-phenanthren-3-ylmethyl)-piperidin-4-ylamine and 3-oxo-3,4-dihydro-2H-benzo[1,4]thiazine-6-carbaldehyde as starting material.

$^1$H-NMR (400 MHz, DMSO-d6) δ ppm: 10.53 (s, 1H), 8.34 (s, 1H), 7.84 (d, J=9.1 Hz, 1H), 7.23 (m, 2H), 7.13 (d, J=2.7 Hz, 1H), 6.98 (m, 2H), 4.34 (m, 1H), 3.95 (m, 1H), 3.92 (s, 3H), 3.71 (s, 2H), 3.44 (s, 2H), 3.11 (m, 1H), 2.78-2.95 (m, 2H), 2.67 (m, 1H), 2.37 (m, 4H), 1.80-2.05 (m, 4H), 1.36 (m, 2H).

MS m/z (+ESI): 505.2 [M+H]$^+$.

Example 36

3-oxo-3,4-dihydro-2H-benzo[1,4]oxazine-6-carboxylic acid [trans-4-(6-methoxy-3,4-dihydro-2H-1-oxa-9-aza-phenanthren-3-ylmethyl)-cyclohexyl]-amide Preparation of [trans-4-(6-methoxy-2-oxo-2H-1-oxa-9-aza-phenanthren-3-ylmethyl)-cyclohexyl]-carbamic acid tert-butyl ester O-(7-azabenzotriazol-1-yl)-N,N,N',N'-tetramethyluronium hexafluorophosphate (1.04 g, 2.73 mmol, 1.5 eq) is added at room temperature to a stirred solution of 3-(trans-4-tert-butoxycarbonylamino-cyclohexyl)-propionic acid (494 mg, 1.82 mmol, 1.0 eq) and 3-hydroxy-6-methoxy-quinoline-4-carbaldehyde (370 mg, 1.82 mmol, 1.0 eq) in N,N-dimethylformamide (20 mL), followed by 1,8-diazabicycloundec-7-ene (817 μL, 5.46 mmol, 3.0 eq). After 4 hours stirring at 50° C., solvent is evaporated and the residue is extracted with ethyl acetate (3×30 mL) and water (30 mL). The combined organic layers are dried over sodium sulfate, filtered and concentrated to give a crude product that is purified by column chromatography (silica gel, eluent: petroleum ether: ethyl acetate, 5:1 to 2:1, v/v) to afford [trans-4-(6-methoxy-2-oxo-2H-1-oxa-9-aza-phenanthren-3-ylmethyl)-cyclohexyl]-carbamic acid tert-butyl ester as a yellow solid (270 mg, 34% yield).

$^1$H-NMR (400 MHz, DMSO-d6) δ ppm: 8.80 (s, 1H), 8.77 (s, 1H), 7.97 (d, J=9.2 Hz, 1H), 7.87 (d, J=2.4 Hz, 1H), 7.40 (dd, J=2.0, 9.2 Hz, 1H), 6.65 (d, J=7.2 Hz, 1H), 3.99 (s, 3H), 3.16 (m, 1H), 2.51 (m, 2H), 1.66-1.76 (m, 5H), 1.34 (s, 9H), 1.02-1.17 (m, 4H).

MS m/z (+ESI): 439.2 [M+H]$^+$.

Preparation of {trans-4-[3-hydroxy-2-(3-hydroxy-6-methoxy-quinolin-4-ylmethyl)-propyl]-cyclohexyl}-carbamic acid tert-butyl ester Sodium borohydride (86 mg, 2.28 mmol, 10.0 eq) is added at 0° C. to a stirred suspension of [trans-4-(6-methoxy-2-oxo-2H-1-oxa-9-aza-phenanthren-3-ylmethyl)-cyclohexyl]-carbamic acid tert-butyl ester (100 mg, 0.23 mmol, 1.0 eq) in methanol (10 mL). After 8 hours stirring at room temperature, the reaction mixture is quenched with ammonium chloride aqueous solution (10 mL), methanol is removed and the resulting residue is extracted with ethyl acetate (3×20 mL) and brine (20 mL). The combined organic layers are dried over sodium sulfate, filtered and concentrated to give a crude product that is purified by column chromatography (silica gel, eluent: petroleum ether:ethyl acetate, 2:1, v/v) to afford {trans-4-[3-hydroxy-2-(3-hydroxy-6-methoxy-quinolin-4-ylmethyl)-propyl]-cyclohexyl}-carbamic acid tert-butyl ester as a white solid (60 mg, 59% yield).

$^1$H-NMR (400 MHz, DMSO-d6) δ ppm: 9.86 (br, 1H), 8.39 (s, 1H), 7.75 (d, J=9.2 Hz, 1H), 7.29 (s, 1H), 7.11 (d, J=9.2 Hz, 1H), 6.61 (d, J=7.6 Hz, 1H), 4.58 (br, 1H), 3.85 (s, 3H), 3.24 (m, 2H), 3.07 (m, 1H), 2.81-2.96 (2m, 2H), 0.68-1.87 (m, 12H), 1.34 (s, 9H).

MS m/z (+ESI): 445.2 [M+H]$^+$.

Preparation of [trans-4-(6-methoxy-3,4-dihydro-2H-1-oxa-9-aza-phenanthren-3-ylmethyl)-cyclohexyl]-carbamic acid tert-butyl ester Diethyl azodicarboxylate (455 μL, 2.90 mmol, 3.0 eq) is added at 0° C. to a stirred solution of {trans-4-[3-hydroxy-2-(3-hydroxy-6-methoxy-quinolin-4-ylmethyl)-propyl]-cyclohexyl}-carbamic acid tert-butyl ester (430 mg, 0.97 mmol, 1.0 eq) in tetrahydrofuran (100 mL), followed by triphenylphosphine (761 mg, 2.90 mmol, 3.0 eq). After 2 hours stirring at room temperature, solvent is removed and the crude is purified by column chromatography (silica gel, eluent: petroleum ether:ethyl acetate, 5:1, v/v) to afford [trans-4-(6-methoxy-3,4-dihydro-2H-1-oxa-9-aza-phenanthren-3-ylmethyl)-cyclohexyl]-carbamic acid tert-butyl ester as an off-white solid (247 mg, 60% yield).

MS m/z (+ESI): 427.2 [M+H]$^+$.

Preparation of 3-oxo-3,4-dihydro-2H-benzo[1,4]oxazine-6-carboxylic acid [trans-4-(6-methoxy-3,4-dihydro-2H-1-oxa-9-aza-phenanthren-3-ylmethyl)-cyclohexyl]-amide The titled compound is prepared as a white lyophilized powder following Scheme 4 and in analogy to Example 1 using [trans-4-(6-methoxy-3,4-dihydro-2H-1-oxa-9-aza-phenanthren-3-ylmethyl)-cyclohexyl]-carbamic acid tert-butyl ester and 3-oxo-3,4-dihydro-2H-benzo[1,4]oxazine-6-carboxylic acid as starting material.

$^1$H-NMR (400 MHz, DMSO-d6) δ ppm: 10.80 (br, 1H), 8.34 (s, 1H), 8.14 (d, J=7.9 Hz, 1H), 7.84 (d, J=9.0 Hz, 1H), 7.46 (dd, J=2.1, 8.4 Hz, 1H), 7.41 (d, J=2.0 Hz, 1H), 7.21 (m, 2H), 6.99 (d, J=8.3 Hz, 1H), 4.64 (s, 2H), 4.33 (m, 1H), 3.94 (s, 3H), 3.85 (m, 1H), 3.66 (m, 1H), 3.19 (m, 1H), 2.60 (m, 1H), 2.23 (m, 1H), 1.86 (m, 4H), 1.51 (m, 1H), 1.27-1.47 (m, 4H), 1.05 (m, 2H).

MS m/z (+ESI): 502.2 [M+H]$^+$.

Example 39

3-oxo-3,4-dihydro-2H-benzo[1,4]thiazine-6-carboxylic acid [1-(8-methoxy-2,3-dihydro-furo[3,2-c]quinolin-2-ylmethyl)-azetidin-3-yl]-amide Preparation of 4-allyloxy-6-methoxy-quinoline Sodium (1.22 g, 52.9 mmol, 2.1 eq) is added portionwise at 0° C. to a stirred solution of allyl alcohol (117.1 g, 201.6 mmol, 80.0 eq). After 30 minutes stirring at 0° C., 4-bromo-6-methoxy-quinoline (6.0 g, 25.2 mmol, 1.0 eq) is added to the reaction mixture that is heated under reflux for 5 hours. The reaction mixture is then cooled down to room temperature, and filtered. The filtrate is evaporated under reduced pressure to give a residue that is extracted with ethyl acetate (3×100 mL) and water (100 mL). The combined organic layers are dried over sodium sulfate, filtered and concentrated to give a crude product that is purified by column chromatography (silica gel, eluent: dichloromethane:methanol, 60:1, v/v) to afford 4-allyloxy-6-methoxy-quinoline as a white solid (4.0 g, 74% yield).

$^1$H-NMR (400 MHz, DMSO-d6) δ ppm: 8.55 (d, J=5.2 Hz, 1H), 7.85 (d, J=9.2 Hz, 1H), 7.41 (d, J=2.4 Hz, 1H), 7.36 (dd, J=2.4, 9.2 Hz, 1H), 6.97 (d, J=5.2 Hz, 1H), 6.15 (m, 1H), 5.51 (d, J=17.2 Hz, 1H), 5.34 (d, J=10.4 Hz, 1H), 4.83 (d, J=5.2 Hz, 2H), 3.87 (s, 3H).

MS m/z (+ESI): 216.1 [M+H]$^+$.

Preparation of 3-allyl-6-methoxy-quinolin-4-ol

A solution of 4-allyloxy-6-methoxy-quinoline (4.0 g, 18.6 mmol, 1.0 eq) in diphenyl oxide (80 mL) is heated at 180° C. for 1 hour. The reaction mixture is then cooled down to room temperature before the addition of petroleum ether (100 mL). The resulting suspension is filtered to afford 3-allyl-6-methoxy-quinolin-4-ol as a light grey solid (1.3 g, 32% yield).

$^1$H-NMR (400 MHz, DMSO-d6) δ ppm: 11.64 (s, 1H), 7.71 (d, J=5.2 Hz, 1H), 7.49 (m, 2H), 7.24 (m, 1H), 5.96 (m, 1H), 5.02 (m, 2H), 3.81 (s, 3H), 3.18 (d, J=6.4 Hz, 2H).

MS m/z (+ESI): 216.1 [M+H]$^+$.

Preparation of 2-bromomethyl-8-methoxy-2,3-dihydro-furo[3,2-c]quinoline

N-Bromosuccinimide (1.19 g, 6.69 mmol, 1.2 eq) is added at 10° C. to a stirred solution of 3-allyl-6-methoxy-quinolin-4-ol (1.20 g, 5.57 mmol, 1.0 eq) in dichloromethane (120 mL) and the resulting mixture is stirred at 10° C. for 1 hour. The reaction mixture is then successively washed with water (50 mL) and brine (20 mL), dried over sodium sulfate, filtered and concentrated to give a crude product that is purified by column chromatography (silica gel, eluent: dichloromethane: methanol, 80:1, v/v) to afford 2-bromomethyl-8-methoxy-2,3-dihydro-furo[3,2-c]quinoline as a light yellow solid (1.2 g, 73% yield).

$^1$H-NMR (400 MHz, DMSO-d6) δ ppm: 8.55 (s, 1H), 7.93 (d, J=9.2 Hz, 1H), 7.30 (dd, J=2.8, 9.6 Hz, 1H), 7.14 (d, J=2.4 Hz, 1H), 5.30 (dd, J=4.8, 10.0 Hz, 1H), 3.93 (s, 3H), 3.62-3.74 (m, 2H), 3.01-3.60 (m, 2H).

MS m/z (+ESI): 294.0, 296.0 [M+H]$^+$.

Preparation of 3-oxo-3,4-dihydro-2H-benzo[1,4]thiazine-6-carboxylic acid [1-(8-methoxy-2,3-dihydro-furo[3,2-c]quinolin-2-ylmethyl)-azetidin-3-yl]-amide The titled compound is prepared as a white lyophilized powder following Scheme 1 and in analogy to Example 1 using 2-bromomethyl-8-methoxy-2,3-dihydro-furo[3,2-c]quinoline, 3-amino-azetidine-1-carboxylic acid tert-butyl ester and 3-oxo-3,4-dihydro-2H-benzo[1,4]thiazine-6-carboxylic acid as starting material.

$^1$H-NMR (400 MHz, DMSO-d6) δ ppm: 10.68 (s, 1H), 8.75 (d, J=6.9 Hz, 1H), 8.55 (s, 1H), 7.86 (d, J=9.3 Hz, 1H), 7.45 (m, 3H), 7.34 (dd, J=2.9, 9.3 Hz, 1H), 7.11 (dd, J=2.8, 9.1 Hz, 1H), 5.16 (m, 1H), 4.46 (m, 1H), 3.89 (s, 3H), 3.76 (m, 1H), 3.44-3.56 (m, 4H), 3.14-3.24 (m, 3H), 2.86 (m, 2H).

MS m/z (+ESI): 477.1 [M+H]$^+$.

Example 45

3-oxo-3,4-dihydro-2H-benzo[1,4]thiazine-6-carboxylic acid [1-(5-fluoro-6-methoxy-3,4-dihydro-2H-1-oxa-9-aza-phenanthren-3-ylmethyl)-piperidin-4-yl]-amide Preparation of 3-chloro-6-methoxy-quinoline-4-carbaldehyde A solution of n-butyllithium (1.6 M in tetrahydrofuran, 0.46 mL, 0.73 mmol, 1.0 eq) is added at −78° C. to a stirred solution of 4-bromo-3-chloro-6-methoxy-quinoline (200 mg, 0.73 mmol, 1.0 eq) in tetrahydrofuran (10 mL). After 2 hours stirring at −78° C., N,N-dimethylformamide (0.3 mL) is added and the reaction mixture is stirred at 60° C. for two hours. Then solvent is evaporated and the residue is extracted with ethyl acetate (3×10 mL) and water (10 mL). The combined organic layers are washed with brine, dried over sodium sulfate, filtered and concentrated to give a crude product that is purified by column chromatography (silica gel, eluent: petroleum ether:ethyl acetate, 5:1, v/v) to afford 3-chloro-6-methoxy-quinoline-4-carbaldehyde as a light yellow solid (78 mg, 48% yield).

$^1$H-NMR (400 MHz, DMSO-d6) δ ppm: 10.69 (s, 1H), 8.87 (s, 1H), 8.14 (s, 1H), 8.00 (d, J=8.8 Hz, 1H), 7.49 (d, J=8.8 Hz, 1H), 3.89 (s, 3H).

MS m/z (+ESI): 222.1 [M+H]$^+$.

Preparation of 3-chloro-5-fluoro-6-methoxy-quinoline-4-carbaldehyde

Selectfluor (2.4 g, 6.77 mmol, 1.5 eq) is added at 10° C. to a stirred solution of 3-chloro-6-methoxy-quinoline-4-carbaldehyde (1.0 g, 4.5 mmol, 1.0 eq) in acetonitrile (50 mL). After 24 hours stirring at 10° C., the reaction mixture is extracted with ethyl acetate (3×100 mL) and brine (50 mL). The combined organic layers are dried over sodium sulfate, filtered and concentrated to give a crude product that is purified by column chromatography (silica gel, eluent: petroleum ether:

ethyl acetate, 10:1 to 5:1, v/v) to afford 3-chloro-5-fluoro-6-methoxy-quinoline-4-carbaldehyde as a yellow solid (620 mg, 57% yield).

$^1$H-NMR (400 MHz, CDCl$_3$) δ ppm: 10.66 (d, J=9.2 Hz, 1H), 8.87 (s, 1H), 8.01 (d, J=9.6 Hz, 1H), 7.92 (t, J=8.8 Hz, 1H), 4.02 (s, 3H).

MS m/z (+ESI): 240.1 [M+H]$^+$.

Preparation of 5-fluoro-3-hydroxy-6-methoxy-quinoline-4-carbaldehyde

Tris(dibenzylideneacetone)dipalladium(0) (40 mg, 0.04 mmol, 0.02 eq) is added at room temperature to a stirred solution of 3-chloro-5-fluoro-6-methoxy-quinoline-4-carbaldehyde (500 mg, 2.10 mmol, 1.0 eq) in dioxane (6 mL), followed by 2-dicyclohexylphosphino-2',4',6'-triisopropylbiphenyl (100 mg, 0.21 mmol, 0.1 eq) and a 1.6 M potassium hydroxide aqueous solution (2 mL). The reaction mixture is irradiated by microwaves at 125° C. for 15 minutes, then water (10 mL) is added, the resulting mixture is neutralized with 2.0 N hydrochloric acid aqueous solution and extracted with ethyl acetate (3×10 mL). The combined organic layers are dried over sodium sulfate, filtered and concentrated to give a crude product that is purified by column chromatography (silica gel, eluent: petroleum ether:ethyl acetate, 5:1, v/v) to afford 5-fluoro-3-hydroxy-6-methoxy-quinoline-4-carbaldehyde as a light yellow solid (168 mg, 36% yield).

$^1$H-NMR (400 MHz, CDCl$_3$) δ ppm: 13.12 (s, 1H), 10.93 (d, J=2.0 Hz, 1H), 8.66 (s, 1H), 7.93 (d, J=9.2 Hz, 1H), 7.38 (t, J=8.8 Hz, 1H), 4.07 (s, 3H).

MS m/z (+ESI): 222.1 [M+H]$^+$.

Preparation of 3-bromomethyl-5-fluoro-6-methoxy-3,4-dihydro-2H-1-oxa-9-aza-phenanthrene The titled compound is prepared as a white solid following procedures described in Example 1 from 5-fluoro-3-hydroxy-6-methoxy-quinoline-4-carbaldehyde.

$^1$H-NMR (400 MHz, CDCl$_3$) δ ppm: 8.41 (s, 1H), 7.80 (d, J=8.8 Hz, 1H), 7.32 (t, J=8.8 Hz, 1H), 4.42 (dd, J=7.6, 10.8 Hz, 1H), 4.13 (dd, J=7.6, 10.8 Hz, 1H), 4.01 (s, 3H), 3.45-3.55 (m, 3H), 3.16-3.23 (m, 1H), 2.53 (m, 1H).

MS m/z (+ESI): 326.1, 328.1 [M+H]$^+$.

Preparation of 3-oxo-3,4-dihydro-2H-benzo[1,4]thiazine-6-carboxylic acid [1-(5-fluoro-6-methoxy-3,4-dihydro-2H-1-oxa-9-aza-phenanthren-3-ylmethyl)-piperidin-4-yl]-amide The titled compound is prepared as a white lyophilized powder following Scheme 1 and in analogy to Example 1 using 3-bromomethyl-5-fluoro-6-methoxy-3,4-dihydro-2H-1-oxa-9-aza-phenanthrene, 4-amino-piperidine-1-carboxylic acid tert-butyl ester and 3-oxo-3,4-dihydro-2H-benzo[1,4]thiazine-6-carboxylic acid as starting material.

MS m/z (+ESI): 537.2 [M+H]$^+$.

Example 49

3-oxo-3,4-dihydro-2H-benzo[1,4]thiazine-6-carboxylic acid [1-(6-methoxy-3,4-dihydro-2H-1-thia-9-aza-phenanthren-3-ylmethyl)-azetidin-3-yl]-amide Preparation of 3-bromomethyl-6-methoxy-3,4-dihydro-2H-1-thia-9-aza-phenanthrene The titled compound is prepared as a light yellow solid following procedures described in Example 1 from 6-methoxy-2H-1-thia-9-aza-phenanthrene-3-carboxylic acid ethyl ester (preparation described in WO2011073378A1).

$^1$H-NMR (400 MHz, DMSO-d6) δ ppm: 8.38 (s, 1H), 7.83 (d, J=9.2 Hz, 1H), 7.28 (d, J=9.2 Hz, 1H), 7.18 (s, 1H), 3.90 (s, 3H), 3.79 (m, 1H), 3.68 (m, 1H), 3.24-3.41 (m, 2H), 3.01 (m, 1H), 2.91 (m, 1H), 2.48 (m, 1H).

MS m/z (+ESI): 324.2, 326.2 [M+H]$^+$.

Preparation of 3-oxo-3,4-dihydro-2H-benzo[1,4]thiazine-6-carboxylic acid [1-(6-methoxy-3,4-dihydro-2H-1-thia-9-aza-phenanthren-3-ylmethyl)-azetidin-3-yl]-amide The titled compound is prepared as an off-white lyophilized powder following Scheme 1 and in analogy to Example 1 using 3-bromomethyl-6-methoxy-3,4-dihydro-2H-1-thia-9-aza-phenanthrene, 3-amino-azetidine-1-carboxylic acid tert-butyl ester and 3-oxo-3,4-dihydro-2H-benzo[1,4]thiazine-6-carboxylic acid as starting material.

$^1$H-NMR (400 MHz, DMSO-d6) δ ppm: 10.69 (br, 1H), 8.79 (d, J=6.8 Hz, 1H), 8.38 (s, 1H), 7.85 (d, J=9.0 Hz, 1H), 7.46 (m, 3H), 7.30 (dd, J=1.9, 9.0 Hz, 1H), 7.23 (s, 1H), 4.49 (m, 1H), 3.94 (s, 3H), 3.66 (t, J=6.9 Hz, 2H), 3.52 (s, 2H), 3.25 (m, 2H), 3.06 (m, 2H), 2.78-2.95 (m, 2H), 2.60 (d, J=6.9 Hz, 2H), 2.18 (m, 1H).

MS m/z (+ESI): 507.1 [M+H]$^+$.

Example 51

3-oxo-3,4-dihydro-2H-benzo[1,4]thiazine-6-carboxylic acid [5-hydroxymethyl-1-(6-methoxy-3,4-dihydro-2H-1-thia-9-aza-phenanthren-3-ylmethyl)-pyrrolidin-3-yl]-amide Preparation of 1-(6-methoxy-3,4-dihydro-2H-1-thia-9-aza-phenanthren-3-ylmethyl)-4-[(3-oxo-3,4-dihydro-2H-benzo[1,4]thiazine-6-carbonyl)-amino]-pyrrolidine-2-carboxylic acid methyl ester The titled compound is prepared as an orange viscous oil following Scheme 1 and in analogy to Example 1 using 3-bromomethyl-6-methoxy-3,4-dihydro-2H-1-thia-9-aza-phenanthrene, 4-amino-pyrrolidine-1,2-dicarboxylic acid 1-tert-butyl ester 2-methyl ester and 3-oxo-3,4-dihydro-2H-benzo[1,4]thiazine-6-carboxylic acid as starting material.

MS m/z (+ESI): 579.4 [M+H]$^+$.

Preparation of 3-oxo-3,4-dihydro-2H-benzo[1,4]thiazine-6-carboxylic acid [5-hydroxymethyl-1-(6-methoxy-3,4-dihydro-2H-1-thia-9-aza-phenanthren-3-ylmethyl)-pyrrolidin-3-yl]-amide Lithium aluminium hydride (2.0 M solution in tetrahydrofuran, 85 µL, 0.17 mmol, 1.1 eq) is cautiously added at room temperature to a stirred solution of 1-(6-methoxy-3,4-dihydro-2H-1-thia-9-aza-phenanthren-3-ylmethyl)-4-[(3-oxo-3,4-dihydro-2H-benzo[1,4]thiazine-6-carbonyl)-amino]-pyrrolidine-2-carboxylic acid methyl ester (110 mg, 0.15 mmol, 1.0 eq) in tetrahydrofuran (5 mL). After 1 hour stirring at room temperature, the reaction mixture is cautiously quenched with ice-water (5 mL) and extracted with dichloromethane (3×10 mL) and water (10 mL). The combined organic layers are dried over sodium sulfate, filtered and concentrated to give a crude product that is purified by preparative HPLC to afford 3-oxo-3,4-dihydro-2H-benzo[1,4]thiazine-6-carboxylic acid [5-hydroxymethyl-1-(6-methoxy- 3,4-dihydro-2H-1-thia-9-aza-phenanthren-3-ylmethyl)-pyrrolidin-3-yl]-amide as an off-white lyophilized powder (14 mg, 16% yield).

MS m/z (+ESI): 551.2 [M+H]$^+$.

Example 54

3-oxo-3,4-dihydro-2H-benzo[1,4]thiazine-6-carboxylic acid [1-(8-methoxy-1,2-dihydro-3-oxa-5,9-diaza-cyclopenta[a]naphthalen-2-ylmethyl)-piperidin-4-yl]-amide Preparation of 8-allyl-7-chloro-2-methoxy-[1,5]naphthyridine Allyltributylstannane (7.3 g, 21.9 mmol, 1.2 eq) is added at room temperature to a stirred solution of 8-bromo-7-chloro-2-methoxy-[1,5]naphthyridine (5.0 g, 18.3 mmol, 1.0 eq) in N,N-dimethylformamide (100 mL), followed by tetrakis(triphenylphosphine)palladium(0) (0.63 g, 0.55 mmol, 0.03 eq) and lithium chloride (2.9 g, 67.6 mmol, 3.7 eq). After 1 hour stirring at 105° C., the reaction mixture is cooled down to room temperature and filtered through decalite. The filtrate is concentrated to give a crude product that is extracted with ethyl acetate (3×100 mL) and a 10% ammonium hydroxide aqueous solution (100 mL). The combined organic layers are washed with brine, dried over sodium sulfate, filtered and concentrated to give a crude product that is purified column chromatography (silica gel, eluent: petroleum ether:ethyl acetate, 30:1, v/v) to afford 8-allyl-7-chloro-2-methoxy-[1,5]naphthyridine as a colorless oil (2.5 g, 58% yield).

MS m/z (+ESI): 235.1 [M+H]$^+$.

Preparation of 3-(3-chloro-6-methoxy-[1,5]naphthyridin-4-yl)-propane-1,2-diol

N-Methylmorpholine-N-oxide (0.76 g, 64.0 mmol, 1.5 eq) is added at room temperature to a stirred solution of 8-allyl-7-chloro-2-methoxy-[1,5]naphthyridine (1.0 g, 4.26 mmol, 1.0 eq) in dichloromethane (40 mL) and water (4 mL), followed by potassium osmium(VI) oxide dihydrate (80 mg, 0.23 mmol, 0.05 eq). After 16 hours stirring at room temperature, the reaction mixture is extracted with dichloromethane (3×20 mL) and a saturated sodium sulfite aqueous solution (20 mL). The combined organic layers are washed with brine, dried over sodium sulfate, filtered and concentrated to give a crude product that is purified by column chromatography (silica gel, eluent: dichloromethane:methanol, 40:1, v/v) to afford 3-(3-chloro-6-methoxy-[1,5]naphthyridin-4-yl)-propane-1,2-diol as a light yellow solid (1.1 g, 96% yield).

$^1$H-NMR (400 MHz, CDCl$_3$) δ ppm: 8.69 (s, 1H), 8.20 (d, J=9.2 Hz, 1H), 7.12 (d, J=9.2 Hz, 1H), 4.10-4.16 (m, 1H), 4.08 (s, 3H), 3.60-3.71 (m, 2H), 3.46-3.56 (m, 2H).

MS m/z (+ESI): 269.1 [M+H]$^+$.

Preparation of 1-(tert-butyl-dimethyl-silanyloxy)-3-(3-chloro-6-methoxy-[1,5]naphthyridin-4-yl)-propan-2-ol Imidazole (760 mg, 11.2 mmol, 3.0 eq) is added at room temperature to a stirred solution of 3-(3-chloro-6-methoxy-[1,5]naphthyridin-4-yl)-propane-1,2-diol (1.0 g, 3.7 mmol, 1.0 eq) in dichloromethane (150 mL) and N,N-dimethylformamide (10 mL), followed by tell-butyldimethylsilyl chloride (1.7 g, 11.2 mmol, 3.0 eq) and 4-dimethylaminopyridine (296 mg, 2.4 mmol, 0.65 eq). After 1 hour stirring at room temperature, the reaction mixture is extracted with dichloromethane (3×100 mL) and water (100 mL). The combined organic layers are washed with brine, dried over sodium sulfate, filtered and concentrated to give a crude product that is purified by column chromatography (silica gel, eluent: petroleum ether:ethyl acetate, 10:1, v/v) to afford 1-(tert-butyl-dimethyl-silanyloxy)-3-(3-chloro-6-methoxy-[1,5]naphthyridin-4-yl)-propan-2-ol as a white solid (0.9 g, 63% yield).

$^1$H-NMR (400 MHz, DMSO-d6) δ ppm: 8.71 (s, 1H), 8.24 (d, J=8.8 Hz, 1H), 7.24 (d, J=8.8 Hz, 1H), 4.75 (d, J=5.6 Hz, 1H), 4.08 (m, 1H), 4.06 (s, 3H), 3.61 (m, 1H), 3.51 (m, 2H), 2.48-3.27 (m, 1H), 0.74 (s, 9H), −0.03 (s, 3H), −0.09 (s, 3H).

MS m/z (+ESI): 383.2 [M+H]$^+$.

Preparation of 2-(tert-butyl-dimethyl-silanyloxymethyl)-8-methoxy-1,2-dihydro-3-oxa-5,9-diaza-cyclopenta[a]naphthalene Cesium carbonate (1.4 g, 4.2 mmol, 2.0 eq) is added at room temperature to a stirred solution of 1-(tert-butyl-dimethyl-silanyloxy)-3-(3-chloro-6-methoxy-[1,5]naphthyridin-4-yl)-propan-2-ol (0.8 g, 2.1 mmol, 1.0 eq) in dioxane (25 mL), followed by palladium(II) acetate (94 mg, 0.42 mmol, 0.2 eq) and racemic-2-di-tert-butylphosphino-1,1'-binaphthyl (175 mg, 0.42 mmol, 0.2 eq). After 3 hours stirring at 105° C., the reaction mixture is cooled down to room temperature and filtered through decalite. The filtrate is concentrated and the residue is extracted with ethyl acetate (3×30 mL) and water (30 mL). The combined organic layers are washed with brine, dried over sodium sulfate, filtered and concentrated to give a crude product that is purified by column chromatography (silica gel, eluent: petroleum ether:ethyl acetate, 10:1, v/v) to afford 2-(tert-butyl-dimethyl-silanyloxymethyl)-8-methoxy-1,2-dihydro-3-oxa-5,9-diaza-cyclopenta[a]naphthalene as a white solid (600 mg, 83% yield).

$^1$H-NMR (400 MHz, DMSO-d6) δ ppm: 8.43 (s, 1H), 8.13 (d, J=9.2 Hz, 1H), 7.00 (d, J=9.2 Hz, 1H), 5.12 (m, 1H), 3.96 (s, 3), 3.90 (m, 1H), 3.80 (m, 1H), 3.49-3.77 (m, 1H), 3.28 (m, 1H), 0.69 (s, 9H), 0.02 (s, 3H), −0.05 (s, 3H).

MS m/z (+ESI): 347.2 [M+H]$^+$.

Preparation of (8-methoxy-1,2-dihydro-3-oxa-5,9-diaza-cyclopenta[a]naphthalene-2-yl)-methanol A 2.0 N hydrochloric acid aqueous solution (5 mL) is added at room temperature to a stirred solution of 2-(tert-butyl-dimethyl-silanyloxymethyl)-8-methoxy-1,2-dihydro-3-oxa-5,9-diaza-cyclopenta[a]naphthalene (600 mg, 1.7 mmol, 1.0 eq) in methanol (20 mL). After 2 hours stirring at room temperature, solvent is removed, the residue is extracted with dichloromethane (3×30 mL) and water (30 mL) and the pH is adjusted to 8 by the addition of a saturated sodium carbonate aqueous solution. The combined organic layers are washed with brine, dried over sodium sulfate, filtered and concentrated to afford (8-methoxy-1,2-dihydro-3-oxa-5,9-diaza-cyclopenta[a]naphthalene-2-yl)-methanol as an off-white solid (400 mg, 99% yield).

$^1$H-NMR (400 MHz, DMSO-d6) δ ppm: 8.44 (s, 1H), 8.15 (d, J=8.8 Hz, 1H), 7.01 (d, J=9.2 Hz, 1H), 5.08 (m, 2H), 3.97 (s, 3H), 3.70 (m, 1H), 3.62 (m, 1H), 3.52 (m, 1H), 2.48-3.12 (m, 1H).

MS m/z (+ESI): 233.2 [M+H]$^+$.

Preparation of 2-bromomethyl-8-methoxy-1,2-dihydro-3-oxa-5,9-diaza-cyclopenta[a]naphthalene The titled compound is prepared as an off-white solid following procedures described in Example 1 from (8-methoxy-1,2-dihydro-3-oxa-5,9-diaza-cyclopenta[a]naphthalene-2-yl)-methanol.

¹H-NMR (400 MHz, CDCl₃) δ ppm: 8.46 (s, 1H), 8.14 (d, J=8.8 Hz, 1H), 6.96 (d, J=9.2 Hz, 1H), 5.28 (m, 1H), 4.06 (s, 3H), 3.68-3.78 (m, 2H), 3.62 (m, 1H), 3.50 (m, 1H).

MS m/z (+ESI): 295.0, 297.0 [M+H]⁺.

Preparation of 3-oxo-3,4-dihydro-2H-benzo[1,4]thiazine-6-carboxylic acid [1-(8-methoxy-1,2-dihydro-3-oxa-5,9-diaza-cyclopenta[a]naphthalen-2-ylmethyl)-piperidin-4-yl]-amide The titled compound is prepared as a white lyophilized powder following Scheme 1 and in analogy to Example 1 using 2-bromomethyl-8-methoxy-1,2-dihydro-3-oxa-5,9-diaza-cyclopenta[a]naphthalene, 4-amino-piperidine-1-carboxylic acid tert-butyl ester and 3-oxo-3,4-dihydro-2H-benzo[1,4]thiazine-6-carboxylic acid as starting material.

¹H-NMR (400 MHz, DMSO-d6) δ ppm: 10.67 (s, 1H), 8.51 (s, 1H), 8.24 (d, J=7.8 Hz, 1H), 8.20 (d, J=9.1 Hz, 1H), 7.44 (m, 3H), 7.07 (d, J=9.1 Hz, 1H), 5.29 (m, 1H), 4.02 (s, 3H), 3.77 (m, 1H), 3.62 (m, 1H), 3.51 (s, 2H), 3.29 (m, 1H), 3.00 (m, 2H), 2.71 (m, 2H), 2.20 (m, 2H), 1.78 (m, 2H), 1.60 (m, 2H).

MS m/z (+ESI): 506.1 [M+H]⁺.

Example 55

3-oxo-3,4-dihydro-2H-benzo[1,4]thiazine-6-carboxylic acid [1-(8-methoxy-1,2-dihydro-furo[2,3-c]quinolin-2-ylmethyl)-piperidin-4-yl]-amide Preparation of 2-bromomethyl-8-methoxy-1,2-dihydro-furo[2,3-c]quinoline The titled compound is prepared as a light yellow solid following procedures described in Examples 1 and 54 from 4-bromo-3-chloro-6-methoxy-quinoline.

¹H-NMR (400 MHz, CDCl₃) δ ppm: 8.48 (s, 1H), 7.96 (d, J=9.2 Hz, 1H), 7.20 (d, J=9.2 Hz, 1H), 6.81 (s, 1H), 5.26 (m, 1H), 3.93 (s, 3H), 3.37-3.73 (m, 4H).

MS m/z (+ESI): 294.0, 296.0 [M+H]⁺.

Preparation of 3-oxo-3,4-dihydro-2H-benzo[1,4]thiazine-6-carboxylic acid [1-(8-methoxy-1,2-dihydro-furo[2,3-c]quinolin-2-ylmethyl)-piperidin-4-yl]-amide The titled compound is prepared as a white lyophilized powder following Scheme 1 and in analogy to Example 1 using 2-bromomethyl-8-methoxy-1,2-dihydro-furo[2,3-c]quinoline, 4-amino-piperidine-1-carboxylic acid tert-butyl ester and 3-oxo-3,4-dihydro-2H-benzo[1,4]thiazine-6-carboxylic acid as starting material.

¹H-NMR (400 MHz, DMSO-d6) δ ppm: 10.67 (s, 1H), 8.45 (s, 1H), 8.24 (d, J=7.7 Hz, 1H), 7.87 (d, J=9.2 Hz, 1H), 7.44 (m, 3H), 7.20 (dd, J=2.8, 9.2 Hz, 1H), 7.07 (d, J=2.8 Hz, 1H), 5.25 (m, 1H), 3.92 (s, 3H), 3.77 (m, 1H), 3.60 (m, 1H), 3.51 (s, 2H), 3.28 (m, 1H), 3.01 (m, 2H), 2.72 (m, 2H), 2.20 (m, 2H), 1.79 (m, 2H), 1.60 (m, 2H).

MS m/z (+ESI): 505.1 [M+H]⁺.

Example 59

3-oxo-3,4-dihydro-2H-benzo[1,4]thiazine-6-carboxylic acid {trans-4-[hydroxy-(8-methoxy-1,2-dihydro-furo[2,3-c]quinolin-2-yl)-methyl]-cyclohexyl}-amide Preparation of 3-(3-chloro-6-methoxy-quinolin-4-yl)-propane-1,2-diol The titled compound is prepared as a grey solid following procedures described in Example 54 from 4-bromo-3-chloro-6-methoxy-quinoline.

MS m/z (+ESI): 268.1 [M+H]⁺.

Preparation of (3-chloro-6-methoxy-quinolin-4-yl)-acetaldehyde

A solution of sodium periodate (2.88 g, 13.5 mmol, 1.2 eq) in water (30 mL) is added dropwise at 0° C. to a stirred solution of 3-(3-chloro-6-methoxy-quinolin-4-yl)-propane-1,2-diol (3.0 g, 11.2 mmol, 1.0 eq) in acetone (50 mL) and water (20 mL). After 30 minutes stirring at 0° C. the reaction mixture is extracted with ethyl acetate (3×100 mL) and water (100 mL). The combined organic layers are washed with brine, dried over sodium sulfate, filtered and concentrated to afford (3-chloro-6-methoxy-quinolin-4-yl)-acetaldehyde as a light brown solid (2.6 g, 99% yield).

¹H-NMR (400 MHz, CDCl₃) δ ppm: 9.78 (t, J=1.6 Hz, 1H), 8.75 (s, 1H), 8.03 (d, J=9.2 Hz, 1H), 7.39 (dd, J=2.4, 9.2 Hz, 1H), 7.02 (d, J=2.4 Hz, 1H), 4.33 (d, J=1.6 Hz, 2H), 3.94 (s, 3H).

MS m/z (+ESI): 236.1 [M+H]⁺.

Preparation of 2-(3-chloro-6-methoxy-quinolin-4-yl)-ethanol

Sodium borohydride (2.09 g, 55.2 mmol, 1.0 eq) is added portionwise at 0° C. to a stirred suspension of (3-chloro-6-methoxy-quinolin-4-yl)-acetaldehyde (13.0 g, 55.2 mmol, 1.0 eq) in ethanol (200 mL). After 1 hour stirring at 0° C., acetone (50 mL) is added to quench the reaction. Solvents are removed and the resulting crude product is purified by column chromatography (silica gel, eluent: dichloromethane:methanol, 50:1, v/v) to afford 2-(3-chloro-6-methoxy-quinolin-4-yl)-ethanol as a yellow solid (13.1 g, 99% yield).

¹H-NMR (400 MHz, CDCl₃) δ ppm: 8.45 (s, 1H), 7.83 (d, J=8.8 Hz, 1H), 7.31 (m, 2H), 4.07 (t, J=6.8 Hz, 2H), 3.97 (s, 3H), 3.47 (t, J=6.8 Hz, 2H).

MS m/z (+ESI): 238.2 [M+H]⁺.

Preparation of 4-(2-bromo-ethyl)-3-chloro-6-methoxy-quinoline

The titled compound is prepared as a light grey solid following procedures described in Example 1 from 2-(3-chloro-6-methoxy-quinolin-4-yl)-ethanol.

¹H-NMR (400 MHz, CDCl₃) δ ppm: 8.70 (s, 1H), 8.03 (d, J=9.2 Hz, 1H), 7.40 (dd, J=2.8, 9.2 Hz, 1H), 7.24 (d, J=2.8 Hz, 1H), 4.00 (s, 3H), 3.76 (m, 2H), 3.64 (m, 2H).

MS m/z (+ESI): 300.0, 302.2 [M+H]⁺.

Preparation of [2-(3-chloro-6-methoxy-quinolin-4-yl)-ethyl]-triphenyl-phosphonium bromide Triphenylphosphine (27.7 g, 106.0 mmol, 3.0 eq) is added at room temperature to a stirred solution of 4-(2-bromoethyl)-3-chloro-6-methoxy-quinoline (10.6 g, 35.3 mmol, 1.0 eq) in p-xylene (200 mL) and the reaction mixture is heated under reflux for 20 hours. The resulting precipitate is collected by filtration and washed with ethyl acetate (50 mL) to afford [2-(3-chloro-6-methoxy-quinolin-4-yl)-ethyl]-triphenyl-phosphonium bromide as a light yellow solid (18.2 g, 92% yield).

$^1$H-NMR (400 MHz, DMSO-d6) δ ppm: 8.74 (s, 1H), 7.82-8.05 (m, 16H), 7.46 (dd, J=2.4, 9.2 Hz, 1H), 6.86 (d, J=2.4 Hz, 1H), 3.94 (m, 2H), 3.79 (s, 3H), 3.35 (m, 2H).

MS m/z (+ESI): 482.2 [M-Br]$^+$.

Preparation of {trans-4-[3-(3-chloro-6-methoxy-quinolin-4-yl)-propenyl]-cyclohexyl}-carbamic acid tert-butyl ester Sodium hexamethyldisilazide (1.0 M in tetrahydrofuran, 3.27 mL, 3.27 mmol, 2.3 eq) is added dropwise at −78° C. to a stirred solution of [2-(3-chloro-6-methoxy-quinolin-4-yl)-ethyl]-triphenyl-phosphonium bromide (800 g, 1.42 mmol, 1.0 eq) in tetrahydrofuran (25 mL). The reaction mixture is then stirred for 45 minutes at −10° C. before lowering down the temperature to −78° C. followed by the addition of (trans-4-formyl-cyclohexyl)-carbamic acid tert-butyl ester (420 mg, 1.85 mmol, 1.3 eq). The reaction mixture is then stirred at 0° C. for 1 hour, extracted with ethyl acetate (3×30 mL) and a saturated ammonium chloride aqueous solution (30 mL). The combined organic layers are washed with brine, dried over sodium sulfate, filtered and concentrated to give a crude product that is purified by column chromatography (silica gel, eluent: petroleum ether:ethyl acetate, 8:1, v/v) to afford {trans-4-[3-(3-chloro-6-methoxy-quinolin-4-yl)-propenyl]-cyclohexyl}-carbamic acid tert-butyl ester as an off-white solid (374 mg, 61% yield).

$^1$H-NMR (400 MHz, CDCl$_3$) δ ppm: 8.68 (s, 1H), 8.00 (d, J=9.2 Hz, 1H), 7.37 (dd, J=2.4, 9.2 Hz, 1H), 7.20 (d, J=2.4 Hz, 1H), 5.31-5.40 (m, 2H), 4.48 (s, 1H), 3.96 (m, 5H), 3.45-3.53 (m, 1H), 2.57 (m, 1H), 2.09 (m, 2H), 1.82 (m, 2H), 1.45 (m, 1H), 1.48 (s, 9H), 1.18-1.35 (m, 3H).

MS m/z (+ESI): 431.3 [M+H]$^+$.

Preparation of {trans-4-[3-(3-chloro-6-methoxy-quinolin-4-yl)-1,2-dihydroxy-propyl]-cyclohexyl}-carbamic acid tert-butyl ester The titled compound is prepared as an off-white solid following procedures described in Example 54 from {trans-4-[3-(3-chloro-6-methoxy-quinolin-4-yl)-propenyl]-cyclohexyl}-carbamic acid tert-butyl ester.

$^1$H-NMR (400 MHz, DMSO-d6) δ ppm: 8.66 (s, 1H), 7.93 (d, J=9.2 Hz, 1H), 7.56 (d, J=2.8 Hz, 1H), 7.42 (dd, J=2.8, 9.2 Hz, 1H), 6.68 (d, J=8.0 Hz, 1H), 4.95 (d, J=5.6 Hz, 1H), 4.66 (d, J=7.2 Hz, 1H), 3.91 (s, 3H), 3.71-3.77 (m, 1H), 3.54 (m, 1H), 3.31 (m, 1H), 3.22 (m, 1H), 3.13 (m, 1H), 1.74-1.83 (m, 2H), 1.65 (m, 1H), 1.57 (m, 2H), 1.36 (m, 1H), 1.38 (s, 9H), 1.03-1.22 (m, 3H.)

MS m/z (+ESI): 465.3 [M+H]$^+$.

Preparation of {trans-4-[hydroxy-(8-methoxy-1,2-dihydro-furo[2,3-c]quinolin-2-yl)-methyl]-cyclohexyl}-carbamic acid tert-butyl ester Cesium carbonate (3.1 g, 9.46 mmol, 2.0 eq) is added at room temperature to a stirred solution of {trans-4-[3-(3-chloro-6-methoxy-quinolin-4-yl)-1,2-dihydroxy-propyl]-cyclohexyl}-carbamic acid tert-butyl ester (2.2 g, 4.73 mmol, 1.0 eq) in dioxane (70 mL), followed by palladium(II) acetate (159 mg, 0.71 mmol, 0.15 eq) and racemic-2-di-tert-butylphosphino-1,1'-binaphthyl (283 mg, 0.71 mmol, 0.15 eq). After 3 hours stirring at 100° C., solvent is removed and the residue is extracted with dichloromethane (3×100 mL) and water (100 mL). The combined organic layers are washed with brine, dried over sodium sulfate, filtered and concentrated to afford {trans-4-[hydroxy-(8-methoxy-1,2-dihydro-furo[2,3-c]quinolin-2-yl)-methyl]-cyclohexyl}-carbamic acid tert-butyl ester as a light grey solid (1.35 g, 67% yield).

$^1$H-NMR (400 MHz, DMSO-d6) δ ppm: 8.39 (s, 1H), 7.82 (d, J=9.2 Hz, 1H), 7.14 (d, J=9.2 Hz, 1H), 7.05 (s, 1H), 6.70 (d, J=7.6 Hz, 1H), 5.02 (m, 2H), 3.88 (s, 3H), 3.53 (m, 1H), 3.42 (m, 2H), 3.15 (m, 1H), 1.87-1.99 (m, 1H), 1.71-1.87 (m, 2H), 1.65 (m, 1H), 1.34 (m, 1H), 1.36 (s, 9H), 1.11-1.24 (m, 4H).

MS m/z (+ESI): 429.3 [M+H]$^+$.

Preparation of 3-oxo-3,4-dihydro-2H-benzo[1,4]thiazine-6-carboxylic acid {trans-4-[hydroxy-(8-methoxy-1,2-dihydro-furo[2,3-c]quinolin-2-yl)-methyl]-cyclohexyl}-amide The titled compound is prepared as a white lyophilized powder following Scheme 5 and in analogy to Example 1 using {trans-4-[hydroxy-(8-methoxy-1,2-dihydro-furo[2,3-c]quinolin-2-yl)-methyl]-cyclohexyl}-carbamic acid tert-butyl ester and 3-oxo-3,4-dihydro-2H-benzo[1,4]thiazine-6-carboxylic acid as starting material.

$^1$H-NMR (400 MHz, DMSO-d6) δ ppm: 10.67 (s, 1H), 8.43 (s, 1H), 8.23 (d, J=7.9 Hz, 1H), 7.86 (d, J=9.2 Hz, 1H), 7.44 (m, 3H), 7.19 (dd, J=2.8, 9.2 Hz, 1H), 7.09 (d, J=2.7 Hz, 1H), 5.09 (m, 2H), 3.92 (s, 3H), 3.71 (m, 1H), 3.60 (m, 1H), 3.49 (m, 4H), 1.99 (m, 1H), 1.92 (m, 2H), 1.75 (m, 1H), 1.50 (m, 1H), 1.22-1.40 (m, 4H).

MS m/z (+ESI): 520.1 [M+H]$^+$.

Example 77

3-oxo-3,4-dihydro-2H-benzo[1,4]thiazine-6-carboxylic acid (3R,6S)-[6-(9-fluoro-8-methoxy-1,2-dihydro-furo[2,3-c]quinolin-2-ylmethyl)-tetrahydro-pyran-3-yl]-amide Preparation of (3-chloro-5-fluoro-6-methoxy-quinolin-4-ylmethyl)-phosphonic acid diethyl ester The titled compound is prepared as an off-white solid following Scheme 3 and in analogy to Examples 1 and 13 using 3-chloro-5-fluoro-6-methoxy-quinoline-4-carbaldehyde as starting material.

$^1$H-NMR (400 MHz, DMSO-d6) δ ppm: 8.74 (s, 1H), 7.84 (m, 2H), 4.01 (s, 3H), 3.94 (m, 6H), 1.08 (m, 6H).

MS m/z (+ESI): 362.1 [M+H]$^+$.

Preparation of (2S,5R)-5-tert-butoxycarbonylamino-tetrahydro-pyran-2-carboxylic acid The titled compound is prepared as a white solid following procedures described in Eur. J. Org. Chem., 2003, 2418-2427 using tri-O-acetyl-D-glucal as starting material.

MS m/z (−ESI): 244.1 µM−Hr.

Preparation of (3R,6S)-[6-(2-diazo-acetyl)-tetrahydro-pyran-3-yl]-carbamic acid tert-butyl ester Ethyl chloroformate (605 µL, 6.36 mmol, 1.2 eq) is added dropwise at 0° C. to a stirred solution of (2S,5R)-5-tertbutoxycarbonylamino-tetrahydro-pyran-2-carboxylic acid (1.3 g, 5.30 mmol, 1.0 eq) and diisopropylethylamine (1.38 mL, 7.95 mmol, 1.5 eq) in tetrahydrofuran (50 mL). After 30 minutes stirring at room temperature the reaction mixture is cooled down to −20° C. before the addition of diazomethane (2.0 M solution in diethyl ether, 26.5 mL, 53.0 mmol, 10.0 eq). After 15 hours stirring at −20° C., the reaction mixture is carefully acidified to pH 6 with 1.0 N hydrochloric acid aqueous solution and then extracted with ethyl acetate (3×30 mL). The combined organic layers are washed with brine, dried over sodium sulfate, filtered and concentrated to give a crude product that is purified by column chromatography (silica gel, eluent: petroleum ether:ethyl acetate, 10:1 to 3:1, v/v) to afford (3R,6S)-[6-(2-diazo-acetyl)-tetrahydro-pyran-3-yl]-carbamic acid tert-butyl ester as a white solid (1.14 g, 80% yield).

MS m/z (+ESI): 214.2 [M−56+H]$^+$.

Preparation of (2S,5R)-(5-tert-butoxycarbonylamino-tetrahydro-pyran-2-yl)-acetic acid methyl ester A solution of silver trifluoroacetate (124 mg, 0.56 mmol, 0.4 eq) in triethylamine (0.5 mL) is added at 0° C. to a stirred solution of (3R,6S)-[6-(2-diazo-acetyl)-tetrahydro-pyran-3-yl]-carbamic acid tert-butyl ester (380 mg, 1.41 mmol, 1.0 eq) in tetrahydrofuran (20 mL) and methanol (20 mL). After 1 hour stirring at room temperature, solvents are removed and the crude product is purified by column chromatography (silica gel, eluent: petroleum ether:ethyl acetate, 10:1 to 3:1, v/v) to afford (2S,5R)-(5-tert-butoxycarbonylamino-tetrahydro-pyran-2-yl)-acetic acid methyl ester as a white solid (200 mg, 52% yield).

MS m/z (+ESI): 218.2 [M−56+H]$^+$.

Preparation of (2S,5R)-(5-tert-butoxycarbonylamino-tetrahydro-pyran-2-yl)-acetic acid Lithium hydroxide monohydrate (61 mg, 1.46 mmol, 2.0 eq) is added at room temperature to a stirred solution of (2S,5R)-(5-tert-butoxycarbonylamino-tetrahydro-pyran-2-yl)-acetic acid methyl ester (200 mg, 0.73 mmol, 1.0 eq) in methanol (10 mL) and water (5 mL) and the resulting mixture is stirred at room temperature for 2 hours. Then solvents are evaporated, the residue is acidified to pH 2 with 2.0 M hydrochloric acid aqueous solution and the resulting aqueous layer is extracted with ethyl acetate (3×20 mL). The combined organic layers are dried over sodium sulfate, filtered and concentrated to afford (2S,5R)-(5-tert-butoxycarbonylamino-tetrahydro-pyran-2-yl)-acetic acid as a colorless oil (150 mg, 79% yield).

$^1$H-NMR (400 MHz, CDCl$_3$) δ ppm: 4.05 (m, 1H), 3.58-3.71 (m, 2H), 3.06 (m, 1H), 2.43-2.59 (m, 2H), 1.27-2.08 (m, 4H), 1.38 (s, 9H).

Preparation of (3R,6S)-[6-(2-hydroxy-ethyl)-tetrahydro-pyran-3-yl]-carbamic acid tert-butyl ester A solution of borane dimethyl sulphide complex in tetrahydrofuran (2.0 M, 289 μL, 0.58 mmol, 3.0 eq) is added dropwise at 0° C. to a stirred solution of (2S,5R)-(5-tert-butoxycarbonylamino-tetrahydro-pyran-2-yl)-acetic acid (50 mg, 0.19 mmol, 1.0 eq) in tetrahydrofuran (2 mL). The reaction mixture is stirred at 0° C. for 30 minutes then at room temperature for 2 hours. Methanol (2 mL) is cautiously added to the reaction mixture that is then evaporated, repeatedly treated with methanol and concentrated to dryness to afford (3R,6S)-[6-(2-hydroxy-ethyl)-tetrahydro-pyran-3-yl]-carbamic acid tert-butyl ester as a white solid (47 mg, 99% yield).

$^1$H-NMR (400 MHz, DMSO-d6) δ ppm: 6.75 (d, J=8.2 Hz, 1H), 4.37 (t, J=5.0 Hz, 1H), 3.75 (m, 1H), 3.44 (m, 2H), 3.25 (m, 2H), 2.91 (m, 1H), 1.85 (m, 1H), 1.20-1.70 (m, 5H), 1.38 (s, 9H).

MS m/z (+ESI): 190.1 [M−56+H]$^+$.

Preparation of (3R,6S)-[6-(2-oxo-ethyl)-tetrahydro-pyran-3-yl]-carbamic acid tert-butyl ester Dess-Martin periodinane (162 mg, 0.38 mmol, 2.0 eq) is added dropwise at 0° C. to a stirred solution of (3R,6S)-[6-(2-hydroxy-ethyl)-tetrahydro-pyran-3-yl]-carbamic acid tert-butyl ester (47 mg, 0.19 mmol, 1.0 eq) in dichloromethane (3 mL). The reaction mixture is stirred 0° C. for 30 minutes then at room temperature for 1 hour. Then a saturated sodium thiosulfate aqueous solution (2 mL) is added, followed by a saturated sodium hydrogen carbonate aqueous solution (2 mL). The resulting mixture is stirred for 30 minutes and extracted with dichloromethane (3×10 mL). The combined organic layers are dried over sodium sulfate, filtered and concentrated to give a crude product that is purified by column chromatography (silica gel, eluent: n-hexane:ethyl acetate, 10:1 to 1:1, v/v) to afford (3R,6S)-[6-(2-oxo-ethyl)-tetrahydro-pyran-3-yl]-carbamic acid tert-butyl ester as a white solid (20 mg, 43% yield).

MS m/z (+ESI): 188.1 [M−56+H]$^+$.

Preparation of (3R,6S)-{6-[3-(3-chloro-5-fluoro-6-methoxy-quinolin-4-yl)-allyl]-tetrahydro-pyran-3-yl}-carbamic acid tert-butyl ester A solution of n-butyllithium (1.6 M in n-hexane, 4.72 mL, 7.55 mmol, 1.5 eq) is added dropwise at 0° C. to a stirred solution of (3-chloro-5-fluoro-6-methoxy-quinolin-4-ylmethyl)-phosphonic acid diethyl ester (1.82 g, 5.03 mmol, 1.0 eq) in tetrahydrofuran (130 mL). After 2 hours stirring at 0° C., a solution of (3R,6S)-[6-(2-oxo-ethyl)-tetrahydro-pyran-3-yl]-carbamic acid tert-butyl ester (1.22 g, 5.03 mmol, 1.0 eq) in tetrahydrofuran (30 mL) is added dropwise within 2 minutes. After 10 minutes stirring at 0° C., the reaction mixture is quenched with water (10 mL). Then solvent is evaporated and the residue is extracted with ethyl acetate (3×150 mL) and water (100 mL). The combined organic layers are washed with brine, dried over sodium sulfate, filtered and concentrated to give a crude product that is purified by column chromatography (silica gel, eluent: n-hexane:ethyl acetate, 10:1 to 1:1, v/v) to afford (3R,6S)-{6-[3-(3-chloro-5-fluoro-6-methoxy-quinolin-4-yl)-allyl]-tetrahydro-pyran-3-yl}-carbamic acid tert-butyl ester as a light red solid (1.82 g, 80% yield).

MS m/z (+ESI): 451.2 [M+H]$^+$.

Preparation of (3R,6S)-{[6-[3-(3-chloro-5-fluoro-6-methoxy-quinolin-4-yl)-2,3-dihydroxy-propyl]-tetrahydro-pyran-3-yl}-carbamic acid tert-butyl ester A solution of osmium tetroxide (482 mg, 1.89 mmol, 0.3 eq) in tert-butanol (10 mL) is added dropwise at room temperature to a stirred solution of (3R,6S)-{6-[3-(3-chloro-5-fluoro-6-methoxy-quinolin-4-yl)-allyl]-tetrahydro-pyran-3-yl}-carbamic acid tert-butyl ester (2.85 g, 6.32 mmol, 1.0 eq) in tetrahydrofuran (40 mL), tert-butanol (40 mL) and water (4 mL), followed by N-methylmorpholine-N-oxide (2.22 g, 18.96 mmol, 3.0 eq). After 16 hours stirring at 40° C., the reaction mixture is quenched with a saturated sodium thiosulfate aqueous solution (50 mL) and brine (50 mL). The resulting mixture is stirred for 30 minutes and extracted with dichloromethane (3×100 mL). The combined organic layers are dried over sodium sulfate, filtered and concentrated to give a crude product that is purified by column chromatography (silica gel, eluent: n-hexane:ethyl acetate, 5:1 to 1:1, v/v) to afford (3R,6S)-{[6-[3-(3-chloro-5-fluoro-6-methoxy-quinolin-4-yl)-2,3-dihydroxy-propyl]-tetrahydro-pyran-3-yl}-carbamic acid tert-butyl ester as a light yellow foam (2.40 g, 78% yield).

MS m/z (+ESI): 485.1 [M+H]$^+$.

Preparation of (3R,6S)-[6-(9-fluoro-1-hydroxy-8-methoxy-1,2-dihydro-furo[2,3-c]quinolin-2-ylmethyl)-tetrahydro-pyran-3-yl]-carbamic acid tert-butyl ester Potassium tert-butoxide (231 mg, 2.06 mmol, 2.0 eq) is added at room temperature to a stirred solution of (3R,6S)-{[6-[3-(3-chloro-5-fluoro-6-methoxy-quinolin-4-yl)-2,3-dihydroxy-propyl]-tetrahydro-pyran-3-yl}-carbamic acid tert-butyl ester (500 mg, 1.03 mmol, 1.0 eq) in dioxane (50 mL), followed by palladium(II) acetate (93 mg, 0.41 mmol, 0.4 eq) and racemic-2-di-tert-butylphosphino-1,1'-binaphthyl (164 mg, 0.41 mmol, 0.4 eq). After 16 hours stirring at 100° C., the reaction mixture is cooled down to room temperature and filtered through decalite. The filtrate is concentrated and the crude product is purified by column chromatography (silica gel, eluent: n-hexane:ethyl acetate, 5:1, v/v) to afford (3R,6S)-[6-(9-fluoro-1-hydroxy-8-methoxy-1,2-dihydro-furo[2,3-c]quinolin-2-ylmethyl)-tetrahydro-pyran-3-yl]-carbamic acid tert-butyl ester as a yellow solid (260 mg, 56% yield).

MS m/z (+ESI): 449.2 [M+H]$^+$.

Preparation of acetic acid 2-(2S,5R)-(5-tert-butoxycarbonylamino-tetrahydro-pyran-2-ylmethyl)-9-fluoro-8-methoxy-1,2-dihydro-furo[2,3-c]quinolin-1-yl ester 4-Dimethylaminopyridine (16 mg, 0.13 mmol, 0.5 eq) and triethylamine (112 µL, 0.80 mmol, 3.0 eq) are added at 0° C. to a stirred solution of (3R,6S)-[6-(9-fluoro-1-hydroxy-8-methoxy-1,2-dihydro-furo[2,3-c]quinolin-2-ylmethyl)-tetrahydro-pyran-3-yl]-carbamic acid tert-butyl ester (120 mg, 0.27 mmol, 1.0 eq) in dichloromethane (10 mL), followed by acetic anhydride (38 µL, 0.40 mmol, 1.5 eq). After 1 hour stirring at 0° C., the reaction mixture is quenched with ethanol (1 mL), solvents are evaporated to give a crude product that is purified by column chromatography (silica gel, eluent: n-hexane:ethyl acetate, 5:1 to 1:1, v/v) to afford acetic acid 2-(2S,5R)-(5-tert-butoxycarbonylamino-tetrahydro-pyran-2-ylmethyl)-9-fluoro-8-methoxy-1,2-dihydro-furo[2,3-c]quinolin-1-yl ester as a light yellow solid (89 mg, 68% yield).

MS m/z (+ESI): 491.2 [M+H]$^+$.

Preparation of (3R,6S)-[6-(9-fluoro-8-methoxy-1,2-dihydro-furo[2,3-c]quinolin-2-ylmethyl)-tetrahydro-pyran-3-yl]-carbamic acid tert-butyl ester 2,3-Dichloro-5,6-dicyano-1,4-benzoquinone (833 mg, 3.67 mmol, 5.0 eq) is added at room temperature to a stirred solution of acetic acid 2-(2S,5R)-(5-tert-butoxycarbonylamino-tetrahydro-pyran-2-ylmethyl)-9-fluoro-8-methoxy-1,2-dihydro-furo[2,3-c]quinolin-1-yl ester (360 mg, 0.73 mmol, 1.0 eq) in toluene (60 mL). After 2 hours stirring at room temperature, solvent is evaporated and the residue is extracted with dichloromethane (3×100 mL) and a saturated sodium carbonate aqueous solution (100 mL). The combined organic layers are dried over sodium sulfate, filtered and concentrated to give a crude product that is purified by column chromatography (silica gel, eluent: n-hexane:ethyl acetate, 10:1 to 1:1, v/v) to afford (3R,6S)-[6-(9-fluoro-8-methoxy-1,2-dihydro-furo[2,3-c]quinolin-2-ylmethyl)-tetrahydro-pyran-3-yl]-carbamic acid tert-butyl ester as a light yellow solid (75 mg, 24% yield).

$^1$H-NMR (400 MHz, DMSO-d6) δ ppm: 8.56 (s, 1H), 7.83 (d, J=9.4 Hz, 1H), 7.59 (t, J=9.0 Hz, 1H), 6.81 (m, 1H), 5.17 (m, 1H), 3.99 (s, 3H), 3.81 (m, 2H), 3.39 (m, 3H), 2.89 (m, 1H), 1.30-2.50 (m, 6H), 1.39 (s, 9H).

MS m/z (+ESI): 433.3 [M+H]$^+$.

Preparation of 3-oxo-3,4-dihydro-2H-benzo[1,4]thiazine-6-carboxylic acid (3R,6S)-[6-(9-fluoro-8-methoxy-1,2-dihydro-furo[2,3-c]quinolin-2-ylmethyl)-tetrahydro-pyran-3-yl]-amide The titled compound is prepared as an off-white lyophilized powder following Scheme 3 and in analogy to Example 13 using (3R,6S)-[6-(9-fluoro-8-methoxy-1,2-dihydro-furo[2,3-c]quinolin-2-ylmethyl)-tetrahydro-pyran-3-yl]-carbamic acid tert-butyl ester and 3-oxo-3,4-dihydro-2H-benzo[1,4]thiazine-6-carboxylic acid as starting material.

$^1$H-NMR (400 MHz, DMSO-d6) δ ppm: 10.68 (s, 1H), 8.54 (s, 1H), 8.20 (d, J=7.8 Hz, 1H), 7.82 (dd, J=1.4, 9.3 Hz, 1H), 7.57 (t, J=9.2 Hz, 1H), 7.40-7.48 (m, 3H), 5.19 (m, 1H), 3.99 (s, 3H), 3.77-3.87 (m, 4H), 3.51 (s, 2H), 3.44 (m, 1H), 3.15 (m, 1H), 2.08 (m, 1H), 1.83-2.00 (m, 3H), 1.63 (m, 1H), 1.45 (m, 1H).

MS m/z (+ESI): 524.2 [M+H]$^+$.

The examples listed in the following table are prepared using procedures previously described:

| Example Number | Reference Scheme | Reference Example for Preparation | 1H-NMR (400 MHz, DMSO- d6) δ ppm | MS m/z (+ESI) |
|---|---|---|---|---|
| 2 | 1 | 1 | 11.37 (br, 1H), 8.42 (s, 1H), 8.17 (d, J = 8.9 Hz, 1H), 7.87 (d, J = 8.1 Hz, 1H), 7.62 (d, J = 8.1 Hz, 1H), 7.47 (d, J = 8.1 Hz, 1H), 7.07 (d, J = 9.0 Hz, 1H), 4.75 (s, 2H), 4.41 (d, J = 10.7 Hz, 1H), 4.02 (m, 4H), 3.81 (m, 1H), 3.28 (m, 1H), 2.78-2.95 (m, 2H), 2.74 (m, 1H), 2.40 (m, 3H), 2.07-2.25 (m, 2H), 1.88 (m, 2H), 1.58 (m, 2H) | 505.6 [M + H]$^+$ |
| 3 | 1 | 1 | 10.81 (s, 1H), 8.41 (s, 1H), 8.17 (d, J = 9.0 Hz, 2H), 7.46 (dd, J = 2.1, 8.4 Hz, 1H), 7.42 (d, J = 2.0 Hz, 1H), 7.07 (d, J = 9.0 Hz, 1H), 7.00 (d, J = | 504.6 [M + H]$^+$ |

-continued

| Example Number | Reference Scheme | Reference Example for Preparation | 1H-NMR (400 MHz, DMSO-d6) δ ppm | MS m/z (+ESI) |
|---|---|---|---|---|
| | | | 8.3 Hz, 1H), 4.64 (s, 2H), 4.40 (d, J = 10.7 Hz, 1H), 4.01 (m, 4H), 3.76 (m, 1H), 3.28 (m, 1H), 2.85-3.00 (m, 2H), 2.72 (m, 1H), 2.37 (m, 3H), 1.96-2.13 (m, 2H), 1.79 (m, 2H), 1.61 (m, 2H) | |
| 4 | 1 | 1 | 11.01 (br, 1H), 8.42 (s, 1H), 8.17 (d, J = 8.9 Hz, 1H), 8.05 (d, J = 8.1 Hz, 1H), 7.97 (d, J = 7.9 Hz, 1H), 7.60 (d, J = 7.9 Hz, 1H), 7.07 (d, J = 9.0 Hz, 1H), 4.41 (d, J = 10.9 Hz, 1H), 4.02 (m, 4H), 3.80 (m, 1H), 3.66 (s, 2H), 3.28 (m, 1H), 2.70-2.95 (m, 3H), 2.40 (m, 3H), 2.07-2.25 (m, 2H), 1.88 (m, 2H), 1.57(m, 2H) | 521.6 [M + H]+ |
| 5 | 1 | 1 | 11.41 (br, 1H), 8.42 (s, 1H), 8.17 (d, J = 8.9 Hz, 1H), 7.99 (d, J = 8.1 Hz, 1H), 7.62 (d, J = 8.1 Hz, 1H), 7.48 (d, J = 8.1 Hz, 1H), 7.06 (d, J = 8.9 Hz, 1H), 4.76 (s, 2H), 4.44 (m, 2H), 4.04 (m, 1H), 3.97 (s, 3H), 3.28 (m, 1H), 2.88 (m, 1H), 2.74 (m, 2H), 2.55 (m, 2H), 2.20-2.50 (m, 4H), 1.66 (m, 1H) | 491.6 [M + H]+ |
| 6 | 1 | 1 | 10.68 (s, 1H), 8.47 (t, J = 7.0 Hz, 1H), 8.41 (s, 1H), 8.17 (d, J = 8.9 Hz, 1H), 7.47 (m, 3H), 7.07 (dd, J = 1.6, 8.9 Hz, 1H), 4.43 (m, 2H), 4.03 (m, 4H), 3.52 (s, 2H), 3.28 (m, 1H), 2.40-2.97 (m, 7H, overlaps with DMSO peak), 2.34 (m, 1H), 2.17 (m, 1H), 1.80 (m, 1H) | 506.5 [M + H]+ |
| 7 | 1 | 1 | 10.67 (s, 1H), 8.41 (d, J = 0.5 Hz, 1H), 8.17 (dd, J = 0.5, 8.9 Hz, 2H), 7.43 (m, 3H), 7.06 (dd, J = 1.2, 9.0 Hz, 1H), 4.41 (d, J = 9.6 Hz, 1H), 4.02 (m, 5H), 3.51 (s, 2H), 3.28 (m, 1H), 2.67-3.00 (m, 3H), 2.39 (m, 3H), 1.86-2.08 (m, 2H), 1.68-1.86 (m, 2H), 1.57 (m, 1H), 1.39 (m, 1H) | 520.6 [M + H]+ |
| 8 | 1 | 1 | 8.41 (s, 1H), 8.17 (d, J = 8.9 Hz, 1H), 8.07 (d, J = 7.7 Hz, 1H), 7.40 (m, 2H), 7.07 (d, J = 9.0 Hz, 1H), 6.91 (d, J = 8.3 Hz, 1H), 4.40 (d, J = 10.7 Hz, 1H), 4.29 (m, 4H), 4.01 (m, 4H), 3.76 (m, 1H), 3.28 (m, 1H), 2.85-3.00 (m, 2H), 2.74 (m, 1H), 2.36 (m, 3H), 1.95-2.12 (m, 2H), 1.78 (m, 2H), 1.61 (m, 2H) | 491.6 [M + H]+ |
| 9 | 1 | 1 | 8.73 (d, J = 8.0 Hz, 1H), 8.41 (s, 1H), 8.17 (d, J = 8.9 Hz, 1H), 7.89 (dd, J = 1.2, 5.0 Hz, 1H), 7.81 (dd, J = 1.2, 3.6 Hz, 1H), 7.29 (dd, J = 3.7, 5.0 Hz, 1H), 7.20 (s, 1H), 7.07 (d, J = 8.9 Hz, 1H), 4.40 (d, J = 10.7 Hz, 1H), 4.02 (m, 4H), 3.79 (m, 1H), 3.28 (m, 1H), 2.85-3.02 (m, 2H), 2.74 (m, 1H), 2.36 (m, 3H), 1.98-2.12 (m, 2H), 1.79 (m, 2H), 1.67 (m, 2H) | 506.5 [M + H]+ |
| 10 | 1 | 1 | 10.67 (br, 1H), 8.45 (t, J = 5.7 Hz, 1H), 8.40 (s, 1H), 8.16 (d, J = 8.9 Hz, 1H), 7.43 (m, 3H), 7.06 (d, J = 8.9 Hz, 1H), 4.39 (d, J = 10.7 Hz, 1H), 4.00 (m, 4H), 3.51 (s, 2H), 3.25 (m, 1H), 3.16 (t, J = 6.2 Hz, 2H), 2.82-2.95 (m, 2H), 2.71 (m, 1H), 2.36 (m, 3H), 1.83-2.00 (m, 2H), 1.67 (m, 2H), 1.56 (m, 1H), 1.23 (m, 2H) | 534.6 [M + H]+ |
| 11 | 1 | 1 | 10.67 (d, J = 2.8 Hz, 1H), 8.44 (m, 1H), 8.39 (s, 1H), 8.16 (d, J = 8.9 Hz, 1H), 7.42 (m, 3H), 7.05 (d, J = 8.9 Hz, 1H), 4.37 (d, J = 10.4 Hz, 1H), 3.99 (m, 4H), 3.49 (s, 2H), 3.20 (m, 3H), 2.67-2.87 (m, 3H), 2.35 (m, 3H), 1.75-2.07 (m, 3H), 1.68 (m, 2H), 1.47 (m, 1H), 0.99 (m, 1H) | 534.6 [M + H]+ |

-continued

| Example Number | Reference Scheme | Reference Example for Preparation | 1H-NMR (400 MHz, DMSO-d6) δ ppm | MS m/z (+ESI) |
|---|---|---|---|---|
| 12 | 1 | 1 | 10.69 (s, 1H), 8.78 (d, J = 6.9 Hz, 1H), 8.41 (s, 1H), 8.17 (d, J = 8.9 Hz, 1H), 7.47 (m, 3H), 7.07 (d, J = 8.9 Hz, 1H), 4.49 (m, 1H), 4.38 (m, 1H), 4.02 (m, 4H), 3.65 (m, 2H), 3.52 (s, 2H), 3.26 (m, 3H), 3.04 (m, 2H), 2.78 (dd, J = 8.1, 18.0 Hz, 1H), 2.16 (m, 1H) | 492.5 [M + H]+ |
| 14 | 3 | 13 | — | 489.5 [M + H]+ |
| 15 | 1 | 1 | 11.23 (br, 1H), 10.78 (s, 1H), 8.44 (s, 1H), 8.17 (m, 2H), 7.66 (dd, J = 1.8, 8.1 Hz, 1H), 7.56 (s, 1H), 7.46 (d, J = 8.1 Hz, 1H), 7.30 (br, 1H), 7.09 (d, J = 9.0 Hz, 1H), 4.34 (m, 1H), 4.09 (m, 1H), 4.00 (m, 5H), 3.55 (s, 2H), 3.27 (m, 1H), 2.91 (dd, J = 7.4, 17.9 Hz, 1H), 2.69 (m, 1H) | 531.5 [M + H]+ |
| 16 | 3 | 13 | 11.39 (br, 1H), 8.49 (s, 1H), 8.19 (d, J = 9.0 Hz, 1H), 7.75 (d, J = 8.3 Hz, 1H), 7.63 (d, J = 8.1 Hz, 1H), 7.48 (d, J = 8.1 Hz, 1H), 7.06 (d, J = 9.1 Hz, 1H), 5.21 (m, 1H), 4.75 (s, 2H), 4.01 (s, 3H), 3.74 (m, 2H), 3.15 (dd, J = 7.9, 16.8 Hz, 1H), 1.95 (m, 3H), 1.85 (m, 2H), 1.67 (m, 2H), 1.34 (m, 2H), 1.17 (m, 2H) | 490.5 [M + H]+ |
| 19 | 1 | 1 | — | 563.2 [M + H]+ |
| 21 | 1 | 1 | — | 519.2 [M + H]+ |
| 22 | 1 | 1 | — | 505.1 [M + H]+ |
| 23 | 1 | 1 | 10.67 (s, 1H), 8.34 (s, 1H), 8.17 (d, J = 8.0 Hz, 1H), 7.84 (d, J = 9.1 Hz, 1H), 7.43 (m, 3H), 7.22 (ddd, J = 0.7, 2.7, 9.1 Hz, 1H), 7.13 (dd, J = 2.7, 6.4 Hz, 1H), 4.37 (m, 1H), 3.98 (m, 2H), 3.93 (2s, 3H), 3.51 (2s, 2H), 3.12 (m, 1H), 2.64-2.98 (m, 3H), 2.41 (m, 3H), 1.86-2.08 (m, 2H), 1.68-1.86 (m, 2H), 1.57 (m, 1H), 1.39 (m, 1H) | 519.2 [M + H]+ |
| 24 | 1 | 1 | 10.68 (d, J = 1.7 Hz, 1H), 8.48 (dd, J = 2.2, 6.8 hz, 1H), 8.34 (d, J = 1.0 Hz, 1H), 7.84 (d, J = 9.1 Hz, 1H), 7.45 (m, 3H), 7.22 (dd, J = 2.7, 9.1 Hz, 1H), 7.14 (dd, J = 2.7, 5.8 Hz, 1H), 4.40 (m, 2H), 4.00 (dd, J = 7.9, 10.5 Hz, 1H), 3.92 (2s, 3H), 3.53 (2s, 2H), 3.16 (m, 1H), 2.85 (m, 1H), 2.33-2.78 (m, 7H, overlaps with DMSO peak, 2.18 (m, 1H), 1.81 (m, 1H) | 505.2 [M + H]+ |
| 25 | 1 | 1 | — | 491.2 [M + H]+ |
| 26 | 1 | 1 | 10.67 (d, J = 3.8 Hz, 1H), 8.44 (m, 1H), 8.33 (d, J = 4.6 Hz, 1H), 7.83 (dd, J = 0.9, 9.1 Hz, 1H), 7.42 (m, 3H), 7.21 (ddd, J = 0.8, 2.7, 9.1 Hz, 1H), 7.12 (d, J = 2.7 Hz, 1H), 4.35 (d, J = 10.4 Hz, 1H), 3.97 (m, 1H), 3.94 (2s, 3H), 3.49 (2s, 2H), 3.20 (m, 2H), 3.10 (m, 1H), 2.62-2.87 (m, 3H), 2.37 (m, 3H), 1.75-2.07 (m, 3H), 1.68 (m, 2H), 1.53 (m, 1H), 1.01 (m, 1H) | 533.3 [M + H]+ |
| 27 | 1 | 1 | 8.72 (d, J = 8.0 Hz, 1H), 8.35 (s, 1H), 7.89 (dd, J = 1.2, 5.0 Hz, 1H), 7.84 (d, J = 9.1 Hz, 1H), 7.80 (dd, J = 1.2, 3.6 Hz, 1H), 7.28 (dd, J = 3.7, 5.0 Hz, 1H), 7.22 (m, 2H), 7.15 (d, J = 2.7 Hz, 1H), 4.36 (d, J = 10.7 Hz, 1H), 3.98 (m, 1H), 3.93 (2s, 3H), 3.79 (m, 1H), 3.13 (m, 1H), 2.87-3.02 (m, 2H), 2.69 (m, 1H), 2.39 (m, 3H), 1.97-2.12 (m, 2H), 1.80 (m, 2H), 1.67 (m, 2H) | 505.2 [M + H]+ |
| 28 | 1 | 1 | 8.35 (s, 1H), 8.08 (d, J = 7.7 Hz, 1H), 7.84 (d, J = 9.1 Hz, 1H), 7.40 (m, 2H), 7.22 (dd, J = 2.7, 9.1 Hz, 1H), 7.14 (d, J = 2.7 Hz, 1H), 6.91 (d, J = 8.3 Hz, 1H), 4.37 (d, J = 9.5 Hz, 1H), 4.29 (m, 4H), 3.98 (m, 1H), 4.01 (s, | 490.2 [M + H]+ |

-continued

| Example Number | Reference Scheme | Reference Example for Preparation | 1H-NMR (400 MHz, DMSO-d6) δ ppm | MS m/z (+ESI) |
|---|---|---|---|---|
| | | | 3H), 3.77 (m, 1H), 3.12 (m, 1H), 2.87-3.02 (m, 2H), 2.69 (m, 1H), 2.40 (m, 3H), 1.95-2.12 (m, 2H), 1.78 (m, 2H), 1.62 (m, 2H) | |
| 29 | 1 | 1 | 10.67 (s, 1H), 8.35 (s, 1H), 8.26 (d, J = 7.6 Hz, 1H), 7.84 (d, J = 9.1 Hz, 1H), 7.45 (m, 3H), 7.23 (dd, J = 2.7, 9.0 Hz, 1H), 7.15 (d, J = 2.7 Hz, 1H), 4.37 (d, J = 10.4 Hz, 1H), 3.98 (m, 1H), 3.93 (s, 3H), 3.78 (m, 1H), 3.51 (s, 2H), 3.13 (m, 1H), 2.87-3.05 (m, 2H), 2.69 (m, 1H), 2.40 (m, 3H), 1.97-2.13 (m, 2H), 1.79 (m, 2H), 1.63 (m, 2H) | 519.2 [M + H]+ |
| 30 | 1 | 1 | 10.81 (s, 1H), 8.35 (s, 1H), 8.17 (d, J = 7.8 Hz, 1H), 7.84 (d, J = 9.1 Hz, 1H), 7.46 (dd, J = 2.1, 8.4 Hz, 1H), 7.42 (d, J = 2.0 Hz, 1H), 7.23 (dd, J = 2.7, 9.1 Hz, 1H), 7.15 (d, J = 2.7 Hz, 1H), 7.00 (d, J = 8.4 Hz, 1H), 4.64 (s, 2H), 4.37 (d, J = 10.4 Hz, 1H), 3.98 (m, 1H), 3.93 (s, 3H), 3.78 (m, 1H), 3.12 (m, 1H), 2.87-3.02 (m, 2H), 2.68 (m, 1H), 2.40 (m, 3H), 1.96-2.13 (m, 2H), 1.79 (m, 2H), 1.62 (m, 2H) | 503.2 [M + H]+ |
| 32 | 3 | 18 | 10.90 (br, 1H), 8.48 (s, 1H), 8.18 (d, J = 9.1 Hz, 1H), 7.31 (d, J = 8.1 Hz, 1H), 7.04 (m, 2H), 5.18 (m, 1H), 4.62 (s, 2H), 4.00 (s, 3H), 3.72 (s, 2H), 3.67 (m, 1H), 3.14 (dd, J = 7.9, 16.8 Hz, 1H), 2.35 (m, 1H), 1.75-2.00 (m, 5H), 1.55-1.65 (m, 2H), 1.05 (m, 4H) | 476.2 [M + H]+ |
| 33 | 3 | 18 | 10.50 (s, 1H), 8.48 (s, 1H), 8.18 (d, J = 9.1 Hz, 1H), 7.24 (d, J = 7.9 Hz, 1H), 7.05 (d, J = 9.1 Hz, 1H), 6.97 (m, 2H), 5.18 (m, 1H), 4.00 (s, 3H), 3.66 (m, 3H), 3.44 (s, 2H), 3.11 (dd, J = 7.9, 16.8 Hz, 1H), 2.34 (m, 1H), 1.75-2.00 (m, 5H), 1.55-1.65 (m, 2H), 1.04 (m, 4H) | 491.2 [M + H]+ |
| 35 | 1 | 18 | — | 489.3 [M + H]+ |
| 37 | 1 | 1 | 8.40 (d, J = 7.7 Hz, 1H), 8.35 (s, 1H), 8.14 (d, J = 0.5 Hz, 1H), 7.85 (m, 2H), 7.50 (dd, J = 0.6, 5.3 Hz, 1H), 7.23 (dd, J = 2.7, 9.1 Hz, 1H), 7.15 (d, J = 2.7 Hz, 1H), 4.38 (m, 1H), 3.98 (m, 1H), 3.93 (s, 3H), 3.77 (m, 1H), 3.14 (m, 1H), 2.88-3.04 (m, 2H), 2.70 (m, 1H), 2.42 (m, 3H), 1.97-2.15 (m, 2H), 1.84 (m, 2H), 1.64 (m, 2H) | 494.2 [M + H]+ |
| 38 | 1 | 1 | — | 504.3 [M + H]+ |
| 40 | 1 | 1 | 10.67 (s, 1H), 8.55 (s, 1H), 8.24 (d, J = 7.7 Hz, 1H), 7.87 (d, J = 9.3 Hz, 1H), 7.44 (m, 3H), 7.33 (dd, J = 2.9, 9.3 Hz, 1H), 7.12 (dd, J = 2.8, 9.1 Hz, 1H), 5.33 (m, 1H), 3.90 (s, 3H), 3.76 (m, 1H), 3.51 (m, 3H), 3.20 (m, 1H), 2.94-3.08 (m, 2H), 2.81 (m, 1H), 2.70 (m, 1H), 2.22 (m, 2H), 1.78 (m, 2H), 1.60 (m, 2H) | 505.2 [M + H]+ |
| 41 | 4 | 36 | 10.66 (s, 1H), 8.34 (s, 1H), 8.23 (d, J = 7.9 Hz, 1H), 7.84 (d, J = 9.0 Hz, 1H), 7.44 (m, 3H), 7.21 (m, 2H), 4.33 (m, 1H), 3.94 (s, 3H), 3.85 (m, 1H), 3.74 (m, 1H), 3.51 (s, 2H), 3.19 (m, 1H), 2.59 (m, 1H), 2.22 (m, 1H), 1.88 (m, 4H), 1.53 (m, 1H), 1.29-1.48 (m, 4H), 1.05 (m, 2H) | 518.2 [M + H]+ |
| 42 | 2 | 31 | 10.81 (s, 1H), 10.74 (s, 1H), 8.39 (s, 1H), 7.86 (d, J = 9.1 Hz, 1H), 7.66 (dd, J = 1.8, 8.2 Hz, 1H), 7.57 (m, 3H), 7.42 (d, J = 8.1 Hz, 1H), 7.25 (dd, J = 2.7, 9.1 Hz, 1H), 7.13 (d, J = 2.7 Hz, 1H), 4.21 (m, 1H), 4.08-4.17 | 502.3 [M + H]+ |

| Example Number | Reference Scheme | Reference Example for Preparation | 1H-NMR (400 MHz, DMSO- d6) δ ppm | MS m/z (+ESI) |
|---|---|---|---|---|
| | | | (m, 2H), 3.97 (m, 1H), 3.92 (s, 3H), 3.54 (s, 2H), 3.17 (m, 1H), 2.70-2.86 (m, 2H) | |
| 43 | 1 | 1 | 8.35 (s, 1H), 8.00 (d, J = 7.8 Hz, 1H), 7.84 (d, J = 9.1 Hz, 1H), 7.22 (dd, J = 2.7, 9.1 Hz, 1H), 7.14 (d, J = 2.7 Hz, 1H), 7.01 (d, J = 1.7 Hz, 1H), 6.90-6.97 (m, 2H), 6.20 (m, 1H), 4.36 (m, 1H), 3.98 (m, 1H), 3.93 (s, 3H), 3.75 (m, 1H), 3.49 (m, 2H), 3.12 (m, 1H), 3.03 (m, 2H), 2.86-3.02 (m, 2H), 2.68 (m, 1H), 2.40 (m, 3H), 1.95-2.14 (m, 2H), 1.77 (m, 2H), 1.61 (m, 2H) | 505.2 [M + H]+ |
| 44 | 1 | 1 | 10.68 (s, 1H), 8.55 (s, 1H), 8.46 (dd, J = 7.0, 11.5 Hz, 1H), 7.87 (dd, J = 3.4, 9.3 Hz, 1H), 7.45 (m, 3H), 7.33 (dt, J = 2.9, 9.3 Hz, 1H), 7.11 (d, J = 2.8 Hz, 1H), 5.29 (m, 1H), 4.41 (m, 1H), 3.89 (s, 3H), 3.50 (m, 3H), 3.22 (m, 1H), 2.62-3.07 (m, 6H), 2.15 (m, 1H), 1.80 (m, 1H) | 491.1 [M + H]+ |
| 46 | 1 | 1 | 10.82 (br, 1H), 8.38 (s, 1H), 8.18 (d, J = 7.7 Hz, 1H), 7.78 (dd, J = 1.5, 9.2 Hz, 1H), 7.57 (t, J = 9.0 Hz, 1H), 7.47 (dd, J = 2.1, 8.4 Hz, 1H), 7.42 (d, J = 2.0 Hz, 1H), 6.99 (d, J = 8.4 Hz, 1H), 4.64 (s, 2H), 4.36 (d, J = 10.5 Hz, 1H), 3.99 (m, 4H), 3.76 (m, 1H), 3.32 (m, 1H), 2.95 (m, 3H), 2.35 (m, 3H), 2.07 (m, 2H), 1.78 (m, 2H), 1.55 (m, 2H) | 521.2 [M + H]+ |
| 47 | 1 | 1 | 10.69 (s, 1H), 8.78 (d, J = 6.9 Hz, 1H), 8.37 (s, 1H), 7.77 (dd, J = 1.6, 9.2 Hz, 1H), 7.57 (t, J = 9.0 Hz, 1H), 7.47 (m, 3H), 4.48 (m, 1H), 4.34 (m, 1H), 3.98 (m, 4H), 3.64 (m, 2H), 3.53 (s, 2H), 3.30 (m, 2H), 2.92-3.08 (m, 3H). | 509.1 [M + H]+ |
| 48 | 2 | 31 | 10.76 (s, 1H), 10.48 (s, 1H), 8.44 (s, 1H), 8.18 (d, J = 9.0 Hz, 1H), 8.13 (s, 1H), 7.66 (d, J = 0.6 Hz, 1H), 7.47-7.60 (m, 3H), 7.08 (d, J = 9.0 Hz, 1H), 4.22-4.34 (m, 3H), 4.03 (m, 1H), 4.00 (s, 3H), 3.31 (s, 2H), 3.24 (m, 1H), 2.87 (m, 1H), 2.68 (m, 1H) | 503.1 [M + H]+ |
| 50 | 1 | 1 | — | 521.1 [M + H]+ |
| 52 | 1 | 1 | 10.67 (s, 1H), 8.39 (s, 1H), 8.26 (d, J = 7.7 Hz, 1H), 7.85 (d, J = 9.1 Hz, 1H), 7.44 (m, 3H), 7.30 (dd, J = 2.7, 9.1 Hz, 1H), 7.23 (d, J = 2.7 Hz, 1H), 3.94 (s, 3H), 3.76 (m, 1H), 3.51 (s, 2H), 3.25 (m, 2H), 2.85-3.00 (m, 3H), 2.75 (m, 1H), 2.43 (m, 3H), 2.15 (m, 1H), 2.00 (m, 1H), 1.80 (m, 2H), 1.61 (m, 2H) | 535.2 [M + H]+ |
| 53 | 1 | 1 | — | 535.1 [M + H]+ |
| 56 | 1 | 1 | 10.81 (s, 1H), 8.45 (s, 1H), 8.16 (d, J = 7.7 Hz, 1H), 7.87 (d, J = 9.2 Hz, 1H), 7.43 (m, 2H), 7.20 (dd, J = 2.8, 9.2 Hz, 1H), 7.08 (d, J = 2.8 Hz, 1H), 7.00 (d, J = 8.3 Hz, 1H), 5.25 (m, 1H), 4.64 (s, 2H), 3.92 (s, 3H), 3.78 (m, 1H), 3.62 (m, 1H), 3.25 (m, 1H), 2.99 (m, 2H), 2.72 (m, 2H), 2.20 (m, 2H), 1.78 (m, 2H), 1.60 (m, 2H) | 489.1 [M + H]+ |
| 57 | 2 | 31 | 10.76 (s, 1H), 10.45 (s, 1H), 8.47 (s, 1H), 8.17 (s, 1H), 7.87 (d, J = 9.2 Hz, 1H), 7.66 (d, J = 0.6 Hz, 1H), 7.54 (m, 3H), 7.21 (dd, J = 2.8, 9.2 Hz, 1H), 7.06 (d, J = 2.8 Hz, 1H), 5.46 (m, 1H), 4.54 (m, 2H), 3.91 (s, 3H), 3.65 (m, 1H), 3.55 (s, 2H), 3.29 (m, 1H) | 488.0 [M + H]+ |
| 58 | 1 | 1 | 10.68 (s, 1H), 8.77 (d, J = 6.8 Hz, 1H), 8.48 (s, 1H), 8.19 (d, J = 9.1 Hz, | 478.4 [M + H]+ |

-continued

| Example Number | Reference Scheme | Reference Example for Preparation | 1H-NMR (400 MHz, DMSO-d6) δ ppm | MS m/z (+ESI) |
|---|---|---|---|---|
| | | | 1H), 7.45 (m, 3H), 7.06 (d, J = 9.1 Hz, 1H), 5.12 (m, 1H), 4.45 (m, 1H), 4.02 (s, 3H), 3.72 (t, J = 6.8 Hz, 1H), 3.58 (m, 2H), 3.52 (s, 2H), 3.30 (m, 1H), 3.19 (m, 2H), 2.86 (m, 2H) | |
| 60 | 1 | 1 | 10.67 (d, J = 2.3 Hz, 1H), 8.47 (m, 2H), 8.19 (dd, J = 4.7, 9.1 Hz, 1H), 7.45 (m, 3H), 7.06 (dd, J = 4.0, 9.1 Hz, 1H), 5.24 (m, 1H), 4.39 (m, 1H), 4.01 (s, 3H), 3.62 (m, 1H), 3.52 (s, 2H), 3.30 (m, 1H), 2.72-3.02 (m, 4H), 2.65 (m, 2H), 2.14 (m, 1H), 1.80 (m, 1H) | 492.4 [M + H]+ |
| 61 | 2 | 31 & 51 | 10.77 (s, 1H), 9.81 (s, 1H), 8.44 (s, 1H), 8.19 (d, J = 8.9 Hz, 1H), 7.71 (s, 1H), 7.54 (m, 3H), 7.09 (d, J = 8.9 Hz, 1H), 5.20 (t, J = 5.5 Hz, 1H), 4.56 (m, 2H), 4.22-4.37 (m, 3H), 4.09 (m, 1H), 4.02 (s, 3H), 3.55 (s, 2H), 3.28 (m, 1H), 2.92 (m, 1H), 2.79 (m, 1H) | 533.1 [M + H]+ |
| 62 | 1 | 34 | 10.51 (s, 1H), 8.37 (s, 1H), 7.77 (dd, J = 1.6, 9.2 Hz, 1H), 7.56 (t, J = 9.0 Hz, 1H), 7.24 (d, J = 7.9 Hz, 1H), 6.96 (m, 2H), 4.33 (m, 1H), 3.97 (s, 3H), 3.94 (m, 1H), 3.66 (s, 2H), 3.44 (s, 2H), 3.29 (m, 1H), 2.86 (m, 3H), 2.34 (m, 4H), 1.94 (m, 2H), 1.81 (m, 2H), 1.31 (m, 2H) | 523.1 [M + H]+ |
| 63 | 1 | 1 | 8.80 (d, J = 8.3 Hz, 1H), 8.39 (s, 1H), 7.85 (d, J = 9.1 Hz, 1H), 7.55 (s, 1H), 7.30 (dd, J = 2.7, 9.1 Hz, 1H), 7.23 (d, J = 2.7 Hz, 1H), 4.60 (m, 2H), 4.47 (m, 2H), 3.94 (s, 3H), 3.81 (m, 1H), 3.24 (m, 2H), 2.90 (m, 3H), 2.75 (m, 1H), 2.42 (m, 2H), 2.17 (m, 1H), 2.03 (m, 2H), 1.73 (m, 4H) | 508.1 [M + H]+ |
| 64 | 2 | 31 | 10.76 (s, 1H), 10.45 (s, 1H), 8.51 (s, 1H), 8.19 (m, 2H), 7.66 (d, J = 0.6 Hz, 1H), 7.47-7.57 (m, 3H), 7.08 (d, J = 9.1 Hz, 1H), 5.48 (m, 1H), 4.56 (d, J = 5.7 Hz, 2H), 4.01 (s, 3H), 3.67 (m, 1H), 3.55 (s, 2H), 3.38 (m, 1H) | 489.0 [M + H]+ |
| 65 | 1 | 1 | — | 493.1 [M + H]+ |
| 66 | 1 | 1 | 10.81 (s, 1H), 8.51 (s, 1H), 8.20 (d, J = 9.1 Hz, 1H), 8.15 (d, J = 7.8 Hz, 1H), 7.45 (dd, J = 2.1, 8.4 Hz, 1H), 7.41 (d, J = 2.0 Hz, 1H), 7.07 (d, J = 9.1 Hz, 1H), 7.00 (d, J = 8.3 Hz, 1H), 5.29 (m, 1H), 4.64 (s, 2H), 4.02 (s, 3H), 3.76 (m, 1H), 3.63 (m, 1H), 3.26 (m, 1H), 3.01 (m, 2H), 2.66-2.82 (m, 2H), 2.20 (m, 2H), 1.78 (m, 2H), 1.60 (m, 2H) | 490.1 [M + H]+ |
| 67 | 2 | 31 | 10.80 (s, 1H), 10.72 (s, 1H), 8.42 (s, 1H), 7.79 (dd, J = 1.5, 9.2 Hz, 1H), 7.66 (dd, J = 1.8, 8.2 Hz, 1H), 7.56 (m, 4H), 7.41 (d, J = 8.1 Hz, 1H), 4.25 (m, 1H), 4.11 (m, 2H), 4.00 (m, 1H), 3.97 (s, 3H), 3.54 (s, 2H), 3.28 (m, 1H), 2.99 (m, 1H), 2.64 (m, 1H) | 520.1 [M + H]+ |
| 68 | 2 | 31 & 51 | 10.78 (s, 1H), 9.72 (s, 1H), 8.38 (s, 1H), 8.16 (s, 1H), 7.86 (d, J = 9.1 Hz, 1H), 7.51 (m, 3H), 7.24 (dd, J = 2.7, 9.1 Hz, 1H), 7.12 (d, J = 2.6 Hz, 1H), 5.15 (t, J = 5.7 Hz, 1H), 4.58 (d, J = 5.6 Hz, 2H), 4.23 (m, 3H), 3.99 (m, 1H), 3.92 (s, 3H), 3.56 (s, 2H), 3.16 (m, 1H), 2.78 (m, 2H) | 532.5 [M + H]+ |
| 69 | 2 | 31 & 51 | 10.77 (s, 1H), 9.82 (s, 1H), 8.38 (s, 1H), 7.86 (d, J = 9.1 Hz, 1H), 7.72 (s, 1H), 7.52 (m, 3H), 7.24 (dd, J = 2.7, 9.1 Hz, 1H), 7.12 (d, J = 2.7 Hz, 1H), 5.21 (t, J = 5.5 Hz, 1H), 4.57 (m, 2H), | 532.4 [M + H]+ |

-continued

| Example Number | Reference Scheme | Reference Example for Preparation | 1H-NMR (400 MHz, DMSO- d6) δ ppm | MS m/z (+ESI) |
|---|---|---|---|---|
| 70 | 1 | 1 | 4.30 (m, 3H), 4.05 (m, 1H), 3.93 (s, 3H), 3.55 (s, 2H), 3.18 (m, 1H), 2.86 (m, 2H)<br>10.81 (s, 1H), 8.39 (s, 1H), 8.17 (d, J = 7.7 Hz, 1H), 7.85 (d, J = 9.1 Hz, 1H), 7.46 (dd, J = 2.1, 8.4 Hz, 1H), 7.41 (d, J = 2.0 Hz, 1H), 7.30 (dd, J = 2.7, 9.1 Hz, 1H), 7.23 (d, J = 2.7 Hz, 1H), 7.00 (d, J = 8.4 Hz, 1H), 4.64 (s, 2H), 3.94 (s, 3H), 3.76 (m, 1H), 3.24 (m, 2H), 2.85-3.00 (m, 3H), 2.75 (m, 1H), 2.43 (m, 3H), 2.16 (m, 1H), 2.00 (m, 1H), 1.79 (m, 2H), 1.61 (m, 2H) | 519.2 [M + H]+ |
| 71 | 2 | 31 | — | 534.2 [M + H]+ |
| 72 | 2 | 18 & 31 | — | 502.1 [M + H]+ |
| 73 | 2 | 18 & 31 | — | 502.1 [M + H]+ |
| 74 | 2 | 31 | — | 517.1 [M + H]+ |
| 75 | 2 | 31 | — | 517.2 [M + H]+ |
| 76 | 5 | 1 | 11.35 (s, 1H), 8.43 (s, 1H), 7.86 (d, J = 9.2 Hz, 1H), 7.75 (d, J = 8.3 Hz, 1H), 7.63 (d, J = 8.1 Hz, 1H), 7.48 (d, J = 8.1 Hz, 1H), 7.19 (dd, J = 2.8, 9.2 Hz, 1H), 7.08 (d, J = 2.8 Hz, 1H), 5.10 (m, 2H), 4.75 (s, 2H), 3.92 (s, 3H), 3.71 (m, 1H), 3.62 (m, 1H), 3.50 (m, 2H), 2.01 (m, 3H), 1.76 (m, 1H), 1.56 (m, 1H), 1.22-1.40 (m, 4H) | 505.2 [M + H]+ |
| 78 | 3 | 18 | 10.53 (s, 1H), 8.52 (2s, 1H), 7.82 (dt, J = 1.3, 9.3 Hz, 1H), 7.57 (td, J = 1.3, 9.2 Hz, 1H), 7.26 (dd, J = 2.0, 7.8 Hz, 1H), 6.97 (m, 2H), 5.15 (m, 1H), 3.99 (2s, 3H), 3.65-3.85 (m, 3H), 3.49 (m, 1H), 3.45 (2s, 2H), 3.40 (m, 1H), 3.26 (m, 1H), 2.98 (m, 1H), 1.65-2.10 (m, 5H), 1.24 (m, 2H) | 510.2 [M + H]+ |

Antimicrobial Activity Assay

The antibacterial activity of compounds is determined by the minimal inhibitory concentration (MIC) method. MICs for all bacteria except pneumococci and *Haemophilus influenzae* are obtained by broth microdilution with cation-adjusted Mueller-Hinton broth (CAMHB; BBL), according to CLSI guidelines (National Committee for Clinical Laboratory Standards. 2003. Methods for dilution antimicrobial susceptibility tests for bacteria that grow aerobically, 5$^{th}$ ed.; a approved standard M7-A6. National Committee for Clinical Laboratory Standards, Wayne, Pa.), with the following modifications: (i) for pneumococci CAMHB is supplemented with 5% (v/v) horse serum; (ii) for *Haemophilus influenzae* CAMHB is supplemented with 5% (v/v) Fildes enrichment (BBL) (Pankuch, G. A., Hoellman, D. B., Lin, G., Bajaksouzian, S., Jacobs, M. R., and Appelbaum, P. C. 1998. Activity of HMR 3647 compared to those of five agents against *Haemophilus influenzae* and *Moraxella catarrhalis* by MIC determination and time-kill assay. Antimicrob. Agents Chemother. 42:3032-3034). Microtiter plates are incubated at 35° C. in ambient air for 20 to 24 h, then inspected using an illuminated microtiter plate reader fitted with a magnifying mirror (MIC 2000; Cooke Laboratory Products, Alexandria, Va.). Compounds of the present invention are tested against several bacteria strains comprising some *Acinetobacter baumannii, Enterococcus faecalis, Enterococcus faecium, Escherichia coli, Haemophilus influenzae, Klebsiella pneumoniae, Pseudomonas aeruginosa, Staphylococcus aureus, Staphylococcus epidermidis, Streptococcus pyogenes; Enterobacter cloacae* and *Streptococcus pneumoniae*. All exemplified compounds have a MIC values for *Staphylococcus aureus* ATCC29213 or *Staphylococcus epidermidis* ATCC14990 lower or equal to 8 mg/L. Examples 1-7, 10, 12, 14-16, 19, 23, 24, 27-34, 36-45, 47, 49-56, 58-61, 64, 66, 68-71, 73-75 showed a MIC value of 8 mg/L or lower for *Streptococcus pneumoniae* ATCC49619. Examples 1-4, 6, 12, 21, 24, 25, 29, 30, 32, 38, 66 showed a MIC value of 8 mg/L or lower for *Escherichia coli* ATCC25922.

The invention claimed is:
1. A compound of formula I:

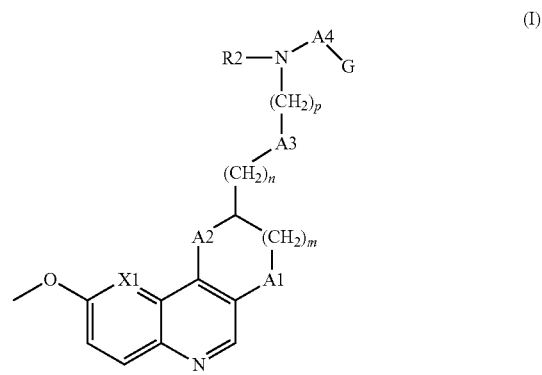

wherein
A1 represents —O—, —S— or —CH$_2$—;
A2 represents —CH$_2$— or —O—;
A3 represents C$_3$-C$_8$cycloalkylene; saturated or unsaturated 4 to 8-membered heterocyclodiyl with 1, 2 or 3 heteroatoms selected from nitrogen or oxygen, which group A3 is unsubstituted or substituted by one or more substituents each independently of the others being selected from fluorine, chlorine, bromine or iodine atoms, carboxy, alkyl, alkoxy, mono- or di($C_1$-$C_4$alkyl) amino, OH, =O, SH, =S, $NH_2$, =NH, cyano, $NO_2$, $C_1$-$C_4$alkoxycarbonyl, morpholinocarbonyl and hydroxy$C_1$-$C_4$alkyl groups;

A4 represents $C_1$-$C_4$alkylene or —C(=O)—;

G represents a group selected from pyrido[3,2-b][1,4]oxazine and benzo[1,4]oxazine which are unsubstituted or substituted by one or more substituents, each independently of the others being selected from fluorine, chlorine, bromine or iodine atoms, carboxy, alkyl, alkoxy, mono- or di($C_1$-$C_4$alkyl)amino, OH, =O, SH, =S, $NH_2$, =NH cyano and $NO_2$ groups and the pyrido or benzo part of the pyrido[3,2-b][1,4]oxazine and benzo[1,4]oxazine groups can also be substituted by $C_1$-$C_4$alkyl further substituted with fluoro;

X1 represents a nitrogen atom or CR1;

R1 represents a hydrogen atom or a halogen atom;

R2 represents a hydrogen atom;

m is 0 or 1;

n is 1; the —$(CH_2)_n$— group is unsubstituted;

p is 0 or 1;

or a pharmaceutically acceptable salt thereof.

2. A compound according to claim 1, wherein
X1 represents —CF, a nitrogen atom or —CH.

3. A compound according to claim 1, wherein
A1 represents —S— or —O—.

4. A compound according to claim 1, wherein
A2 represents —$CH_2$—.

5. A compound according to claim 1, wherein
A3 is a cyclohexylene group or a saturated or unsaturated 4 to 6-membered heterocyclodiyl with 1 or 2 nitrogen or oxygen atoms as heteroatoms.

6. A compound according to claim 5, wherein
A3 is selected from:

wherein
* indicates the bond to the $(CH_2)_p$ group in formula I.

7. A compound according to claim 6, wherein
A3 is selected from wherein * indicates the bond to the $(CH_2)_p$ group in formula I.

8. A compound according to claim 5, wherein
A3 is unsubstituted.

9. A compound according to claim 1, wherein
m is 1.

10. A compound according to claim 1, wherein
p is 0.

11. A compound according to claim 1, wherein
A4 represents —C(=O).

12. A compound according to claim 1, wherein
G is selected from a group of formula:

13. A compound according to claim 1, wherein
m is 1 and
A4 is —C(=O)—.

14. A compound according to claim 13, wherein
p is 0.

15. A compound according to claim 1 having 2 or more of the following features in combination:
(a) X1 is a nitrogen atom, —CH— or —CF—;
(b) A1 is —O—;
(c) A2 is —$CH_2$—;
(d) A3 is

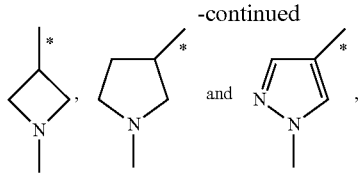

wherein
* indicates the bond to the $(CH_2)_p$ group in formula I;
(e) A3 is unsubstituted;
(f) G is selected from a group of formula:

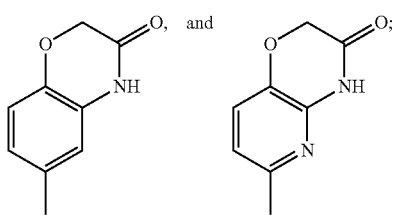

(g) —$(CH_2)_n$— is unsubstituted;
(h) A4 is —$(CH_2)$— or —$C(=O)$—.

16. A compound according to claim 1, wherein X1 is a nitrogen atom.

17. A compound according to claim 1, wherein X1 is —CH—.

18. A process for the preparation of a compound of formula I as claimed in claim 1, wherein a compound of formula II

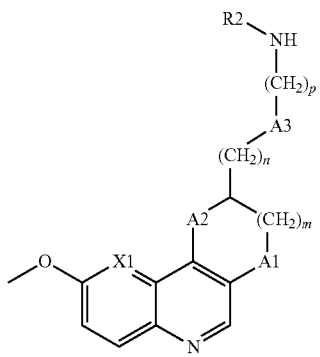

(II)

is reacted with a compound of formula III

G-A4b-L0  (III)

to generate the compound of formula I,
in which formulae
X1, R2, A1, A2, A3, G, m, n and p are as in formula I,
L0 is selected from —$CH_2Y$, —CHO, —COOH and —COCl,
Y is a leaving group,
A4b is absent or represents $C_1$-$C_3$alkylene.

19. A process for the preparation of a compound of formula I as claimed in claim 1, in which formula I $(CH_2)_n$— is unsubstituted, in which process a compound of formula IV

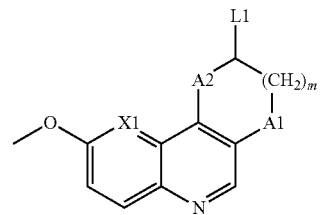

(IV)

is reacted with a compound of formula V

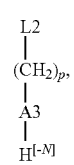

(V)

in which formulae
X1, A1, A2, m and p are as in formula I,
L1 is selected from —$CH_2Y$ or —CHO,
Y is a leaving group,
A3 is an unsubstituted or substituted, saturated or unsaturated 4 to 8-membered heterocyclodiyl group with 1, 2 or 3 heteroatoms selected from nitrogen or oxygen, at least one of which heteroatoms is a nitrogen atom, which group A3 is linked to the moiety

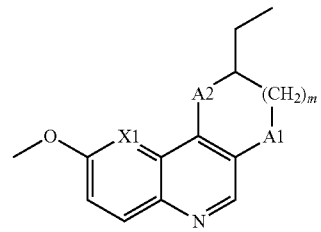

in formula I via a nitrogen ring atom of A3,
$H^{[-N]}$ in formula V represents a hydrogen atom bound to said nitrogen ring atom of A3, and
L2 is nitro or N(R2)E, wherein
R2 is as in formula I, and
E is -A4-G, with A4 and G being as defined in formula I, or an amino protecting group PG1, to generate the compound of formula I when E is -A4-G, or
a compound of formula VI

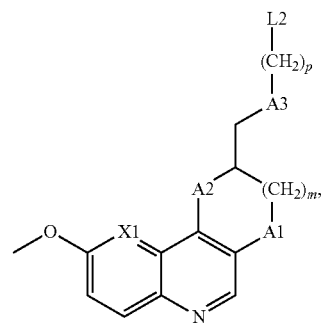

(VI)

wherein
X1, A1, A2, A3, m and p are as defined above, and
L2 is nitro or N(R2)E, with E being said amino protecting group PG1, and,
when L2 is nitro, said nitro group is reduced to an amino group and the amino derivative obtained is further reacted with a compound of formula III G-A4b-L0 (III)

wherein
G is as defined in formula I,
L0 is selected from —CH₂Y, —CHO, —COOH and —COCl,
Y is a leaving group,
A4b is absent or represents $C_1$-$C_3$alkylene; or,
when L2 is N(R2)E and E is an amino protecting group PG1, said protecting group is removed and the deprotected intermediate is further reacted with said compound of formula III, to generate the compound of formula I.

20. A process for the preparation of a compound of formula I as claimed in claim 1, in which formula I A1 is —O—, A2 is —CH₂—, m is 0 and —(CH₂)$_n$— is unsubstituted, in which process a compound of formula VII

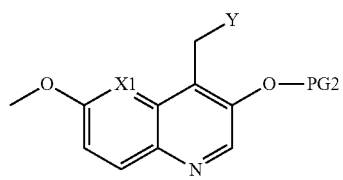
(VII)

is reacted with a compound of formula VIII

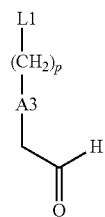
(VIII)

to generate a compound of formula IX

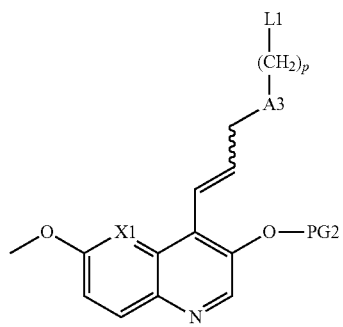
(IX)

in which formulae
X1, A3 and p are as in formula I,
L1 is nitro or N(R2)E,
R2 is as in formula I, and E is an amino protecting group PG1 or a group of formula -A4-G, wherein
A4 and G have the same meaning as in formula I,
Y is a phosphonium salt or a phosphonate group,
PG2 is a phenol protecting group, and
the compound of formula IX is further converted into a compound of formula XI

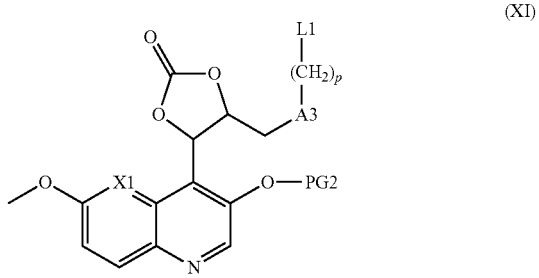
(XI)

wherein X1, PG2, A3, L1 and p are as defined above,
which compound of formula XI is then converted into the compound of formula I, when E is -A4-G, or
a compound of formula XIII

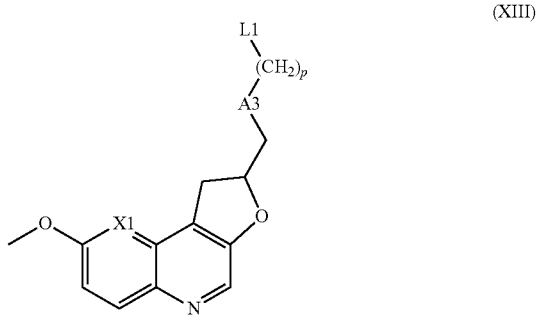
(XIII)

wherein X1, A3 and p are as defined above and
L1 is nitro or N(R2)E, with E being said amino protecting group PG1, and,
when L1 is nitro, said nitro group is reduced to an amino group and the amino derivative obtained is further reacted with a compound of formula III G-A4b-L0 (III)

wherein
G is as in formula I,
L0 is selected from —CH₂Y, —CHO, —COOH and —COCl,
Y is a leaving group,
A4b is absent or represents $C_1$-$C_3$alkylene; or,
when L1 is N(R2)E with E being an amino protecting group PG1, said protecting group is removed and the deprotected intermediate is further reacted with said compound of formula III to generate the compound of formula I.

21. A process for the preparation of a compound of formula I as claimed in claim 1, in which formula I A1 is —O—, A2 is —CH₂—, m is 1 and —(CH₂)$_n$— is unsubstituted, in which process a compound of formula XV

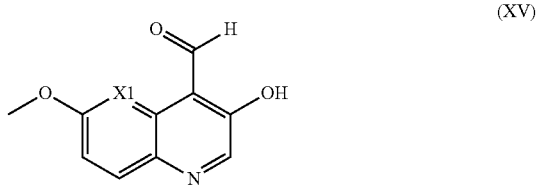
(XV)

is reacted with a compound of formula XVI

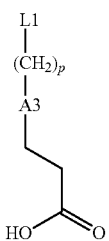
(XVI)

to generate a compound of formula XVII

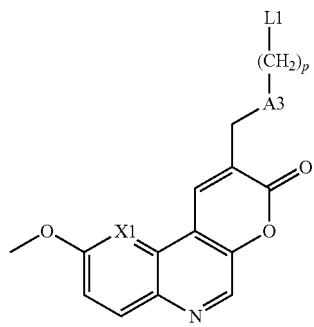
(XVII)

in which formulae
X1, A3 and p are as in formula I,
L1 is nitro or N(R2)E,
R2 is as in formula I, and
E is an amino protecting group PG1 or a group of formula -A4-G, wherein
A4 and G have the same meaning as in formula I,
which compound of formula XVII is converted into the compound of formula I, when E is -A4-G, or a compound of formula XIX

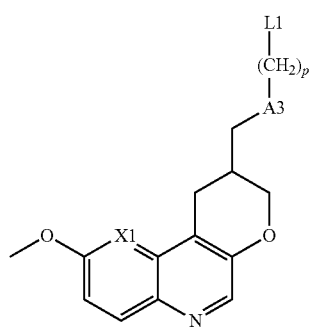
(XIX)

wherein X1, A3 and p are as defined above and
L1 is nitro or N(R2)E, with E being said amino protecting group PG1, and, when L1 is nitro, said nitro group is reduced to an amino group and the amino derivative obtained is further reacted with a compound of formula III G-A4b-L0    (III)

wherein
G is as defined in formula I,
L0 is selected from —CH$_2$Y, —CHO, —COOH and —COCl,
Y is a leaving group,
A4b is absent or represents C$_1$-C$_3$alkylene; or,
when L1 is N(R2)E with E being an amino protecting group PG1, said protecting group is removed and the deprotected intermediate is further reacted with said compound of formula III to generate the compound of formula I.

22. The compound of claim 2 wherein X1 is a nitrogen atom or —CH.

23. The compound of claim 3 wherein A 1 is —O—.

24. The compound of claim 12 wherein G is selected from a group consisting of

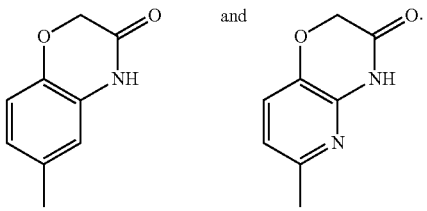

25. The compound of claim 7 wherein A3 is selected from a group consisting of

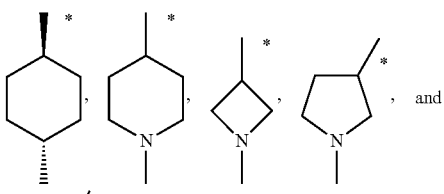

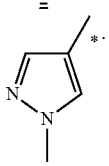

26. The compound according to claim 1, wherein said compound is 3-oxo-3,4-dihydro-2H-pyrido[3,2-b][1,4]oxazine-6-carboxylic acid [1-(6-methoxy-3,4-dihydro-2H-1-oxa-5,9-diaza-phenanthren-3-ylmethyl)-piperidin-4-yl]-amide.

27. The compound of claim 15, wherein A4 is —C(=O)—.

28. A pharmaceutical composition, comprising a compound according to claim 1, or a pharmaceutically acceptable salt thereof, and a pharmaceutically acceptable carrier.

* * * * *